(12) United States Patent
Xiao et al.

(10) Patent No.: US 10,654,934 B2
(45) Date of Patent: May 19, 2020

(54) USE OF CHIMERIC ANTIGEN RECEPTOR MODIFIED CELLS TO TREAT CANCER

(71) Applicant: Innovative Cellular Therapeutics CO., LTD., Shanghai (CN)

(72) Inventors: Lei Xiao, Shanghai (CN); Zhao Wu, Shanghai (CN); Chengfei Pu, Shanghai (CN); Zhiyuan Cao, Shanghai (CN); He Sun, Shanghai (CN); Mao Bi, Shanghai (CN)

(73) Assignee: Innovative Cellular Therapeutics Co., Ltd., Shanghai (CN)

(*) Notice: Subject to any disclaimer, the term of this patent is extended or adjusted under 35 U.S.C. 154(b) by 104 days.

(21) Appl. No.: 15/897,743

(22) Filed: Feb. 15, 2018

(65) Prior Publication Data

US 2018/0179289 A1 Jun. 28, 2018

Related U.S. Application Data

(63) Continuation-in-part of application No. 15/685,670, filed on Aug. 24, 2017, now Pat. No. 9,932,405, which is a continuation-in-part of application No. PCT/CN2017/078740, filed on Mar. 30, 2017.

(60) Provisional application No. 62/317,261, filed on Apr. 1, 2016.

(51) Int. Cl.

| C07K 16/28 | (2006.01) |
|---|---|
| C07K 14/59 | (2006.01) |
| A61P 35/00 | (2006.01) |
| C07K 14/705 | (2006.01) |
| C07K 14/72 | (2006.01) |
| C07K 14/725 | (2006.01) |
| A61K 39/00 | (2006.01) |

(52) U.S. Cl.
CPC .. C07K 16/2869 (2013.01); A61K 39/001102 (2018.08); A61K 39/001116 (2018.08); A61P 35/00 (2018.01); C07K 14/59 (2013.01); C07K 14/7051 (2013.01); C07K 14/70503 (2013.01); C07K 14/70507 (2013.01); C07K 14/70521 (2013.01); C07K 14/70532 (2013.01); C07K 14/70578 (2013.01); C07K 14/721 (2013.01); C07K 16/2809 (2013.01); A61K 2039/812 (2018.08); A61K 2039/82 (2018.08); A61K 2039/828 (2018.08); A61K 2039/892 (2018.08); C07K 2317/24 (2013.01); C07K 2317/622 (2013.01); C07K 2317/92 (2013.01); C07K 2319/03 (2013.01)

(58) Field of Classification Search
None
See application file for complete search history.

(56) References Cited

U.S. PATENT DOCUMENTS

| 7,446,190 | B2 | 11/2008 | Sadelain et al. |
|---|---|---|---|
| 8,221,751 | B2 | 7/2012 | Nakamura et al. |
| 8,546,546 | B2 | 10/2013 | Nakano |
| 8,785,600 | B2 | 7/2014 | Nam et al. |
| 9,073,992 | B2 | 7/2015 | Rees-Smith et al. |
| 9,315,580 | B2 | 4/2016 | Banchereau et al. |
| 2005/0113564 | A1* | 5/2005 | Campana ......... C07K 14/70517 530/350 |
| 2008/0292620 | A1 | 11/2008 | Damiano et al. |
| 2013/0287748 | A1 | 10/2013 | June et al. |
| 2014/0322275 | A1 | 10/2014 | Brogdon et al. |
| 2016/0256488 | A1 | 9/2016 | Wu |
| 2018/0346876 | A1 | 12/2018 | Xiao et al. |
| 2019/0000878 | A1 | 1/2019 | Xiao et al. |
| 2019/0112380 | A1 | 4/2019 | Chaudhary |
| 2019/0125798 | A1 | 5/2019 | Xiao et al. |
| 2019/0314411 | A1 | 10/2019 | Xiao et al. |

FOREIGN PATENT DOCUMENTS

| CN | 103492406 | 1/2014 | |
|---|---|---|---|
| CN | 104619723 | 5/2015 | |
| CN | 104829733 | 8/2015 | |
| WO | WO2006020837 A2 | 2/2006 | |
| WO | WO2014145252 | 9/2014 | |
| WO | WO2015142675 | 9/2015 | |
| WO | WO-2015142675 A2 * | 9/2015 | ............ A61K 39/00 |
| WO | WO2016014530 | 1/2016 | |
| WO | WO2016014553 | 1/2016 | |
| WO | WO2013033626 | 3/2016 | |
| WO | WO2016075612 | 5/2016 | |
| WO | WO2016126608 | 8/2016 | |
| WO | WO2017190096 A1 | 11/2017 | |
| WO | WO2018064921 A1 | 4/2018 | |

OTHER PUBLICATIONS

Jena et al. (Blood Aug. 19, 2010, 116(7): 1035-1044) (Year: 2010).*
Coleman, "Effects of amino acide sequence changes on antibody-antigen interactions," Biomolecular Research Institute, 55th Forum in Immunology, Australia, 1994, pp. 33-36.
Faupel-Badger et al., "Prolactin Receptor Expression adn Breast Cancer: RElationships with Tumor Characteristics among Pre- and Post-meopausal Women in a Population-Based Case—Control Study from Poland," Spring Science, Hormones and Cancer, Feb. 2014, pp. 42-50.
Ibragimova et al., "Stability of the B-Sheet of the WW Domain: A Molecular Dynamics Simulation Study," Biophysical Journal, European Molecular Biology Laboratory, Germany, vol. 77, Oct. 1999, pp. 2191-2198.

(Continued)

*Primary Examiner* — Misook Yu
(74) *Attorney, Agent, or Firm* — Lee & Hayes, P.C.

(57) ABSTRACT

The present disclosure relates to compositions and methods for compositions, methods, and kits for treating cancer using chimeric antigen receptor (CAR) modified cells. Some embodiments of the present disclosure relate to an isolated nucleic acid sequence encoding CAR. The CAR may include an antigen binding domain, a transmembrane domain, a costimulatory signaling region, and a CD3 zeta signaling domain. The antigen binding domain may bind to an antigen of a non-essential organ.

33 Claims, 27 Drawing Sheets

Specification includes a Sequence Listing.

(56) References Cited

OTHER PUBLICATIONS

International Search Report from corresponding PCT application No. PCT/CN2017/078740 dated Jul. 10, 2017, 5 pages.
Prazma et al., "Dendritic cell CD83: A therapeutic target or innocent bystander?," Immunology Letters, Department of Immunology, Duke University Medical Center, 2008, pp. 1-8.
Rudikoff et al., "Single amino acid substitution altering the antigen-binding specificity," PNAS USA, Laboratory of Cell Biology, National Institutes of Health, Mar. 1982, vol. 79, pp. 1979-1983.
Written Opinion from corresponding PCT application No. PCT/CN2017/078740 dated Jul. 10, 2017, 4 pages.
Kershaw et al., "Gene-engineered T cells for cancer therapy," Aug. 2013, Nature Reviews, 13:525-541.
Magee et al., "GUCY2C-directed CAR-T cells oppose colorectal cancer metatases without autoimmunity," 2016, Oncoimmunology, 5(10):e1227897. 10 pages.
Partial European Search Report dated Oct. 15, 2019 in European Application No. 17773247.6, a foreign corresponding application of U.S. Appl. No. 15/685,670, 15 pages.
Russo et al., "TSH receptor extracellular region mutations in thyroid functioning nodules: further evidence for the functional role of this region in the receptor activation," 2011, Endocrine, 40:492-494.
Snook et al., "GUCY2C-targeted cancer immunotherapy: past, present and future," 2011, Immunol Res, 51:161-169.
Magee, Michael S., "Guanylyl Cyclase C-Targeted CAR-T Cell Therapy for the Treatment of Metastatic Colorectal Cancer", 2015, Dissertation for Degree of Doctor of Philosophy in the Program of Immunology and Microbial Pathogenesis, Thomas Jefferson University. Philadelphia, Pennsylvania, 177 pages.

\* cited by examiner

| Antigen | Gene | Cancer Types |
|---|---|---|
| PRLR | Prolactin receptor | Breast cancer |
| GUCY2C | Guanylate cyclase 2C | Colorectal cancer |
| Muc17 | Mucin 17 | Gastric Cancer |
| CD207 | CD207 | Bladder Cancer |
| FZD10 | Frizzled family receptor 10 | Ovary tumor |
| TSHR | Thyroid stimulating hormone receptor | Thyroid Tumor |

FIG. 1

1:1  3:1  10:1  30:1  NT PRLR-K562

1:1  3:1  10:1  30:1  Anti-PRLR CAR

USE OF CHIMERIC ANTIGEN RECEPTOR MODIFIED CELLS TO TREAT CANCER

CROSS-REFERENCE TO RELATED APPLICATIONS

This application is a continuation-in-part of U.S. patent application Ser. No. 15/685,670, filed on Aug. 24, 2017, issued as U.S. Pat. No. 9,932,405 titled "Use of chimeric antigen receptor modified cells to treat cancer," which is a continuation-in-part-of International application number PCT/CN2017/078740, filed on Mar. 30, 2017, titled "Use of chimeric antigen receptor modified cells to treat cancer," which claims priority to U.S. Provisional Patent Application No. 62/317,261, filed on Apr. 1, 2016, titled "Use of chimeric antigen receptor modified cells to treat cancer," which are hereby incorporated by reference in their entirety.

SEQUENCE LISTING

The Sequence Listing associated with this application is provided in text format in lieu of a paper copy and is hereby incorporated by reference into the specification. The name of the text file containing the Sequence Listing is Sequence_listing.txt, which was created on or about Feb. 14, 2018. It has a file size of about 112 KB.

TECHNICAL FIELD

The present disclosure relates to modified cells and uses, in particular to compositions and methods for treating cancer using chimeric antigen receptor (CAR) modified cells.

BACKGROUND

Cancer is known as malignant tumors involving abnormal cell growth with the potential to invade or spread to other parts of the body. In humans, there are more than one hundred kinds of cancer, for example, breast cancer occurred in epithelial tissue of the breast. Since breast cancer cells lose characteristics of normal cells, the connection between breast cancer cells is loose. Once the cancer cells are exfoliated, these exfoliated cancer cells spread over bodies via the blood or lymph systems and therefore become life-threatening. Currently, breast cancer has become one of the common threats to women's physical and mental health. Immunotherapy (e.g., CAR T) has been proved to be effective for treating cancer. But there is a need to improve the immunotherapy to be more effective for certain cancer such as solid tumors.

SUMMARY

Embodiments of the present disclosure relate to compositions, methods, and kits for treating cancer using chimeric antigen receptor (CAR) modified cells.

Some embodiments of the present disclosure relate to an isolated nucleic acid sequence encoding a CAR. The CAR may include an antigen binding domain, a transmembrane domain, a costimulatory signaling region, and a CD3 zeta signaling domain. The antigen binding domain may bind to an antigen of a non-essential organ. For example, the antigen binding domain binds to an antigen that is expressed on the surface of a non-essential organ cell present in a microenvironment of a tumor.

Some embodiments of the present disclosure relate to an isolated CAR including an antigen binding domain, a transmembrane domain, a costimulatory signaling region, and a CD3 zeta signaling domain. The antigen binding domain may bind to an antigen of a non-essential organ.

Some embodiments of the present disclosure relate to a pharmaceutical composition including human T cells. The human T cells may include a nucleic acid sequence encoding a CAR. The CAR may include an antigen binding domain, a transmembrane domain, a costimulatory signaling region, and a CD3 zeta signaling domain. The antigen binding domain may bind to an antigen of a non-essential organ.

Some embodiments of the present disclosure relate to a cell including a nucleic acid sequence encoding a CAR. The CAR may include an antigen binding domain, a transmembrane domain, a costimulatory signaling region, and a CD3 zeta signaling domain. The antigen binding domain binds to an antigen of a non-essential organ. For example, the cell is selected from the group consisting of a T cell, a natural killer (NK) cell, a cytotoxic T lymphocyte (CTL), and a regulatory T cell.

Some embodiments of the present disclosure relate to a vector comprising a nucleic acid sequence encoding a CAR. The CAR may include an antigen binding domain, a transmembrane domain, a costimulatory signaling region, and a CD3 zeta signaling domain. The antigen binding domain may bind to an antigen of a non-essential organ.

Some embodiments of the present disclosure relate to a method for stimulating a T cell-mediated immune response to a cell population in a non-essential organ of a subject. The method may include administering to a subject an effective amount of a cell genetically modified to express a CAR. The CAR may include an antigen binding domain, a transmembrane domain, a costimulatory signaling region, and a CD3 zeta signaling domain. The antigen binding domain is selected to recognize the cell population of the non-essential organ specifically.

Some embodiments of the present disclosure relate to a method of treating a subject with cancer. The method may include administering to the subject a cell genetically engineered to express a CAR. The CAR may include an antigen binding domain, a transmembrane domain, a costimulatory signaling region, and a CD3 zeta signaling domain. The antigen binding domain may bind to an antigen of a non-essential organ. For example, the cell is selected from the group consisting of a T cell, a natural killer (NK) cell, a cytotoxic T lymphocyte (CTL), and a regulatory T cell.

In some embodiments, the antigen binding domain is an antibody, an antigen-binding fragment thereof, or a ligand thereof. For example, the antigen-binding fragment is a Fab or a scFv.

In some embodiments, the antigen is expressed on a non-essential organ cell present in a microenvironment of a tumor.

In some embodiments, the tumor is breast cancer. In certain embodiments, the antigen is a mammary gland antigen. For example, the mammary gland antigen is prolactin receptor (PRLR) having SEQ ID NO: 29. In some embodiments, the antigen binding domain is prolactin receptor ligand having SEQ ID NO: 20 or 44.

In some embodiments, the tumor is colorectal cancer. In certain embodiments, the antigen is a colon antigen. For example, the colon antigen is Guanylate cyclase 2C (GUCY2C) having SEQ ID NO: 33.

In some embodiments, the tumor is gastric cancer. In certain embodiments, the antigen is a gastric gland antigen. For example, the gastric gland antigen is Mucin 17 (Muc17) having SEQ ID NO: 31.

In some embodiments, the tumor is bladder cancer. In certain embodiments, the antigen is a bladder antigen. For example, the bladder antigen is CD207 having SEQ ID NO: 35.

In some embodiments, the tumor is an ovary tumor. In certain embodiments, the antigen is an ovary antigen. For example, the ovary antigen is Frizzled family receptor 10 (FZD10) having SEQ ID NO: 25.

In some embodiments, the tumor is a thyroid tumor. In certain embodiments, the antigen is a thyroid antigen. For example, the thyroid antigen is Thyroid stimulating hormone receptor (TSHR) having SEQ ID NO: 27.

In some embodiments, the costimulatory signaling region may include the intracellular domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds with CD83, and any combination thereof.

In some embodiments, the antigen binding domain may include at least one of SEQ ID NOs: 2-20 or 44.

In some embodiments, the antigen binding domain may include SEQ ID NO: 3 or 4, or a combination thereof, and the tumor is ovary tumor.

In some embodiments, the antigen binding domain may include SEQ ID NO: 6 or 7, or a combination thereof, and the tumor is thyroid tumor.

In some embodiments, the antigen binding domain may include SEQ ID NO: 9 or 10, or a combination thereof, and the tumor is breast cancer.

In some embodiments, the antigen binding domain may include SEQ ID NO: 12 or 13, or a combination thereof, and the tumor is gastric cancer.

In some embodiments, the antigen binding domain may include SEQ ID NO: 15 or 16, or a combination thereof, and the tumor is colorectal cancer.

In some embodiments, the antigen binding domain may include SEQ ID NO: 18 or 19, or a combination thereof, and the tumor is bladder cancer.

In some embodiments, the antigen binding domain may include SEQ ID NO: 20 or 44, and the tumor is breast cancer.

Some embodiments of the present disclosure relate to a method of selecting an antigen binding domain for a CAR for treating a subject with tumor cells. The method may include determining an organ of cells from that the tumor cells derived, determining that the organ is a non-essential organ with respect to the subject, searching a database to identify multiple markers that are expressed in a cell population of the organ, selecting a marker of the multiple markers based on a predetermined condition, and generating cells comprising a CAR using cells from the subject. The CAR may include an antigen binding domain, a transmembrane domain, a costimulatory signaling region, and a CD3 zeta signaling domain, and the antigen binding domain may bind to the marker.

In some embodiments, the predetermined condition may include the marker is present on the cell surface of a cell from that tumor cells are derived at least about at least one of 1.5-fold, 2-fold, 5-fold, 10-fold, 100-fold or 1000-fold greater than a suitable control cell, and the organ is non-essential such that an injury to the organ does not produce death of the subject.

In some embodiments, the non-essential organ is a mammary gland, and the marker is PRLR.

In some embodiments, the non-essential organ is a colon, and the marker is GUCY2C.

In some embodiments, the non-essential organ is a gastric gland, and the marker is Muc17.

In some embodiments, the non-essential organ is a bladder, and the marker is CD207.

In some embodiments, the non-essential organ is an ovary, and the marker is FZD10.

In some embodiments, the non-essential organ is thyroid, and the marker is TSHR.

In some embodiments, the tumor is selected from a group consisting of breast cancer, a thyroid tumor, colorectal cancer, an ovary tumor, bladder cancer, and bladder cancer.

Some embodiments of the present disclosure relate to a modified cell including a nucleic acid sequence encoding a CAR having one of SEQ ID NOs: 36-42. For example, the cell is selected from the group consisting of a T cell, a natural killer (NK) cell, a cytotoxic T lymphocyte (CTL), and a regulatory T cell.

In some embodiments, the CAR has SEQ ID NO: 38, and an antigen binding domain of the CAR binds to prolactin receptor ligand having SEQ ID NO: 20 or 44.

In some embodiments, the CAR has SEQ ID NO: 40, and an antigen binding domain of the CAR binds to GUCY2C having SEQ ID NO: 33.

In some embodiments, the CAR has SEQ ID NO: 39, and an antigen binding domain of the CAR binds to Muc17 having SEQ ID NO: 31.

In some embodiments, the CAR has SEQ ID NO: 41, and an antigen binding domain of the CAR binds to CD207 having SEQ ID NO: 35.

In some embodiments, the CAR has SEQ ID NO: 36, and an antigen binding domain of the CAR binds to FZD10 having SEQ ID NO: 25.

In some embodiments, the CAR has SEQ ID NO: 37, and an antigen binding domain of the CAR binds to TSHR having SEQ ID NO: 27.

Some embodiments relate to a pharmaceutical composition comprising human T cells. The human T cells may include a nucleic acid sequence encoding a CAR; the CAR comprises an antigen binding domain, a transmembrane domain, a costimulatory signaling region, and a CD3 zeta signaling domain. The antigen binding domain may include one of the amino acid sequences of SEQ ID NOs: 2, 5, 8, 11, 14, 17, or 20.

In some embodiments, the antigen binding domain comprises the amino acid sequence of SEQ ID NO: 2 and binds to Frizzled family receptor 10 (FZD10).

In some embodiments, the antigen binding domain comprises the amino acid sequence of SEQ ID NO: 5 and binds to Thyroid stimulating hormone receptor (TSHR).

In some embodiments, the CAR comprises the amino acid sequence of SEQ ID NO: 8 and binds to prolactin receptor (PRLR).

In some embodiments, the antigen binding domain comprises the amino acid sequence of SEQ ID NO: 11 and binds to Mucin 17 (Muc17).

In some embodiments, the antigen binding domain comprises the amino acid sequence of SEQ ID NO: 14 and binds to Guanylate cyclase 2C (GUCY2C).

In some embodiments, the antigen binding domain comprises the amino acid sequence of SEQ ID NO: 17 and binds to Langerin or Cluster of Differentiation 207 (CD207).

In some embodiments, the antigen binding domain comprises the amino acid sequence of SEQ ID NO: 20 and binds to PRLR.

In some embodiments, the CAR comprises the amino acid sequence of SEQ ID NO: 42 and binds to PRLR.

In some embodiments, the CAR comprises at least one of the amino acid sequences of SEQ ID NO: 36-42.

Some embodiments relate to a method for stimulating a T cell-mediated immune response to a cell population expressing an antigen. The method may include contacting the cell population with an effective amount of human T cells comprising a nucleic acid sequence encoding a CAR. The CAR may include an antigen binding domain, a transmembrane domain, a costimulatory signaling region, and a CD3 zeta signaling domain. The antigen binding domain may include one of the amino acid sequences of SEQ ID NOs: 2, 5, 8, 11, 14, 17, or 20.

In some embodiments, the antigen binding domain comprises the amino acid sequence of SEQ ID NO: 2, and the antigen is FZD10.

In some embodiments, the antigen binding domain comprises the amino acid sequence of SEQ ID NO: 5, and the antigen is TSHR.

In some embodiments, the CAR comprises the amino acid sequence of SEQ ID NO: 8, and the antigen is PRLR.

In some embodiments, the antigen binding domain comprises the amino acid sequence of SEQ ID NO: 11, and the antigen is Muc17.

In some embodiments, the antigen binding domain comprises the amino acid sequence of SEQ ID NO: 14, and the antigen is GUCY2C.

In some embodiments, the antigen binding domain comprises the amino acid sequence of SEQ ID NO: 17, and the antigen is CD207.

In some embodiments, the antigen binding domain comprises the amino acid sequence of SEQ ID NO: 20, and the antigen is PRLR.

In some embodiments, the CAR comprises the amino acid sequence of SEQ ID NO: 42, and the antigen is PRLR.

In some embodiments, the CAR comprises at least one of the amino acid sequences of SEQ ID NO: 36-42.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

The Detailed Description is described with reference to the accompanying figures. The use of the same reference numbers in different figures indicates similar or identical items.

FIG. 1 illustrates multiple tumors and antigens of non-essential organs as well as corresponding genes thereof.

DETAILED DESCRIPTION

Figure 2:
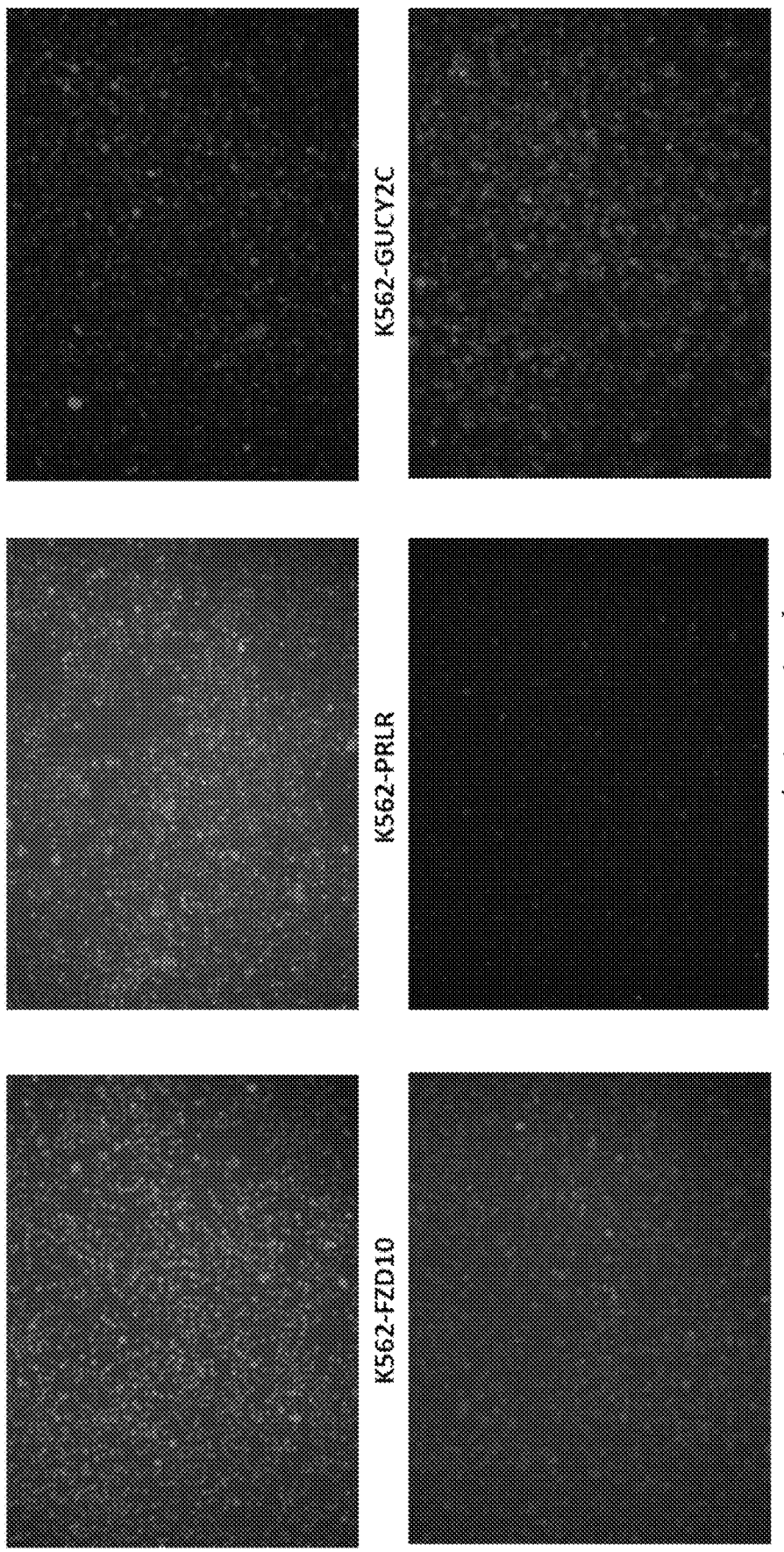
FIG. 2 shows the construction of antigen overexpressed K562 cell lines and includes images showing established target tumor cell lines.

The present disclosure relates to compositions and methods for treating cancer among other diseases. The embodiments of the present disclosure include constructing a CAR including an antigen binding domain that binds to an antigen corresponding to a target gene. The target gene is specifically expressed in a certain tissue (e.g., a group of cells or an organ) or expressed in the tissue more than expressed in other tissues. In some embodiments, the CAR is expressed in modified cells (e.g., T-cells or NK cells), which are administrated to a subject having a tumor derived from cells of the tissue. Because the antigen is expressed in the tumor, the modified cells may identify and then cause these tumor cells to be killed. The modified cells are able to replicate and expand in vivo, and therefore are present long-term in the body of the subject, leading to sustained tumor control. In these instances, non-tumor cells that express the antigen may also be killed or damaged by the transferred CAR T/NK cells. However, since the tissue is selected from non-essential tissues with respect to the subject, the killing of normal cells of the tissue does not cause a life-threatening event (e.g., complications) to the subject. Examples of the nonessential tissues include organs such as prostate, breast, or melanocyte.

In some embodiments, antigens selected for CARs are mainly expressed in cancer cells and their primary organs (e.g., non-essential organs). In certain embodiments, a non-essential organ may be removed, before treating of CAR T cells, from a subject who has cancer in an advanced stage derived from the non-essential organ. For example, treatment for stage IV thyroid cancer is usually a combination of treatment techniques including surgery and radioactive iodine treatment. In these instances, the entire thyroid is removed, and the procedure is called a total thyroidectomy. Since selected antigens are mainly expressed in thyroid normal cells and thyroid cancer cells, the risk of CAR T cells attacking normal cells is reduced.

Generally, treatment of breast cancer includes a topical therapy and systemic therapy. Topical treatment includes mastectomy and radiotherapy, which bring patients great suffering and are only available for treating breast cancer in early stages. Systemic treatment includes chemotherapy, endocrine therapy, and targeted molecular therapies. Chemotherapy causes patients great pain, and its efficacy is poor. Endocrine therapy mainly applies to postmenopausal women. Molecular targeted therapy is one of the most active areas of research in recent years. However, its efficiency is relatively low. For example, recurrence rates of typical HER2 monoclonal antibody Herceptin monotherapy in the treatment of breast cancer are 15% to 30%.

Ovarian cancer is one of the common malignant tumors of female genital mutilation. Among ovarian cancer, epithelial cancer and malignant germ cell tumors are common. Most epithelial ovarian tumors will spread to the uterus, bilateral annex, omentum and pelvic organs, causing a serious threat to women's lives. Different pathological types of ovarian cancer have different treatment options. Therapies combined with surgery and chemotherapy may be used for treating ovarian cancer. For ovarian cancer in early stages, surgeries may be available and include comprehensive surgery and preserving fertility surgery. Because the complexity of ovarian embryonic development, tissue anatomy, and endocrine functions, symptoms for early stages are not typical; therefore, diagnosis of benign and malignant as well as tissue types is quite difficult. In the case of pelvic tumor metastasis, especially malignant germ cell tumors of patients in late stages, most of these patients cannot remove the lesion. In these instances, radiation and chemotherapy can only be used as adjunctive therapy, and their effect is limited.

Endometrial cancer occurs in a group of endometrial tumors, also called endometrial cancer. Tumors originated in endometrial glands are known as endometrial adenocarcinoma. These cancer cells mainly spread directly or via lymphatic metastasis, while for those in late stages, the cancer cells may spread to the lung, liver, and bone via blood metastasis. Treatment plans may be decided based on clinical stages, levels of tumor differentiation, and general conditions of patients. Generally, the treatment includes surgical treatment as well as radiotherapy, hormone, and chemotherapy. Conservative surgery may cause a relapse, while radical resection may cause symptoms of premature menopause. Radiation and chemotherapy can only be used as adjunctive therapies, and their effect is limited. Progestin therapy is effective using progesterone drugs to control the development of cancer, but the dosage is large, and long-term progestin therapies may impair liver functions. For patients with advanced tumor metastases, no effective treatment is available.

Cervical cancer is the most common form of female genital malignancies, including carcinoma in situ and invasive carcinoma. Cervical cancer is limited to the mucosa of the cortex, known as carcinoma in situ when no infiltration. When cancer stromal invasion is under mucous membranes, it is called invasive cancer. Cervical cancer can cause infertility in women. Since invasion and metastasis of advanced cancer, the symptoms may appear corresponding parts of the body as well. Generally, treatment plans are decided based on clinical stages, levels of tumor differentiation, and general conditions of patients. Generally, the treatment includes surgical treatment, as well as radiotherapy and chemotherapy as adjuvant therapy. Surgical treatment includes Radical hysterectomy and pelvic lymph node surgery Elimination, and there are recurrence risks. Radiation and chemotherapy can only be used as adjunctive therapies, and their effect is limited. For patients with advanced tumor metastases, currently, no effective treatment is available.

Thyroid cancer is the most common thyroid malignancy. There are four common thyroid cancer types: papillary (e.g., mixed papillary-follicular carcinoma), follicular, medullary (e.g., an entity with amyloidosis thyroid tumors) and undifferentiated carcinoma. Generally, treatment of papillary and follicular carcinoma is relatively effective, while medullary carcinoma is often transferred along lymphatic and blood roads and undifferentiated carcinoma is less common. Advanced thyroid cancer may produce hoarseness, breathing, difficulty swallowing, and Horner syndrome and sympathetic nerve compression caused by cervical plexus violations occur ear, pillows, shoulder pain, etc. and regional lymph nodes and distant metastasis, etc. There is a need for improving the level of prognosis and treatment of thyroid cancer. Current modes of treatment for thyroid cancer include surgery, postoperative radionuclide therapy, and endocrine therapy after surgery, wherein the surgical treatment is the first choice. In choices of surgery methods for treating differentiated thyroid cancer, many aspects of postoperative radioiodine treatment and TSH (thyroid stimulating hormone, TSH) suppression therapy, etc. have controversy. Also, there are no unified and standardized treatment guidelines, resulting in incomplete or excessive treatment. For advanced differentiated thyroid cancer, there is no effective treatment.

Colorectal cancer is a type of common gastrointestinal cancer, a serious threat to life and health. There is a need for improving the level of prognosis and treatment of colorectal cancer. Generally, clinical treatment programs for colorectal cancer include local excision, chemotherapy, and biologic therapy. The use of local excision of metastatic lesions: the standard of biological disease (example: synchronization and anisotropy) is important but difficult to be evaluated. For example, 75% of patients will relapse after liver metastases resection of the disease. Most of the relapsing occurs in livers, and its efficacy is limited. Commonly used chemotherapy regimens include FOLFOX, FOLFIRI, CapeOX, and FOLFOXIRI (2B), and other, However, combined with FOLFOX regimen 7%-8% of patients can extend 3-year PFS, while overall survival rates are not significant. Recent experimental data suggest that adding cetuximab to FOLFOX application for possible transfer patients with resectable lesions is harmful. Based on the current research data, combined with biological agents (e.g., bevacizumab, cetuximab, and panitumumab) treatment with these drugs have been recommended.

However, monoclonal antibody drugs generally have problems such as efficacy and persistence. Patients need long-term, repeated drug uses. At the same time, due to the combined treatment methods are generally stronger than monotherapy; therefore, whether other types of drugs will affect treatment and prognosis is still a question.

Stomach cancer (gastric cancer) is a malignant gastric epithelial origin, one of the most common gastrointestinal malignancies. Pain and weight loss are the most common clinical symptoms of advanced gastric cancer. Proliferation and metastasis pathway of gastric cancer cells include lymphatic metastasis, direct invasion, hematogenous metastasis, and peritoneal metastasis. There is a need for improving the level of prognosis and treatment of gastric cancer. Generally, gastric cancer treatment modes include surgery, chemotherapy, radiotherapy, immunotherapy, etc. But most cases of advanced gastric cancer have unresectable primary or metastatic lesions. Tumor metastasis and recurrence of gastric cancer are the leading causes of poor prognosis Esophageal cancer (esophageal cancer, EC) is originated in the esophageal mucosal epithelial malignancies and is a common clinical malignant tumor. Tumor metastasis and recurrence of esophageal cancer are the leading causes of poor prognosis. Due to incidence and mortality, esophageal cancer is among the top ten in malignant tumors. There is a need for improving the level of prognosis and treatment of esophageal cancer. The current mode of treatment of esophageal cancer is a surgical combined therapy. There are problems in the staging of esophageal cancer, surgical treatment mode selection, surgical approach selection, lymphadenectomy way, and postoperative adjuvant therapy, etc.

Unless defined otherwise, all technical and scientific terms used herein have the same meaning as commonly understood by those of ordinary skill in the art to which the disclosure belongs. Although any methods and materials similar or equivalent to those described herein can be used in the practice or testing of the present disclosure, preferred methods and materials are described. For the purposes of the present disclosure, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

The term "activation," as used herein, refers to the state of a T cell that has been sufficiently stimulated to induce detectable cellular proliferation. Activation can also be associated with induced cytokine production and detectable effector functions. The term "activated T cells" refers to, among other things, T cells that are undergoing cell division.

The term "antibody" is used in the broadest sense and specifically covers monoclonal antibodies (including full-length monoclonal antibodies), multispecific antibodies (e.g., bispecific antibodies), and antibody fragments so long as they exhibit the desired biological activity or function. The antibodies of the present disclosure may exist in a variety of forms including, for example, polyclonal antibodies, monoclonal antibodies, Fv, Fab and F(ab)$_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

"Antibody fragments" comprise a portion of a full-length antibody, generally the antigen-binding or variable region of the antibody. Examples of antibody fragments include Fab, Fab', F(ab')2, and Fv fragments; diabodies; linear antibodies; single-chain antibody molecules; and multispecific antibodies formed from antibody fragments.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of a Fv including only three complementarity determining regions (CDRs) specific for an antigen) has the ability to recognize and bind antigen, although at a lower affinity than the entire binding site. An "antibody heavy chain," as used herein, refers to the larger of the two types of polypeptide chains present in all antibody molecules in their naturally occurring conformations. An "antibody light chain," as used herein, refers to the smaller of the two types of polypeptide chains present in all antibody molecules in their naturally occurring conformations. K and A light chains refer to the two major antibody light chain isotypes.

By the term, "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" as used herein is defined as a molecule that provokes an immune response, which may involve either antibody production, or the activation of specific immunologically competent cells, or both. Antigens may include any macromolecule, including virtually all proteins or peptides, or molecules derived from recombinant or genomic DNA. For example, DNA including a nucleotide sequence or a partial nucleotide sequence encoding a protein that elicits an immune response, therefore, encodes an "antigen" as that term is used herein. Furthermore, an antigen need not be encoded solely by a full-length nucleotide sequence of a gene. Further, an antigen can be generated, synthesized or derived from a biological sample including a tissue sample, a tumor sample, a cell or a biological fluid.

The term "anti-tumor effect" as used herein, refers to a biological effect associated with a decrease in tumor volume, a decrease in the number of tumor cells, a decrease in the number of metastases, an increase in life expectancy of a subject having tumor cells, or amelioration of various physiological symptoms associated with the cancerous condition. An "anti-tumor effect" can also be manifested by the ability of the peptides, polynucleotides, cells, and antibodies of the disclosure in the prevention of the occurrence of tumor in the first place.

The term "autoantigen" refers to an antigen mistakenly recognized by the immune system as being foreign. Autoantigens include cellular proteins, phosphoproteins, cellular surface proteins, cellular lipids, nucleic acids, glycoproteins, including cell surface receptors.

The term "autologous" is used to describe a material derived from the same individual to which it is later to be re-introduced into the individual.

"Allogeneic" is used to describe a graft derived from a different animal of the same species.

"Xenogeneic" is used to describe a graft derived from an animal of a different species.

The term "cancer" as used herein is defined as a disease characterized by the rapid and uncontrolled growth of aberrant cells. Cancer cells can spread locally or through the bloodstream and lymphatic system to other parts of the body. Examples of various cancers include breast cancer, prostate cancer, ovarian cancer, cervical cancer, skin cancer, pancreatic cancer, colorectal cancer, renal cancer, liver cancer, brain cancer, lymphoma, leukemia, lung cancer et al.

Throughout this specification, unless the context requires otherwise, the words "comprise," "includes" and "including" will be understood to imply the inclusion of a stated step or element or group of steps or elements but not the exclusion of any other step or element or group of steps or elements.

By "consisting of" is meant including, and limited to, whatever follows the phrase "consisting of." Thus, the phrase "consisting of" indicates that the listed elements are required or mandatory and that no other elements may be present.

By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The terms "complementary" and "complementarity" refer to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands.

By "corresponds to" or "corresponding to" is meant (a) a polynucleotide having a nucleotide sequence that is substantially identical or complementary to all or a portion of a reference polynucleotide sequence or encoding an amino acid sequence identical to an amino acid sequence of a peptide or protein; or (b) a peptide or polypeptide having an amino acid sequence that is substantially identical to a sequence of amino acids in a reference peptide or protein.

"Co-stimulatory ligand," includes a molecule on an antigen presenting cell (e.g., an APC, dendritic cell, B cell, et al.) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including proliferation, activation, differentiation, et al. A co-stimulatory ligand can include CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds to a costimulatory molecule present on a T cell, such as CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds to a costimulatory ligand, thereby mediating a co-stimulatory response by the T cell, such as proliferation. Co-stimulatory molecules include an MHC class I molecule, BTLA, and a Toll-like receptor.

A "co-stimulatory signal" refers to a signal, which in combination with a primary signal, such as TCR/CD3 ligation, leads to T cell proliferation and/or upregulation or down regulation of key molecules.

As used herein, the terms "disease" and "condition" may be used interchangeably or may be different in that the particular malady or condition may not have a known causative agent (so that etiology has not yet been worked out), and it is therefore not yet recognized as a disease but only as an undesirable condition or syndrome, wherein a more or less specific set of symptoms have been identified by clinicians. As used herein, a "disease" is a state of health of a subject wherein the subject cannot maintain homeostasis, and wherein if the disease is not ameliorated then the subject's health continues to deteriorate. In contrast, a "disorder" in a subject is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term "effective" means adequate to accomplish a desired, expected, or intended result. For example, an "effective amount" may be an amount of a compound sufficient to produce a therapeutic or prophylactic benefit.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

With regard to polynucleotides, the term "exogenous" refers to a polynucleotide sequence that does not naturally occur in a wild-type cell or organism but is typically introduced into the cell by molecular biological techniques. Examples of exogenous polynucleotides include vectors, plasmids, and/or man-made nucleic acid constructs encoding the desired protein. With regard to polynucleotides, the term "endogenous" or "native" refers to naturally-occurring polynucleotide sequences that may be found in a given wild-type cell or organism. Also, a particular polynucleotide sequence that is isolated from a first organism and transferred to the second organism by molecular biological techniques is typically considered an "exogenous" polynucleotide with respect to the second organism. In specific embodiments, polynucleotide sequences can be "introduced" by molecular biological techniques into a microorganism that already contains such a polynucleotide sequence, for instance, to create one or more additional copies of an otherwise naturally-occurring polynucleotide sequence, and thereby facilitate overexpression of the encoded polypeptide.

The term "expression" as used herein is defined as the transcription and/or translation of a particular nucleotide sequence driven by its promoter.

"Expression vector" refers to a vector including a recombinant polynucleotide including expression control sequences operatively linked to a nucleotide sequence to be expressed. An expression vector includes sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared ×100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The term "immunoglobulin" or "Ig," refers to a class of proteins, which function as antibodies. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function but may serve as an antigen receptor. IgE is the immunoglobulin that mediates immediate hypersensitivity by causing the release of mediators from mast cells and basophils upon exposure to the allergen.

By "isolated" is meant a material that is substantially or essentially free from components that normally accompany it in its native state. For example, an "isolated polynucleotide," as used herein, refers to a polynucleotide, which has been purified from the sequences which flank it in a naturally-occurring state, e.g., a DNA fragment which has been removed from the sequences that are normally adjacent to the fragment. Alternatively, an "isolated peptide" or an "isolated polypeptide" and the like, as used herein, refer to in vitro isolation and/or purification of a peptide or polypeptide molecule from its natural cellular environment, and from association with other components of the cell.

In the context of the present disclosure, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

A "lentivirus" as used herein refers to a genus of the Reoviridae family. Lentiviruses are unique among the retroviruses in being able to infect nondividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

The nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "overexpressed" tumor antigen or "overexpression" of the tumor antigen is intended to indicate an abnormal level of expression of the tumor antigen in a cell from a disease area like a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

"Parenteral" administration of an immunogenic composition includes, e.g., subcutaneous (s.c.), intravenous (i.v.), intramuscular (i.m.), or intracisternal injection, or infusion techniques.

The terms "patient," "subject," "individual," et al. are used interchangeably herein, and refer to any animal, or cells thereof whether in vitro or in situ, amenable to the methods described herein. In certain non-limiting embodiments, the patient, subject or individual is a human. In some embodiments, the term "subject" is intended to include living organisms in which an immune response can be elicited (e.g., mammals). Examples of subjects include humans, dogs, cats, mice, rats, and transgenic species thereof.

The recitation "polynucleotide" or "nucleic acid" as used herein designates mRNA, RNA, cRNA, rRNA, cDNA or DNA. The term typically refers to a polymeric form of nucleotides of at least 10 bases in length, either ribonucleotides or deoxynucleotides or a modified form of either type of nucleotide. The term includes single and double stranded forms of DNA and RNA.

The terms "polynucleotide variant" and "variant" and the like refer to polynucleotides displaying substantial sequence identity with a reference polynucleotide sequence or polynucleotides that hybridize to a reference sequence under stringent conditions that are defined hereinafter. These terms also encompass polynucleotides that are distinguished from a reference polynucleotide by the addition, deletion or substitution of at least one nucleotide. Accordingly, the terms "polynucleotide variant" and "variant" include polynucleotides in which one or more nucleotides have been added or deleted, or replaced with different nucleotides. In this regard, it is well understood in the art that certain alterations inclusive of mutations, additions, deletions, and substitutions can be made to a reference polynucleotide whereby the altered polynucleotide retains the biological function or activity of the reference polynucleotide or has increased activity in relation to the reference polynucleotide (i.e., optimized). Polynucleotide variants include, for example, polynucleotides having at least 50% (and at least 51% to at least 99% and all integer percentages in between, e.g., 90%, 95%, or 98%) sequence identity with a reference polynucleotide sequence described herein. The terms "polynucleotide variant" and "variant" also include naturally-occurring allelic variants and orthologs that encode these enzymes.

"Polypeptide," "polypeptide fragment," "peptide" and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally occurring amino acid polymers. In certain aspects, polypeptides may include enzymatic polypeptides, or "enzymes," which typically catalyze (i.e., increase the rate of) various chemical reactions.

The recitation polypeptide "variant" refers to polypeptides that are distinguished from a reference polypeptide sequence by the addition, deletion or substitution of at least one amino acid residue. In certain embodiments, a polypeptide variant is distinguished from a reference polypeptide by one or more substitutions, which may be conservative or non-conservative. In certain embodiments, the polypeptide variant comprises conservative substitutions and, in this regard, it is well understood in the art that some amino acids may be changed to others with broadly similar properties without changing the nature of the activity of the polypeptide. Polypeptide variants also encompass polypeptides in which one or more amino acids have been added or deleted, or replaced with different amino acid residues.

The term "promoter" as used herein is defined as a DNA sequence recognized by the synthetic machinery of the cell or introduced synthetic machinery, required to initiate the specific transcription of a polynucleotide sequence. The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

The term "bind," "binds," or "interacts with" means that one molecule recognizes and adheres to a particular second molecule in a sample or organism, but does not substantially recognize or adhere to other structurally unrelated molecules in the sample. By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross-reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A," the presence of a molecule containing epitope A (or free, unlabeled A), in a reaction containing labeled "A" and the antibody, will reduce the amount of labeled A bound to the antibody.

A "soluble receptor" is a receptor polypeptide that is not bound to a cell membrane. Soluble receptors are most commonly ligand-binding receptor polypeptides that lack transmembrane and cytoplasmic domains. Soluble receptors may include additional amino acid residues, such as affinity tags that provide for purification of the polypeptide or provide sites for attachment of the polypeptide to a substrate, or immunoglobulin constant region sequences. Many cell-surface receptors have naturally occurred, soluble counterparts that are produced by proteolysis. Soluble receptor polypeptides are said to be substantially free of transmembrane and intracellular polypeptide segments when they lack sufficient portions of these segments to provide membrane anchoring or signal transduction, respectively.

By "statistically significant," it is meant that the result was unlikely to have occurred by chance. Statistical significance can be determined by any method known in the art. Commonly used measures of significance include the p-value, which is the frequency or probability with which the observed event would occur if the null hypothesis were true. If the obtained p-value is smaller than the significance level, then the null hypothesis is rejected. In simple cases, the significance level is defined at a p-value of 0.05 or less. A "decreased" or "reduced" or "lesser" amount is typically a "statistically significant" or a physiologically significant amount, and may include a decrease that is about 1.1, 1.2, 1.3, 1.4, 1.5, 1.6 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000 times) (including all integers and decimal points in between and above 1, e.g., 1.5, 1.6, 1.7. 1.8, etc.) an amount or level described herein.

By the term "stimulation," is meant a primary response induced by binding of a stimulatory molecule (e.g., a TCR/CD3 complex) with its cognate ligand thereby mediating a signal transduction event, such as signal transduction via the TCR/CD3 complex. Stimulation can mediate altered expression of certain molecules, such as downregulation of TGF-β, and/or reorganization of cytoskeletal structures et al.

A "stimulatory molecule" refers to a molecule on a T cell that specifically binds to a cognate stimulatory ligand present on an antigen presenting cell.

A "stimulatory ligand" refers to a ligand that when present on an antigen presenting cell (e.g., an APC, a dendritic cell, a B-cell, et al.) can specifically bind with a cognate binding partner (referred to herein as a "stimulatory molecule") on a T cell, thereby mediating a primary response by the T cell, including activation, initiation of an immune response, proliferation, et al. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to a cell that has been separated from the cells with which they are naturally associated in their natural state. In some embodiments, the cells are cultured in vitro. In other embodiments, the cells are not cultured in vitro.

The term "therapeutic" as used herein means a treatment and/or prophylaxis. A therapeutic effect is obtained by suppression, remission, or eradication of a disease state.

The term "therapeutically effective amount" refers to the amount of the subject compound that will elicit the biological or medical response of tissue, system, or subject that is being sought by the researcher, veterinarian, medical doctor or another clinician. The term "therapeutically effective amount" includes that amount of a compound that, when administered, is sufficient to prevent the development of, or alleviate to some extent, one or more of the signs or symptoms of the disorder or disease being treated. The therapeutically effective amount will vary depending on the compound, the disease and its severity and the age, weight, etc., of the subject to be treated.

To "treat" disease as the term is used herein, means to reduce the frequency or severity of at least one sign or symptom of a disease or disorder experienced by a subject.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which includes an isolated nucleic acid and which can be used to deliver the isolated nucleic acid to the interior of a cell. Numerous vectors are known in the art including linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, et al. Examples of viral vectors include, but are not limited to, adenoviral vectors, adeno-associated virus vectors, retroviral vectors et al. For example, lentiviruses are complex retroviruses, which, in addition to the common retroviral genes gag, pol, and env, contain other genes with regulatory or structural function. Lentiviral vectors are well known in the art. Some examples of lentivirus include the Human Immunodeficiency Viruses: HIV-1, HIV-2, and the Simian Immunodeficiency Virus: SIV. Lentiviral vectors have been generated by attenuating the HIV virulence genes, for example, the genes env, vif, vpr, vpu, and nef are deleted making the vector biologically safe.

Ranges: throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The present disclosure relates to isolated nucleic acid sequences, vectors including the isolated nucleic acid sequences, cells including the isolated nucleic acid sequences and methods of treating cancer using these cells.

Some embodiments of the present disclosure relate to an isolated nucleic acid sequence encoding a CAR. The CAR may include an antigen binding domain, a transmembrane domain, a costimulatory signaling region, and a CD3 zeta signaling domain. The antigen binding domain may bind to an antigen of a non-essential organ. For example, the antigen binding domain binds to an antigen that is expressed on the surface of a non-essential organ cell present in a microenvironment of a tumor.

As used herein, a non-essential organ refers to an organ of a subject, and the organ is non-essential such that an injury to the organ does not produce death of the subject. In some embodiments, an injury of the organ does not visibly affect the subject's health. For example, the prostate may be a non-essential organ for a male mammal, while breast may be a non-essential organ for a female mammal.

In certain embodiments, a non-essential organ may be removed, before treating of CAR T cells, from a subject who has cancer in an advanced stage derived from the non-essential organ. In these instances, the impact of treating of CAR T cells targeting antigens of the non-essential organ on the subject is substantially reduced. Examples of non-essential organs include a mammary gland, a colon, a gastric gland, an ovary, and a thyroid.

Some embodiments of the present disclosure relate to an isolated CAR including an antigen binding domain, a transmembrane domain, a costimulatory signaling region, and a CD3 zeta signaling domain. The antigen binding domain may bind to an antigen of a non-essential organ.

Some embodiments of the present disclosure relate to a pharmaceutical composition including human T cells. The human T cells may include a nucleic acid sequence encoding a CAR. The CAR may include an antigen binding domain, a transmembrane domain, a costimulatory signaling region, and a CD3 zeta signaling domain. The antigen binding domain may bind to an antigen of a non-essential organ.

Some embodiments of the present disclosure relate to a cell including a nucleic acid sequence encoding a CAR. The CAR may include an antigen binding domain, a transmembrane domain, a costimulatory signaling region, and a CD3 zeta signaling domain. The antigen binding domain binds to an antigen of a non-essential organ. For example, the cell is selected from the group consisting of a T cell, a natural killer (NK) cell, NK-92 cell, a cytotoxic T lymphocyte (CTL), and a regulatory T cell.

Some embodiments of the present disclosure relate to a vector comprising a nucleic acid sequence encoding a CAR. The CAR may include an antigen binding domain, a transmembrane domain, a costimulatory signaling region, and a CD3 zeta signaling domain. The antigen binding domain may bind to an antigen of a non-essential organ.

Some embodiments of the present disclosure relate to a method for stimulating a T cell-mediated immune response to a cell population in a non-essential organ of a subject. The method may include administering to a subject an effective amount of a cell genetically modified to express a CAR. The CAR may include an antigen binding domain, a transmembrane domain, a costimulatory signaling region, and a CD3 zeta signaling domain. The antigen binding domain is selected to recognize the cell population of the non-essential organ specifically.

In some embodiments, the T cells may be modified to have a disruption in an endogenous gene associated with a biosynthesis or transportation pathway of one or more proteins. Examples of the one or more proteins include Programmed cell death protein 1 (PD-1) gene and Major Histocompatibility Complex I (MHC I). For example, Major Histocompatibility Complex of T cells may be disrupted by modification of Beta-2-microglobulin (B2M) gene, antigen presentation 1 (TAP1) gene, and TAP-associated glycoprotein (TAPBP) gene in the T cells. In certain embodiments, the disruption may be introduced into a T cell before or after the T cell is transferred with a nucleic acid sequence encoding a CAR.

Some embodiments of the present disclosure relate to a method of treating a subject with cancer. The method may include administering to the subject a cell genetically engineered to express a CAR. The CAR may include an antigen binding domain, a transmembrane domain, a costimulatory signaling region, and a CD3 zeta signaling domain. The antigen binding domain may bind to an antigen of a non-essential organ. For example, the cell is selected from the group consisting of a T cell, a natural killer (NK) cell, NK-92 cell, a cytotoxic T lymphocyte (CTL), and a regulatory T cell.

CARs are molecules generally including an extracellular and intracellular domain. The extracellular domain includes a target-specific binding element. The intracellular domain (e.g., cytoplasmic domain) includes a costimulatory signaling region and a zeta chain portion. The costimulatory signaling region refers to a portion of the CAR including the intracellular domain of a costimulatory molecule. Costimulatory molecules are cell surface molecules other than antigens receptors or their ligands that are required for an efficient response of lymphocytes to antigen.

Between the extracellular domain and the transmembrane domain of the CAR, there may be incorporated a spacer domain. As used herein, the term "spacer domain" generally means any oligo- or polypeptide that functions to link the transmembrane domain to, either the extracellular domain or, the cytoplasmic domain of the polypeptide chain. A spacer domain may include up to 300 amino acids, preferably 10 to 100 amino acids, and most preferably 25 to 50 amino acids.

In some embodiments, the target-specific binding element of the CAR in the present disclosure may recognize a tumor antigen. Tumor antigens are proteins that are produced by tumor cells that elicit an immune response, particularly T-cell mediated immune responses. Tumor antigens are well known in the art and include, for example, a glioma-associated antigen, carcinoembryonic antigen (CEA), (3-human chorionic gonadotropin, alpha-fetoprotein (AFP), lectin-reactive AFP, thyroglobulin, RAGE-1, MN-CA IX, human telomerase reverse transcriptase, RU1, RU2 (AS), intestinal carboxylesterase, mut hsp70-2, M-CSF, prostase, prostate-specific antigen (PSA), PAP, NY-ESO-1, LAGE-1a, p53, prostein, PSMA, Her2/neu, survivin and telomerase, prostate carcinoma tumor antigen-1 (PCTA-1), MAGE, ELF2M, neutrophil elastase, ephrinB2, CD22, insulin growth factor (IGF)-I, IGF-II, IGF-I receptor and mesothelin.

In some embodiments, the tumor antigen includes HER2, CD19, CD20, CD22, Kappa or light chain, CD30, CD33, CD123, CD38, ROR1, ErbB3/4, EGFR, EGFRvIII, EphA2, FAP, carcinoembryonic antigen, EGP2, EGP40, mesothelin, TAG72, PSMA, NKG2D ligands, B7-H6, IL-13 receptor a 2, IL-11 receptor a, MUC1, MUC16, CA9, GD2, GD3, HMW-MAA, CD171, Lewis Y, G250/CAIX, HLA-AI MAGE A1, HLA-A2 NY-ESO-1, PSC1, folate receptor-α, CD44v7/8, 8H9, NCAM, VEGF receptors, 5T4, Fetal AchR, NKG2D ligands, CD44v6, TEM1, TEM8, or viral-associated antigens expressed by the tumor.

In some embodiments, the binding element of the CAR may include any antigen binding moiety that when bound to its cognate antigen, affects a tumor cell such that the tumor cell fails to grow, or is promoted to die or diminish.

In some embodiments, the antigen binding element of the CAR of the disclosure targets an antigen of a non-essential organ. In some instances, the antigen binding element of the CAR of the disclosure includes anti-antigen including the amino acid sequence set forth at least at one of SEQ ID NOs: 2-20 or 44.

In some embodiments, internal ribosome entry sites (IRES) elements are used to create multigene, or polycistronic, or messages. For example, an IRES element may link a nucleic acid sequence encoding CAR and a nucleic acid sequence encoding one of the various antigens (See FIG. 1 and Table 2). In other embodiments, other tools such as 2A may be used to create multigene, or polycistronic, or messages.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The embodiments of the present disclosure further relate to vectors in which a DNA of the present disclosure is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from oncoretroviruses such as murine leukemia viruses in that they can transduce non-proliferating cells, such as hepatocytes. They also have the added advantage of low immunogenicity.

The expression of natural or synthetic nucleic acids encoding CARs is typically achieved by operably linking a nucleic acid encoding the CAR polypeptide or portions thereof to one or more promoters and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

In some embodiments, the antigen binding domain is an antibody, an antigen-binding fragment thereof, or a ligand thereof. For example, the antigen-binding fragment is a Fab or a scFv.

In some embodiments, the antigen is expressed on a non-essential organ cell present in a microenvironment of a tumor.

In some embodiments, the tumor is breast cancer. In certain embodiments, the antigen is a mammary gland antigen. For example, the mammary gland antigen is prolactin receptor (PRLR) having SEQ ID NO: 29.

As used herein, "a mammary gland antigen" refers to an antigen expressed on or by a mammary gland cell. Examples of mammary gland cells include catheter epithelial cells/foam cells.

The prolactin receptor (PRLR) is involved in the growth and differentiation of various cells. Prolactin receptors have been identified in a number of cells and tissues, including the mammary gland, organs of the reproductive system, central nervous system, pituitary, adrenal cortex, skin, bone, lung, heart, liver, pancreas, GI tract, kidney and lymphoid tissues. Human growth hormone (hGH), human prolactin (hPRL) and human placental lactogen (hPL) all specifically bind the prolactin receptor with high affinity.

As used herein, "PRLR" refers to human prolactin receptor. The term should be construed to include not only human prolactin receptor but variants, homologs, fragments and portions thereof to the extent that such variants, homologs, fragments and portions thereof retain the ability of prolactin receptor to bind to antibodies or ligands of human prolactin receptor as disclosed herein.

In some embodiments, the nucleotide sequence encoding at least a portion of the human prolactin receptor is shown in SEQ ID NO: 28 and at least a portion of the human prolactin receptor are shown in SEQ ID NO: 29.

In some embodiments, the present disclosure is particularly well-suited to deliver agents to cells that overexpress the prolactin receptor differentially. As used herein, a prolactin receptor is "overexpressed" when it is present on the surface of a cell (e.g., a mammary gland cell) in an amount that is statistically significantly greater than a suitable control cell (e.g., a brain cell). In some embodiments, the prolactin receptor is present on the cell surface at least about 1.5-fold, 2-fold, 5-fold, 10-fold, 100-fold or 1000-fold greater than a suitable control cell. For example, over 80% of breast tumors overexpress the prolactin receptor by as much as 10- to 1000-fold over normal breast tissue. Accordingly, some embodiments of the present disclosure are particularly suitable for delivery of an agent (e.g., CAR T/NK cells) to breast cancer cells of a subject. In these instances, non-tumor cells that express the prolactin receptor may also be killed by the transferred CAR T/NK cells. However, if the mammary gland is non-essential tissues with respect to the subject, the killing of normal cells of the mammary gland does not cause a life-threatening event (e.g., complications) to the subject.

In some embodiments, the antigen binding domain is prolactin receptor ligand having SEQ ID NO: 20 or 44.

A prolactin receptor ligand, as used herein, refers to an entity that binds the prolactin receptor, regardless of whether downstream biological effects of prolactin receptor binding are observed. As will be appreciated, no particular level of binding specificity is required, and acceptable levels of specificity will depend on the application. Suitable prolactin receptor ligands include human placental lactogen and variants thereof (including truncated or modified forms), prolactin and variants thereof (including truncated or modified forms) and human growth hormone (hGH) (including truncated or modified forms). Selection of a suitable prolactin receptor ligand will depend on, e.g., the agent to be delivered, the coupling strategy to be used, and the degree of receptor activation desired, if any.

In some embodiments, at least a portion of prolactin receptor ligand is shown in SEQ ID NO: 20 or 44.

In some embodiments, the tumor is colorectal cancer. In certain embodiments, the antigen is a colon antigen. For example, the colon antigen is Guanylate cyclase 2C (GUCY2C) having SEQ ID NO: 33.

As used herein, "a colon antigen" refers to an antigen expressed on or by a colon cell. Examples of colon cells include goblet cells and enterocytes.

Guanylyl cyclase 2C (GUCY2C) is principally expressed in intestinal epithelial cells. GUCY2C is the receptor for diarrheagenic bacterial enterotoxins (STs) and the gut paracrine hormones, guanylin, and uroguanylin. These ligands regulate water and electrolyte transport in the intestinal and renal epithelia and are ultimately responsible for acute secretory diarrhea.

As used herein, "GUCY2C" refers to human Guanylyl cyclase 2C. The term should be construed to include not only human Guanylyl cyclase 2C, but variants, homologs, fragments and portions thereof to the extent that such variants, homologs, fragments and portions thereof retain the ability of Guanylyl cyclase 2C to bind to antibodies or ligands of human Guanylyl cyclase 2C as disclosed herein.

In some embodiments, the nucleotide sequence encoding at least a portion of GUCY2C is shown in SEQ ID NO: 32 and the amino acid sequence of at least a portion of GUCY2C are shown in SEQ ID NO: 33.

In some embodiments, the present disclosure is particularly well-suited to deliver agents to cells that overexpress the GUCY2C differentially. As used herein, a GUCY2C is "overexpressed" when it is present on the surface of a cell (e.g., a colon cell) in an amount that is statistically significantly greater than a suitable control cell (e.g., a brain cell and a pancreas cell). In some embodiments, the GUCY2C is present on the cell surface at least about 1.5-fold, 2-fold, 5-fold, 10-fold, 100-fold or 1000-fold greater than a suitable control cell. Accordingly, some embodiments of the present disclosure are particularly suitable for delivery of an agent (e.g., CAR T/NK cells) to colorectal cancer cells. In these instances, non-tumor cells that express the GUCY2C may also be killed by the transferred CAR T/NK cells. However, if the colon is non-essential tissues with respect to the subject, the killing of normal cells of the colon does not cause a life-threatening event (e.g., complications) to the subject.

In some embodiments, the tumor is gastric cancer. In certain embodiments, the antigen is a gastric gland antigen. For example, the gastric gland antigen is Mucin 17 (Muc17) having SEQ ID NO: 31.

As used herein, "a gastric gland antigen" refers to an antigen expressed on or by a gastric gland cell. Examples of gastric gland cells include gastric parietal cells, mucous cells, and surface epithelial cells.

Muc17 is a type 1 membrane protein comprising 4,493 amino acids. Muc17 belongs to the membrane-form mucin family, and most part of its extracellular domain comprises a tandem repeat of a serine-, threonine-, and proline-rich 59-mer sequence and is glycosylated.

As used herein, "Muc17" refers to human Mucin 17. The term should be construed to include not only human Mucin 17 but variants, homologs, fragments and portions thereof to the extent that such variants, homologs, fragments and portions thereof retain the ability of Mucin 17 to bind to antibodies or ligands of human Mucin 17 as disclosed herein.

In some embodiments, the nucleotide sequence encoding at least a portion of Muc17 is shown in SEQ ID NO: 30 and the amino acid sequence of at least a portion of Muc17 are shown in SEQ ID NO: 31.

In some embodiments, the present disclosure is particularly well-suited to deliver agents to cells that overexpress the Muc17 differentially. As used herein, a Muc17 is "overexpressed" when it is present on the surface of a cell (e.g., a gastric gland cell) in an amount that is statistically significantly greater than a suitable control cell (e.g., a brain cell and a pancreas cell). In some embodiments, the Muc17 is present on the cell surface at least about 1.5-fold, 2-fold, 5-fold, 10-fold, 100-fold or 1000-fold greater than a suitable control cell. Accordingly, some embodiments of the present disclosure are particularly suitable for delivery of an agent to gastric cancer cells. In these instances, non-tumor cells that express the Muc17 may also be killed by the transferred CAR T/NK cells. However, if the gastric gland is non-essential tissues with respect to the subject, the killing of normal cells of the colon does not cause a life-threatening event (e.g., complications) to the subject.

In some embodiments, the tumor is bladder cancer. In certain embodiments, the antigen is a bladder antigen. For example, the bladder antigen is CD207 having SEQ ID NO: 35.

As used herein, "a bladder antigen" refers to an antigen expressed on or by a bladder cell. Examples of bladder cells include transitional cells and mucosal epithelial cells.

CD207 (langerin or Cluster of Differentiation 207) is a protein which in humans is encoded by the CD207 gene. CD207 is a type II transmembrane, C-type lectin receptor on Langerhans cells. CD207 is localized in the Birbeck granules, organelles present in the cytoplasm of Langerhans cells and including superimposed and zippered membranes.

As used herein, "CD207" refers to human CD207. The term should be construed to include not only human CD207 but variants, homologs, fragments and portions thereof to the extent that such variants, homologs, fragments and portions thereof retain the ability of human CD207 to bind to antibodies or ligands of human CD207 as disclosed herein.

In some embodiments, the nucleotide sequence encoding at least a portion of the human CD207 is shown in SEQ ID NO: 34 and the amino acid sequence of at least a portion of the human CD207 are shown in SEQ ID NO: 35.

In some embodiments, the present disclosure is particularly well-suited to deliver agents to cells that overexpress the CD207 differentially. As used herein, a CD207 is "overexpressed" when it is present on the surface of a cell (e.g., a bladder cell) in an amount that is statistically significantly greater than a suitable control cell (e.g., an endocrine tissue cell). In some embodiments, the CD207 is present on the cell surface at least about 1.5-fold, 2-fold, 5-fold, 10-fold, 100-fold or 1000-fold greater than a suitable control cell. Accordingly, some embodiments of the present disclosure are particularly suitable for delivery of an agent to bladder cancer cells. In these instances, non-tumor cells that express the CD207 may also be killed by the transferred CAR T/NK cells. However, if the bladder is non-essential tissues with respect to the subject, the killing of normal cells of the colon does not cause a life-threatening event (e.g., complications) to the subject.

In some embodiments, the tumor is an ovary tumor. In certain embodiments, the antigen is an ovary antigen. For example, the ovary antigen is Frizzled family receptor 10 (FZD10) having SEQ ID NO: 25.

As used herein, "an ovary antigen" refers to an antigen expressed on or by an ovary cell. Examples of ovary cells include follicular cells, granulosa cells, and germinal epithelium.

A human Fz gene family member, Frizzled-10 (FZD10), has been cloned and characterized. Analysis of the FZD10 nucleotide sequence showed that the human FZD10 gene encodes a seven-transmembrane-receptor of 581 amino acids, including an amino-terminal cysteine-rich domain and a carboxy-terminal Ser/Thr-Xxx-Val motif. FZD10-encoding mRNA (4.0 kb) was detected in placenta, fetal kidney, fetal lung, and brain. In adult brain, FZD10 mRNA was abundant in the cerebellum. The FZD10 gene was mapped to human chromosome 12q24.33. FZD10 shares 65.7% amino-acid identity with Frizzled-9 (FZD9). FZD10 and FZD9 constitute a subfamily of the Frizzled genes. FZD10 is the receptor for the Wnt ligand proteins WNT7a and WNT7b. There is 93% identity between mouse and human FZD10.

As used herein, "FZD10" refers to human FZD10. The term should be construed to include not only human FZD10 but variants, homologs, fragments and portions thereof to the extent that such variants, homologs, fragments and portions thereof retain the ability of human FZD10 to bind to antibodies or ligands of human FZD10 as disclosed herein.

In some embodiments, the nucleotide sequence encoding at least a portion of the human FZD10 is shown in SEQ ID NO: 24 and the amino acid sequence of at least a portion of the human FZD10 are shown in SEQ ID NO: 25.

In some embodiments, the present disclosure is particularly well-suited to deliver agents to cells that overexpress the FZD10 differentially. As used herein, an FZD10 is "overexpressed" when it is present on the surface of a cell (e.g., an ovary cell) in an amount that is statistically significantly greater than a suitable control cell (e.g., an endocrine tissue cell). In some embodiments, the FZD10 is present on the cell surface at least about 1.5-fold, 2-fold, 5-fold, 10-fold, 100-fold or 1000-fold greater than a suitable control cell. Accordingly, some embodiments of the present disclosure are particularly suitable for delivery of an agent to ovary cancer cells. In these instances, non-tumor cells that express the FZD10 may also be killed by the transferred CAR T/NK cells. However, if the ovary is non-essential tissues with respect to the subject, the killing of normal cells of the colon does not cause a life-threatening event (e.g., complications) to the subject.

In some embodiments, the tumor is a thyroid tumor. In certain embodiments, the antigen is a thyroid antigen. For example, the thyroid antigen is Thyroid stimulating hormone receptor (TSHR) having SEQ ID NO: 27.

As used herein, "a thyroid antigen" refers to an antigen expressed on or by a thyroid cell. Examples of thyroid cells include follicular cells and parafollicular cells.

A human TSHR is a receptor for thyroid-stimulating hormone (TSH) which is present on the thyroid membrane. When TSH secreted from the pituitary gland binds to TSHR on the thyroid follicle cell membrane, the thyroid gland secretes T3 and T4 having metabolic functions. TSHR is a seven-transmembrane receptor having a molecular weight of about 95,000 to 100,000. It was reported that the human thyrotropin receptor (TSHR) includes three domains: a leucine-rich domain (LRD; amino acids 36-281), a cleavage domain (CD; amino acids 282-409), and transmembrane domain (TMD; amino acids 410-699). Human thyrotropin (hTSH) a chains were found to make contact with many amino acids on the LRD surface and CD surface.

As used herein, "TSHR" refers to human thyroid stimulating hormone receptor. The term should be construed to include not only human thyroid stimulating hormone receptor, but variants, homologs, fragments and portions thereof to the extent that such variants, homologs, fragments and portions thereof retain the ability of human thyroid stimulating hormone receptor to bind to antibodies or ligands of human thyroid stimulating hormone receptor as disclosed herein.

In some embodiments, the nucleotide sequence encoding at least a portion of the human thyroid stimulating hormone receptor is shown in SEQ ID NO: 26 and the amino acid sequence of at least a portion of the human thyroid stimulating hormone receptor are shown in SEQ ID NO: 27.

In some embodiments, the present disclosure is particularly well-suited to deliver agents to cells that overexpress the TSHR differentially. As used herein, a TSHR is "overexpressed" when it is present on the surface of a cell (e.g., a thyroid cell) in an amount that is statistically significantly greater than a suitable control cell (e.g., a brain cell or a pancreas cell). In some embodiments, the TSHR is present on the cell surface at least about 1.5-fold, 2-fold, 5-fold, 10-fold, 100-fold or 1000-fold greater than a suitable control cell. Accordingly, some embodiments of the present disclosure are particularly suitable for delivery of an agent to thyroid cancer cells. In these instances, non-tumor cells that express the TSHR may also be killed by the transferred CAR T/NK cells. However, if the thyroid is non-essential tissues with respect to the subject, the killing of normal cells of the colon does not cause a life-threatening event (e.g., complications) to the subject.

In some embodiments, the costimulatory signaling region may include the intracellular domain of a costimulatory molecule selected from the group consisting of CD27, CD28, 41-BB, OX40, CD30, CD40, PD-1, ICOS, lymphocyte function-associated antigen-1 (LFA-1), CD2, CD7, LIGHT, NKG2C, B7-H3, a ligand that specifically binds with CD83, and any combination thereof.

In some embodiments, the antigen binding domain may include at least one of SEQ ID NOs: 2-20 or 44.

In some embodiments, the antigen binding domain may include SEQ ID NO: 3 or 4, or a combination thereof, and the tumor is ovary tumor.

In some embodiments, the antigen binding domain may include SEQ ID NO: 6 or 7, or a combination thereof, and the tumor is thyroid tumor.

In some embodiments, the antigen binding domain may include SEQ ID NO: 9 or 10, or a combination thereof, and the tumor is breast cancer.

In some embodiments, the antigen binding domain may include SEQ ID NO: 12 or 13, or a combination thereof, and the tumor is gastric cancer.

In some embodiments, the antigen binding domain may include SEQ ID NO: 15 or 16, or a combination thereof, and the tumor is colorectal cancer.

In some embodiments, the antigen binding domain may include SEQ ID NO: 18 or 19, or a combination thereof, and the tumor is bladder cancer.

In some embodiments, the antigen binding domain may include SEQ ID NO: 20 or 44, and the tumor is breast cancer.

Some embodiments of the present disclosure relate to a method of selecting an antigen binding domain for a CAR for treating a subject with tumor cells. The method may include determining an organ of cells from that the tumor cells derived, determining that the organ is a non-essential organ with respect to the subject, searching a database to identify multiple markers that are expressed in a cell population of the organ, selecting a marker of the multiple markers based on a predetermined condition, and generating cells comprising a CAR using cells from the subject. The CAR may include an antigen binding domain, a transmembrane domain, a costimulatory signaling region, and a CD3 zeta signaling domain, and the antigen binding domain may bind to the marker. Examples of an organ include mammary gland, gastric gland, etc. In certain embodiments, the organ does not include a blood tissue.

In some embodiments, the predetermined condition may include the marker is present on the cell surface of a cell from that tumor cells are derived at least about at least one of 1.5-fold, 2-fold, 5-fold, 10-fold, 100-fold or 1000-fold greater than a suitable control cell, and the organ is non-essential such that an injury to the organ does not produce death of the subject.

In some embodiments, the non-essential organ is a mammary gland, and the marker is PRLR.

In some embodiments, the non-essential organ is a colon, and the marker is GUCY2C.

In some embodiments, the non-essential organ is a gastric gland, and the marker is Muc17.

In some embodiments, the non-essential organ is a bladder, and the marker is CD207.

In some embodiments, the non-essential organ is an ovary, and the marker is FZD10.

In some embodiments, the non-essential organ is thyroid, and the marker is TSHR.

In some embodiments, the tumor is selected from a group consisting of breast cancer, a thyroid tumor, colorectal cancer, an ovary tumor, bladder cancer, and is bladder cancer.

Some embodiments of the present disclosure relate to a modified cell including a nucleic acid sequence encoding a CAR having one of SEQ ID NOs: 36-42. For example, the cell is selected from the group consisting of a T cell, a natural killer (NK) cell, a cytotoxic T lymphocyte (CTL), and a regulatory T cell.

In some embodiments, the CAR has SEQ ID NO: 38, and an antigen binding domain of the CAR binds to prolactin receptor ligand having SEQ ID NO: 20 or 44.

In some embodiments, the CAR has SEQ ID NO: 40, and an antigen binding domain of the CAR binds to GUCY2C having SEQ ID NO: 33.

In some embodiments, the CAR has SEQ ID NO: 39, and an antigen binding domain of the CAR binds to Muc17 having SEQ ID NO: 31.

In some embodiments, the CAR has SEQ ID NO: 41, and an antigen binding domain of the CAR binds to CD207 having SEQ ID NO: 35.

In some embodiments, the CAR has SEQ ID NO: 36, and an antigen binding domain of the CAR binds to FZD10 having SEQ ID NO: 25.

In some embodiments, the CAR has SEQ ID NO: 37, and an antigen binding domain of the CAR binds to TSHR having SEQ ID NO: 27.

Additional information related to expression synthetic nucleic acids encoding CARs and gene transfer into mammalian cells is provided in U.S. Pat. No. 8,906,682, incorporated by reference in its entirety.

The embodiments further relate to methods for treating a patient for illness including administering to the patient an effective amount of the engineered cells of the present disclosure. Various illnesses can be treated according to the present methods including cancer, such as ovarian carcinoma, breast carcinoma, colon carcinoma, glioblastoma multiforme, prostate carcinoma and leukemia. In some embodiments, the method includes administering to a human patient a pharmaceutical composition including an effective antitumor amount of a population of human T cells, wherein the human T cells of the population include human T-cells that comprise the nucleic acid sequence as described in the present disclosure.

Cancers that may be treated include tumors that are not vascularized, or not yet substantially vascularized, as well as vascularized tumors. The cancers may include non-solid tumors (such as hematological tumors, for example, leukemias and lymphomas) or may include solid tumors. Types of cancers to be treated with the CARs of the disclosure include, but are not limited to, carcinoma, blastoma, and sarcoma, and certain leukemia or lymphoid malignancies, benign and malignant tumors, and malignancies, e.g., sarcomas, carcinomas, and melanomas. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brain stem glioma and mixed gliomas), glioblastoma (also known as glioblastoma multiforme) astrocytoma, CNS lymphoma, germinoma, medulloblastoma, Schwannoma craniopharyngioma, ependymoma, pinealoma, hemangioblastoma, acoustic neuroma, oligodendroglioma, meningioma, neuroblastoma, retinoblastoma and brain metastases).

Generally, the cells activated and expanded as described herein may be utilized in the treatment and prevention of diseases that arise in individuals who are immunocompromised. In particular, the engineered cells of the present disclosure are used in the treatment of cancer. In certain embodiments, the cells of the present disclosure are used in the treatment of patients at risk of developing cancer. Thus, the present disclosure provides methods for the treatment or prevention of cancer comprising administering to a subject in need thereof, a therapeutically effective amount of the engineered T cells of the present disclosure.

The engineered T cells of the present disclosure may be administered either alone or as a pharmaceutical composition in combination with diluents and/or with other components such as IL-2 or other cytokines or cell populations. Briefly, pharmaceutical compositions of the present disclosure may include a target cell population as described herein, in combination with one or more pharmaceutically or physiologically acceptable carriers, diluents or excipients. Such compositions may include buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present disclosure are preferably formulated for intravenous administration.

Pharmaceutical compositions of the present disclosure may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an antitumor effective amount", "a tumor-inhibiting effective amount", or "therapeutic amount" is indicated, the precise amount of the compositions of the present disclosure to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regimen for a particular patient can readily be determined by one skilled in the art of medicine by monitoring the patient for signs of disease and adjusting the treatment accordingly.

In certain embodiments, it may be desired to administer activated T cells to a subject and then subsequently redraw blood (or have apheresis performed), activate T cells therefrom according to the present disclosure, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocols, may select out certain populations of T cells.

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodal, intramedullary, intramuscularly, by intravenous (i. v.) injection, or intraperitoneally. In one embodiment, the T cell compositions of the present disclosure are administered to a patient by intradermal or subcutaneous injection. In another embodiment, the T cell compositions of the present disclosure are preferably administered by i.v. injection. The compositions of T cells may be injected directly into a tumor, lymph node, or site of infection.

In certain embodiments of the present disclosure, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the present disclosure may be used in combination with chemotherapy, radiation, immunosuppressive agents, such as cyclosporin, azathioprine, methotrexate, mycophenolate, and FK506, antibodies, or other immunoablation agents such as CAM PATH, anti-CD3 antibodies or other antibody therapies, Cytoxan, fludarabine, cyclosporine, FK506, rapamycin, mycophenolic acid, steroids, FR901228, cytokines, and irradiation. These drugs inhibit either the calcium-dependent phosphatase calcineurin (cyclosporine and FK506) or inhibit the p7056 kinase that is important for growth factor-induced signaling (rapamycin). (Liu et al., Cell 66:807-815, 1991; Henderson et al., Immun 73:316-321, 1991; Bierer et al., Curr. Opin. Immun 5:763-773, 1993; Isoniemi (supra)). In a further embodiment, the cell compositions of the present disclosure are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present disclosure are administered following B-cell ablative therapy such as agents that react with CD20, e.g., Rituxan. For example, in one embodiment, subjects may undergo standard treatment with high-dose chemotherapy followed by peripheral blood stem cell transplantation. In certain embodiments, following the transplant, subjects receive an infusion of the expanded immune cells of the present disclosure. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period of 1 and 30 days. The preferred daily dose is 1 to 10 mg per day although in some instances larger doses of up to 40 mg per day may be used (described in U.S. Pat. No. 6,120,766, incorporated by reference in its entirety).

Additional information on the methods of cancer treatment using engineer T cells is provided in U.S. Pat. No. 8,906,682, incorporated by reference in its entirety.

Some embodiments of the present disclosure relate to a nucleic acid sequence encoding a CAR. For example, the CAR includes an antigen binding domain, a transmembrane domain, and an intracellular domain. The antigen binding domain binds to an organ lineage antigen, and the organ lineage antigen is expressed in a tumor and normal tissue from which the tumor is derived.

The terms "tumor-associated antigens" as used herein refer to antigens selectively expressed or overexpressed by malignant cells as compared with normal adult tissue. The tumor-associated antigens include various groups such as tumor-specific antigens, oncofetal antigens, oncogene products, organ lineage antigens, viral antigens, etc. For example, oncogene and suppressor gene products, such as nonmutated HER-2/neu and p53, are analogous to oncofetal antigens in that they can be overexpressed in tumors and may be expressed in some fetal tissues.

The term "tumor-specific antigens" as used herein refers to antigens that are uniquely expressed in tumors, such as point-mutated ras oncogenes, p53 mutations, anti-idiotype antibodies (Abs), and products of ribonucleic acid (RNA) splice variants and gene translocations.

The term "organ lineage antigen" as used herein is defined an antigen expressed in a tumor of a given type and the normal organ from which the tumor is derived. Examples of organ lineage antigen include prostate-specific antigen (PSA) and the melanocyte antigens, such as MART-1/Melan A, tyrosinase, gp100, and TRP-1/gp75. Organ lineage antigens may be targets for immunotherapy if the normal organ in which they are expressed is not essential, such as the prostate, breast, or melanocyte. As used herein, an organ refers to an integrated group of cells with a common structure, an intercellular material, and/or a function.

Some embodiments of the present disclosure relate to a vector including the nucleic acid sequence. In some embodiments, the vector is an expression vector.

Some embodiments of the present disclosure relate to a pharmaceutical composition comprising an effective antitumor amount of a population of human T or NK cells. The human T or NK cells of the population include human T or NK cells that include the nucleic acid sequence as described above.

Some embodiments of the present disclosure relate to a method of treating the tumor in a human patient, the method comprising administering to the human patient the pharmaceutical composition as described above.

In some embodiments, the tumor is a breast tumor, and the organ lineage antigen comprises PRLR.

In some embodiments, the tumor is a colorectal tumor, and the organ lineage antigen comprises at least one of CLCA1, MUC12, GUCY2C, or GPR35.

In some embodiments, the tumor is a gastric tumor, and the organ lineage antigen comprises CR1L and/or MUC17.

In some embodiments, the tumor is an esophageal tumor, and the organ lineage antigen comprises at least one of TMPRSS11B, MUC21, or TMPRSS11E.

In some embodiments, the tumor is a bladder carcinoma, and the organ lineage antigen comprises CD207.

In some embodiments, the tumor is a pancreatic tumor, and the organ lineage antigen comprises SLC30A8 and/or CFC1.

In some embodiments, the tumor is a cervical tumor, and the organ lineage antigen comprises SLC12A3 and/or SSTR1.

In some embodiments, the tumor is an ovary tumor, and the organ lineage antigen comprises GPR27 and/or FZD10.

In some embodiments, the tumor is a thyroid tumor, and the organ lineage antigen comprises TSHR.

Some embodiments relate to a pharmaceutical composition comprising human T cells. The human T cells may include a nucleic acid sequence encoding a CAR (CAR), the CAR comprises an antigen binding domain, a transmembrane domain, a costimulatory signaling region, and a CD3 zeta signaling domain. The antigen binding domain may include one of the amino acid sequences of SEQ ID NOs: 2, 5, 8, 11, 14, 17, or 20.

In some embodiments, the antigen binding domain comprises the amino acid sequence of SEQ ID NO: 2 and binds to Frizzled family receptor 10 (FZD10).

In some embodiments, the antigen binding domain comprises the amino acid sequence of SEQ ID NO: 5 and binds to Thyroid stimulating hormone receptor (TSHR).

In some embodiments, the CAR comprises the amino acid sequence of SEQ ID NO: 8 and binds to prolactin receptor (PRLR).

In some embodiments, the antigen binding domain comprises the amino acid sequence of SEQ ID NO: 11 and binds to Mucin 17 (Muc17).

In some embodiments, the antigen binding domain comprises the amino acid sequence of SEQ ID NO: 14 and binds to Guanylate cyclase 2C (GUCY2C).

In some embodiments, the antigen binding domain comprises the amino acid sequence of SEQ ID NO: 17 and binds to Langerin or Cluster of Differentiation 207 (CD207).

In some embodiments, the antigen binding domain comprises the amino acid sequence of SEQ ID NO: 20 and binds to PRLR.

In some embodiments, the CAR comprises the amino acid sequence of SEQ ID NO: 42 and binds to PRLR.

In some embodiments, the CAR comprises at least one of the amino acid sequences of SEQ ID NO: 36-42.

Some embodiments relate to a method for stimulating a T cell-mediated immune response to a cell population expressing an antigen. The method may include contacting the cell population with an effective amount of human T cells comprising a nucleic acid sequence encoding a CAR (CAR). The CAR may include an antigen binding domain, a transmembrane domain, a costimulatory signaling region, and a CD3 zeta signaling domain. The antigen binding domain may include one of the amino acid sequences of SEQ ID NOs: 2, 5, 8, 11, 14, 17, or 20.

In some embodiments, the antigen binding domain comprises the amino acid sequence of SEQ ID NO: 2, and the antigen is FZD10.

In some embodiments, the antigen binding domain comprises the amino acid sequence of SEQ ID NO: 5, and the antigen is TSHR.

In some embodiments, the CAR comprises the amino acid sequence of SEQ ID NO: 8, and the antigen is PRLR.

In some embodiments, the antigen binding domain comprises the amino acid sequence of SEQ ID NO: 11, and the antigen is Muc17.

In some embodiments, the antigen binding domain comprises the amino acid sequence of SEQ ID NO: 14, and the antigen is GUCY2C.

In some embodiments, the antigen binding domain comprises the amino acid sequence of SEQ ID NO: 17, and the antigen is CD207.

In some embodiments, the antigen binding domain comprises the amino acid sequence of SEQ ID NO: 20, and the antigen is PRLR.

In some embodiments, the CAR comprises the amino acid sequence of SEQ ID NO: 42, and the antigen is PRLR.

In some embodiments, the CAR comprises at least one of the amino acid sequences of SEQ ID NO: 36-42.

Some embodiments relate to a method for providing an anti-tumor immune response in a subject. For example, the method relates to stimulating (i.e., eliciting) an anti-tumor immune response in a subject. The method may comprise administrating to the subject an effective amount of a pharmaceutical composition comprising a population of human T cell comprising a nucleic acid sequence encoding a CAR (CAR). The CAR may comprise an antigen binding domain, a transmembrane domain, a costimulatory signaling region, and a CD3 zeta signaling domain. The antigen binding domain binds to a mark of non-essential tissues (e.g., a prolactin receptor).

In some embodiments, the anti-tumor immune response elicited by the CAR T cells may be an active or a passive immune response. In certain embodiments, the CAR T cells mediated immune response may be part of an adoptive immunotherapy approach in which CAR T cells induce an immune response specific to the antigen binding domain in the CAR. For example, T cells that express an anti-PRLR CAR elicits an immune response specific against cells expressing prolactin receptors. In some embodiments, the anti-tumor immune response comprises a reduction in tumor burden on the subject with the tumor (e.g., breast cancer).

In some embodiments, the antigen binding domain is an antibody, a ligand, or an antigen-binding fragment thereof.

In some embodiments, the antigen-binding fragment is a Fab or a scFv.

In some embodiments, antigen binding domain comprises amino acid sequences of SEQ ID NOs: 8.

In some embodiments, the CAR comprises an amino acid sequence of SEQ ID NO: 42.

In some embodiments, the costimulatory signaling region comprises the intracellular domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds with CD83, and any combination thereof.

Table 1 below lists multiple tumor and organ lineage antigens as well as corresponding genes.

| Cancer types | Gene | Gene Abbreviation | Corresponding Protein/antigen |
|---|---|---|---|
| Breast Cancer | Prolactin receptor | PRLR | PRLR |
| colorectal Cancer | Chloride channel accessory 1 | CLCA1 | CLCA1 |
| colorectal Cancer | Mucin 12 | MUC12 | MUC12 |
| colorectal Cancer | Guanylate cyclase 2C | GUCY2C | GUCY2C |
| colorectal Cancer | G protein-coupled receptor 35 | GPR35 | GPR35 |
| Gastric Cancer | Complement component (3b/4b) receptor 1-like | CR1L | CR1L |
| Gastric Cancer | Mucin 17, cell surface associated | MUC17 | MUC17 |
| esophageal Cancer | Transmembrane protease, serine 11B | TMPRSS11B | TMPRSS11B |
| esophageal Cancer | Mucin 21 | MUC21 | MUC21 |
| esophageal Cancer | Transmembrane protease, serine 11E | TMPRSS11E | TMPRSS11E |
| bladder Cancer | CD207 | CD207 | CD207 |
| pancreatic Cancer | Solute carrier family 30 (zinc transporter), member 8 | SLC30A8 | SLC30A8 |
| pancreatic Cancer | Cripto, FRL- 1, cryptic family 1 | CFC1 | CFC1 |
| Cervical Cancer | Solute carrier family 12 (sodium/chloride transporters) member 3 | SLC12A3 | SLC12A3 |
| Cervical tumor | Somatostatin receptor 1 | SSTR1 | SSTR1 |
| Ovary tumor | G protein-coupled receptor 27 | GPR27 | GPR27 |
| Ovary tumor | Frizzled family receptor 10 | FZD10 | FZD10 |
| Thyroid Tumor | Thyroid stimulating hormone receptor | TSHR | TSHR |

EXAMPLES

The present disclosure is further described with reference to the following examples. These examples are provided for purposes of illustration only and are not intended to be limiting unless otherwise specified. Thus, the present disclosure should in no way be construed as being limited to the following examples, but rather, should be construed to encompass any and all variations which become evident as a result of the teaching provided herein.

Construction of Antigen-Expressed K562 Cell Lines

K562 cells were transduced with lentivirus including nucleic acid sequences encoding various antigens (FIG. 1) to establish target tumor cell lines. The lentivirus included the IRES-mCherry (red) construct, which encodes red fluorescence for confirmation of antigen expression. Red fluorescent signals were observed from these cell lines, indicating that target solid tumor cell lines were successfully established (FIG. 2). Techniques of construction of cell lines may be found at "Chimeric Receptors Containing CD137 Signal Transduction Domains Mediate Enhanced Survival of T Cells and Increased Antileukemic Efficacy In Vivo Molecular Therapy vol. 17 no. 8, 1453-1464 August 2009," which is incorporated herein by reference. K562 cells were obtained from American Type Culture Collection (ATCC).

Construction of CAR T Cells

Figure 3:
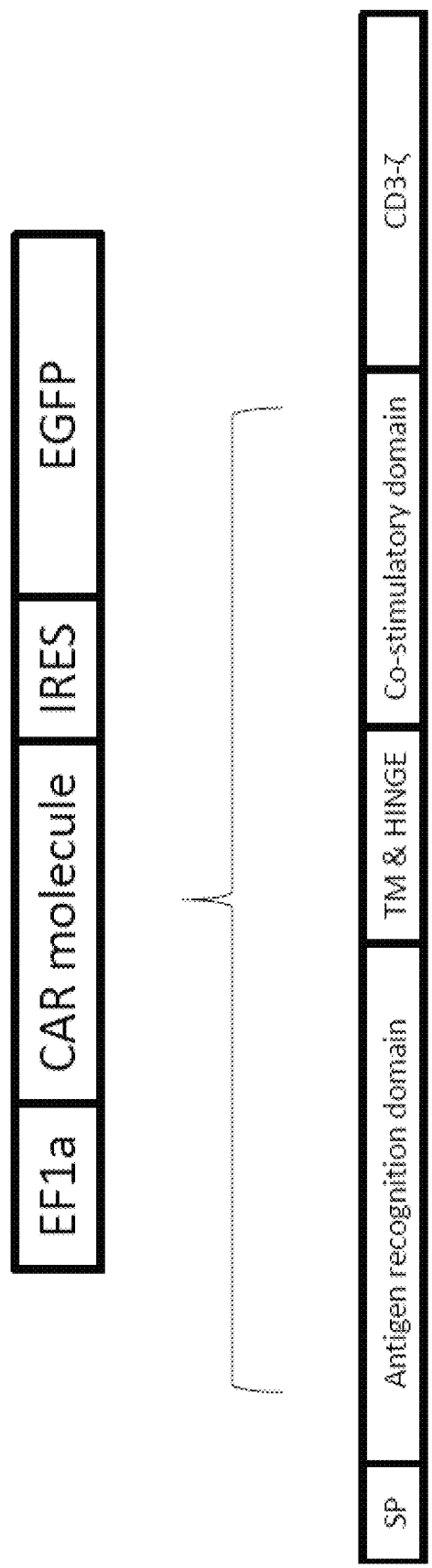
FIG. 3 includes schematic diagrams illustrating the construction of CARs.
Figure 4:
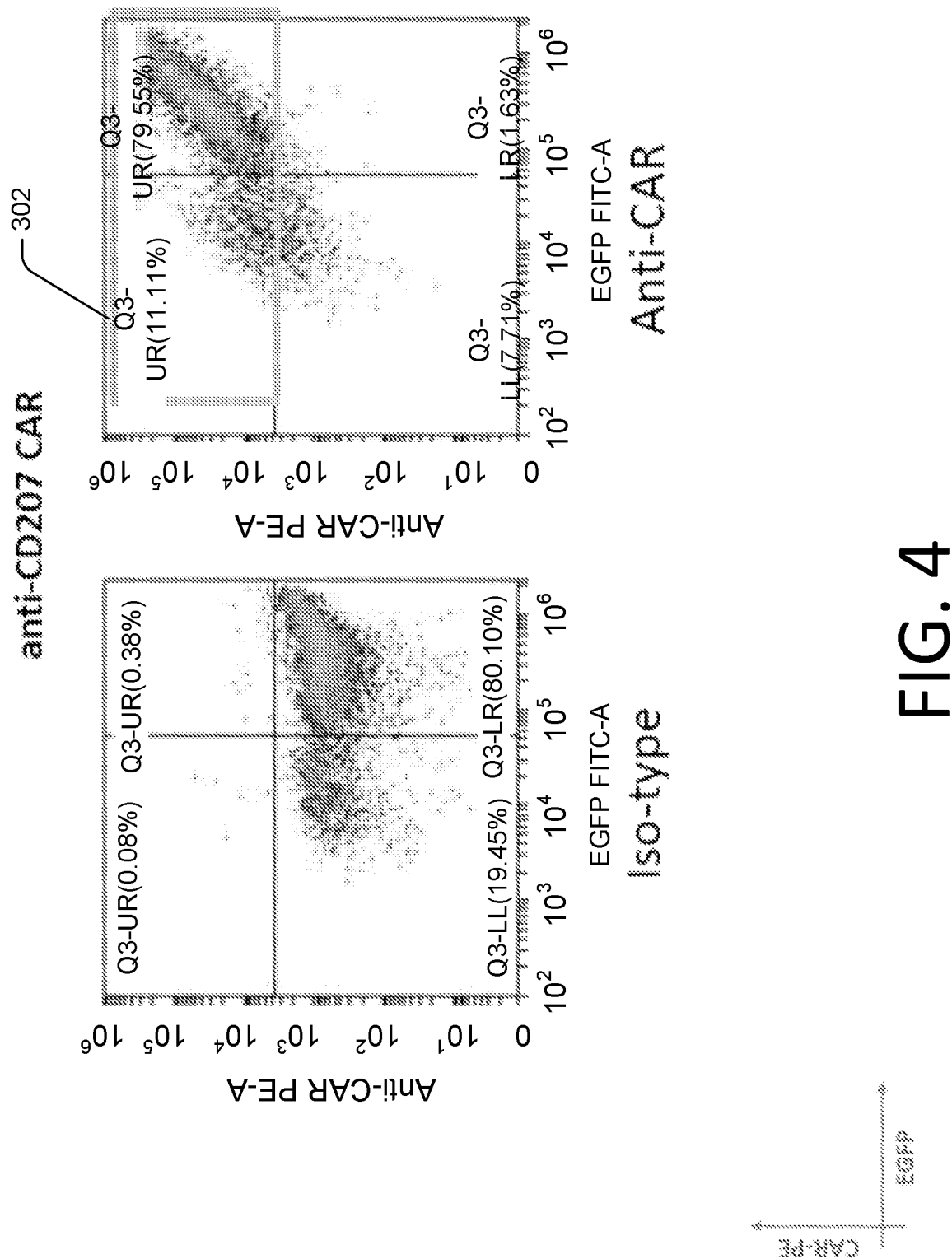
FIG. 4 shows assay results demonstrating that anti-CD207 CAR T cell lines were established.
Figure 5:
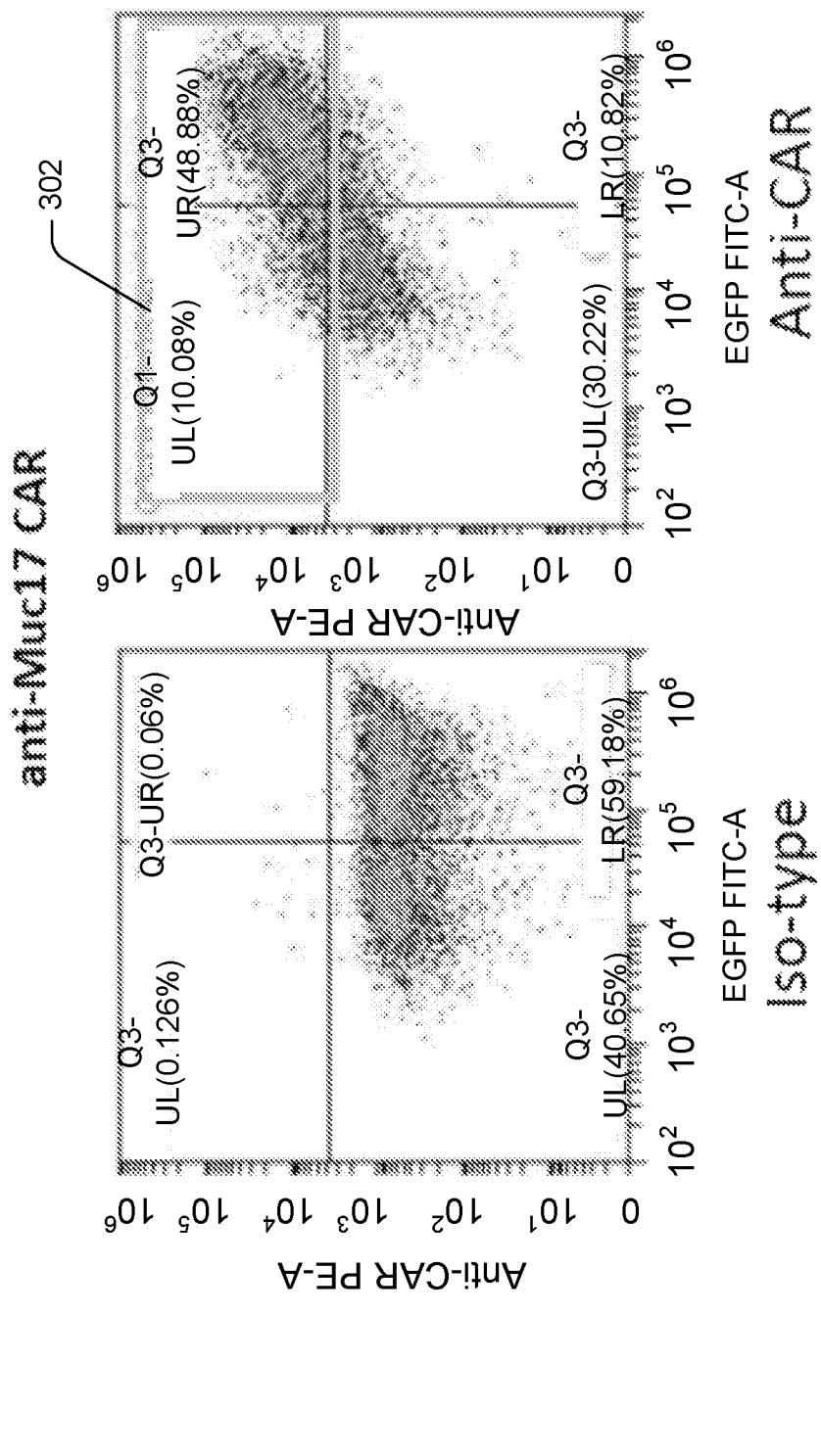
FIG. 5 shows assay results demonstrating that anti-Muc17 CAR T cell lines were established.
Figure 6:
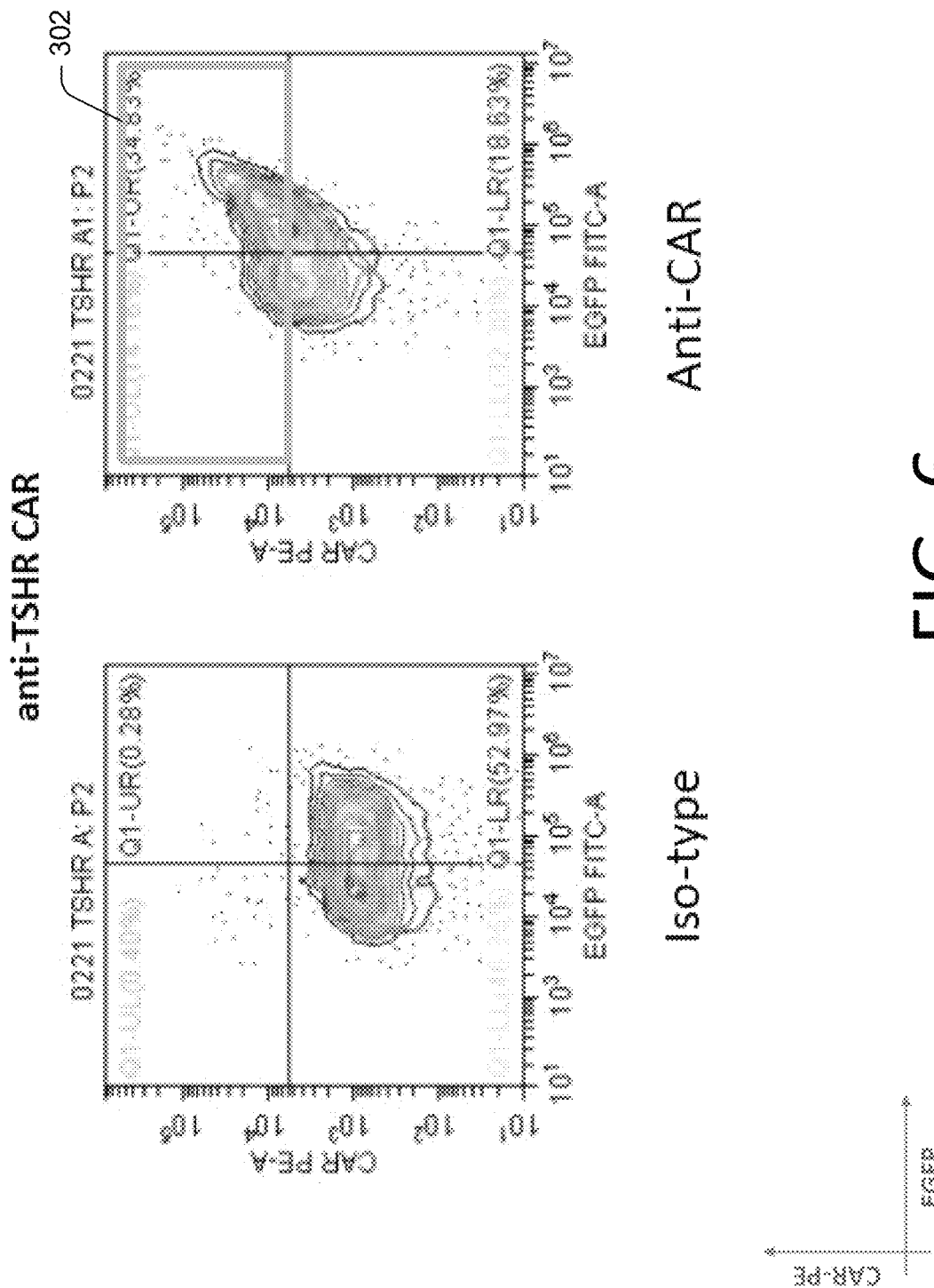
FIG. 6 shows assay results demonstrating that anti-TSHR CAR T cell lines were established.
Figure 7:
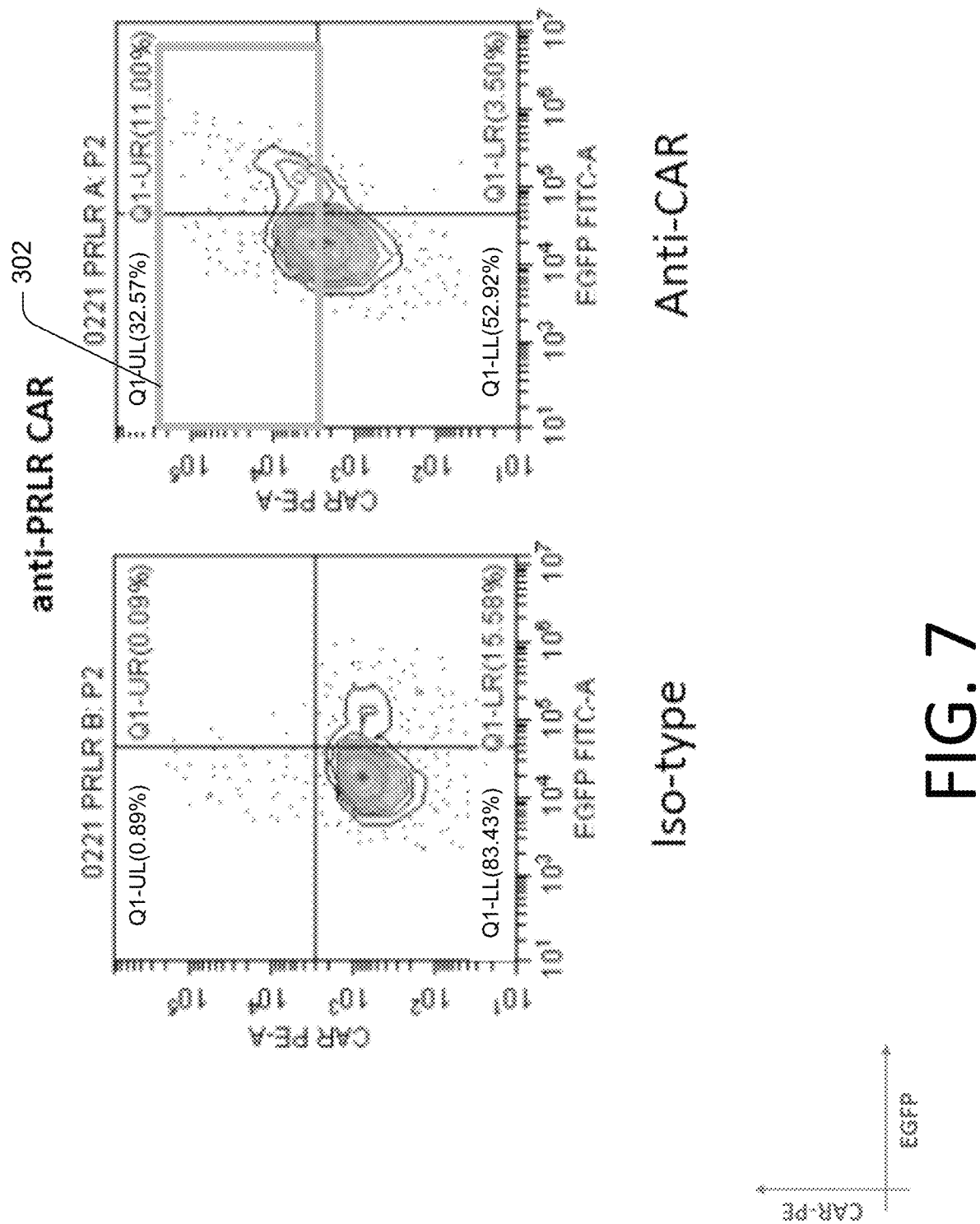
FIG. 7 shows assay results demonstrating that anti-PRLR CAR T cell lines were established.
Figure 8:
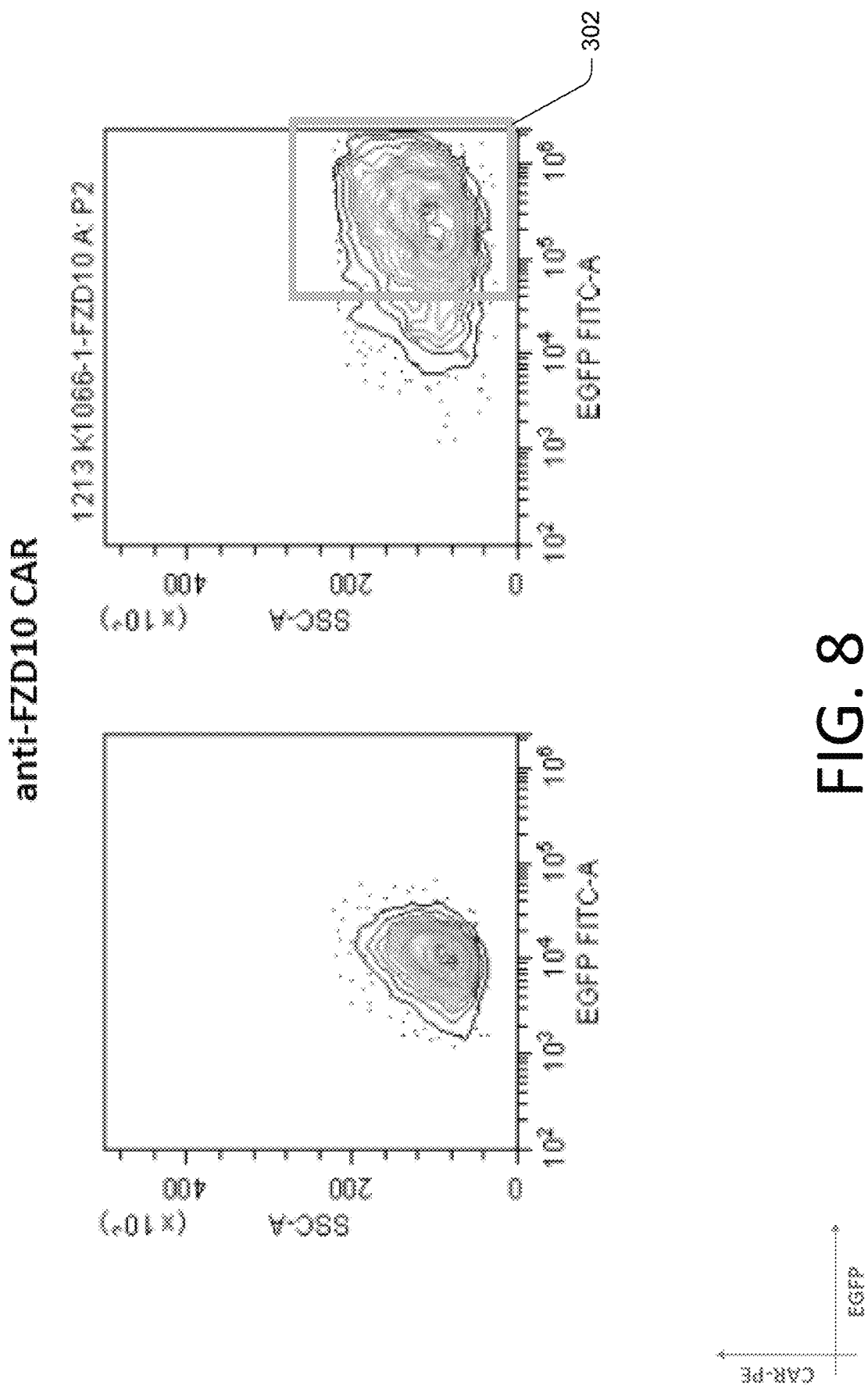
FIG. 8 shows assay results demonstrating that anti-FZD10 CAR T cell lines were established.
Figure 9:
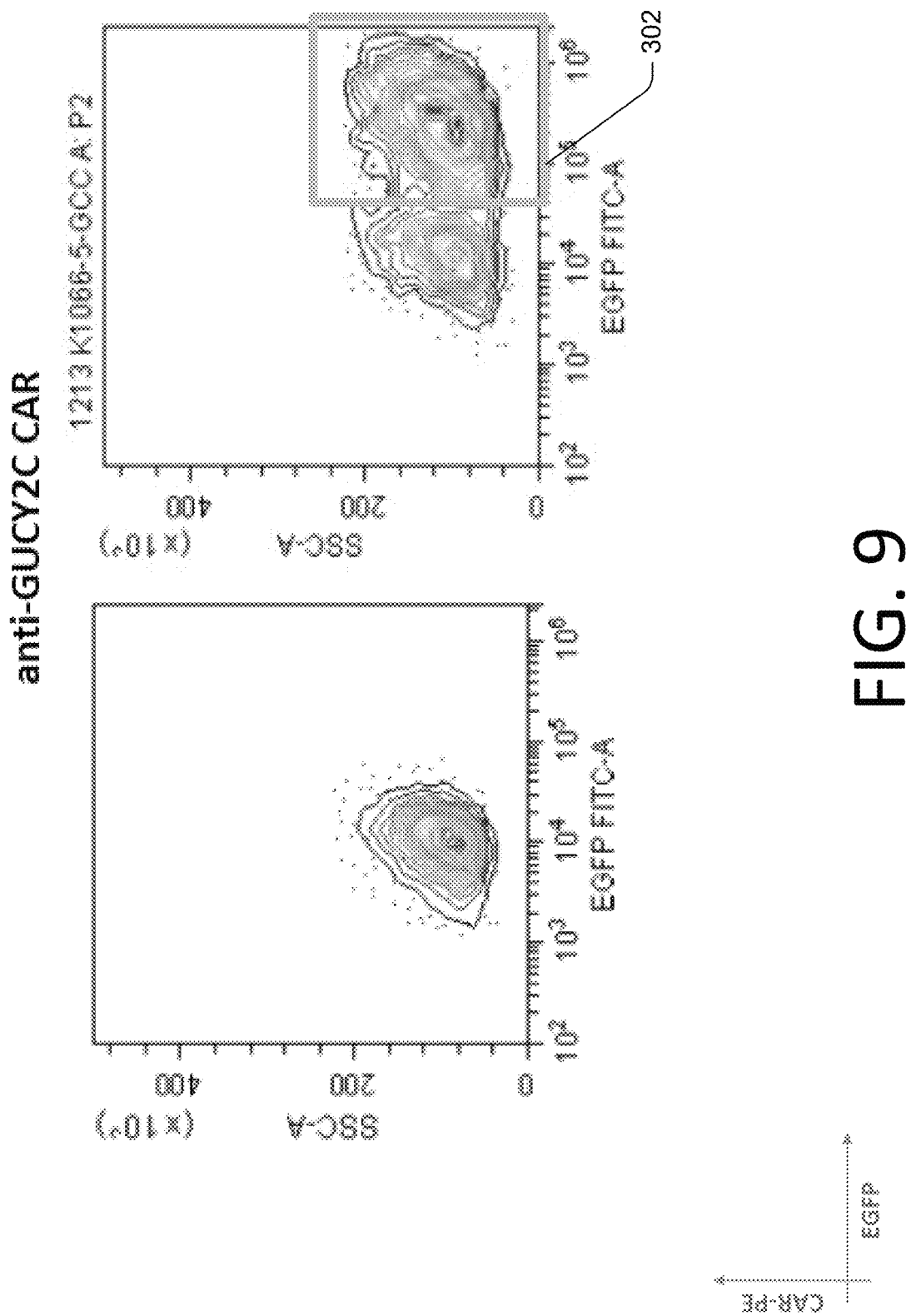
FIG. 9 shows assay results demonstrating that anti-GUCY2C CAR T cell lines were established.
Figure 10:
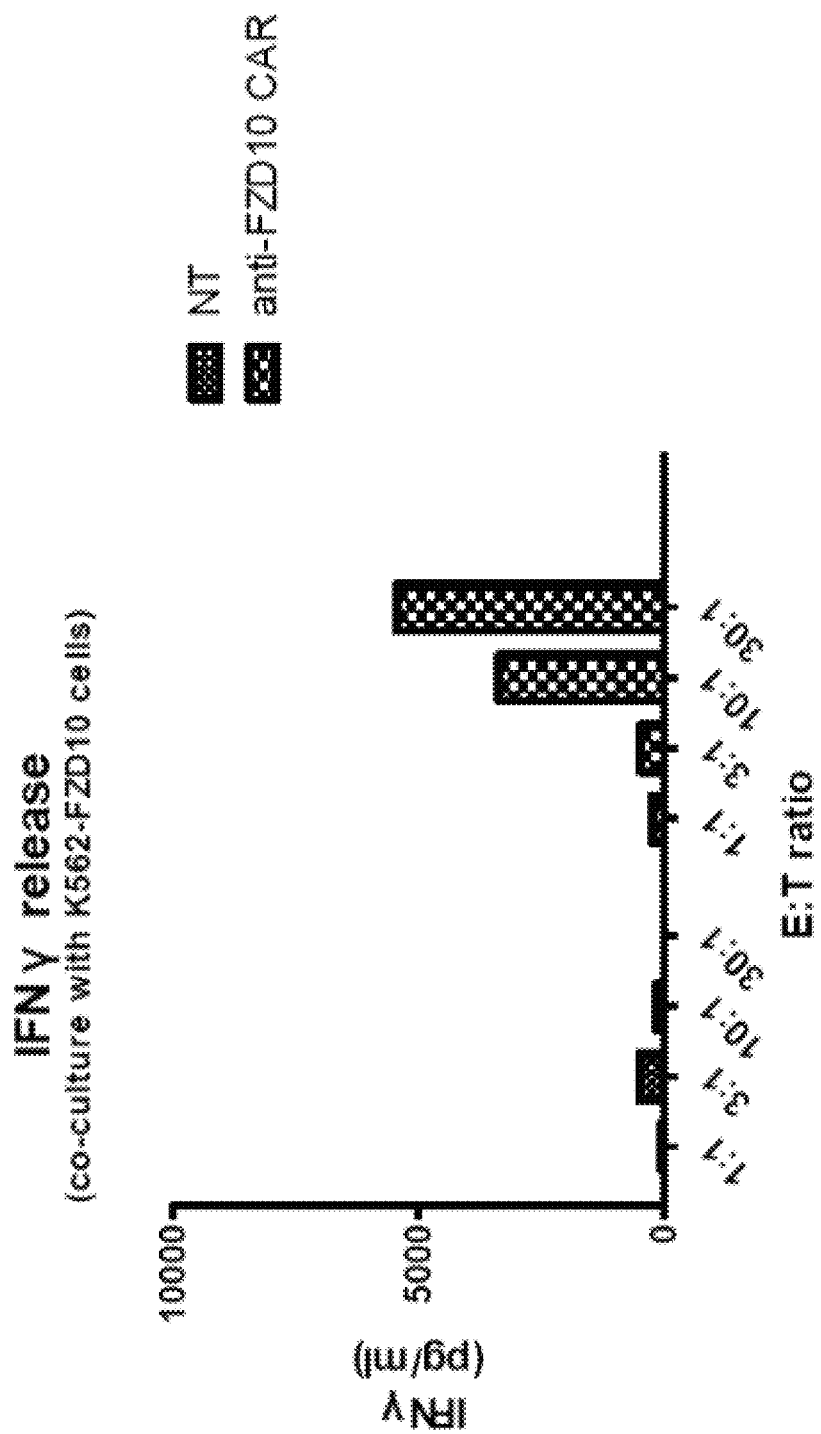
FIG. 10 shows co-cultivation assays demonstrating that anti-FZD10 CAR T cells recolonize specific tumor cells and release IFN-γ accordingly.
Figure 11:
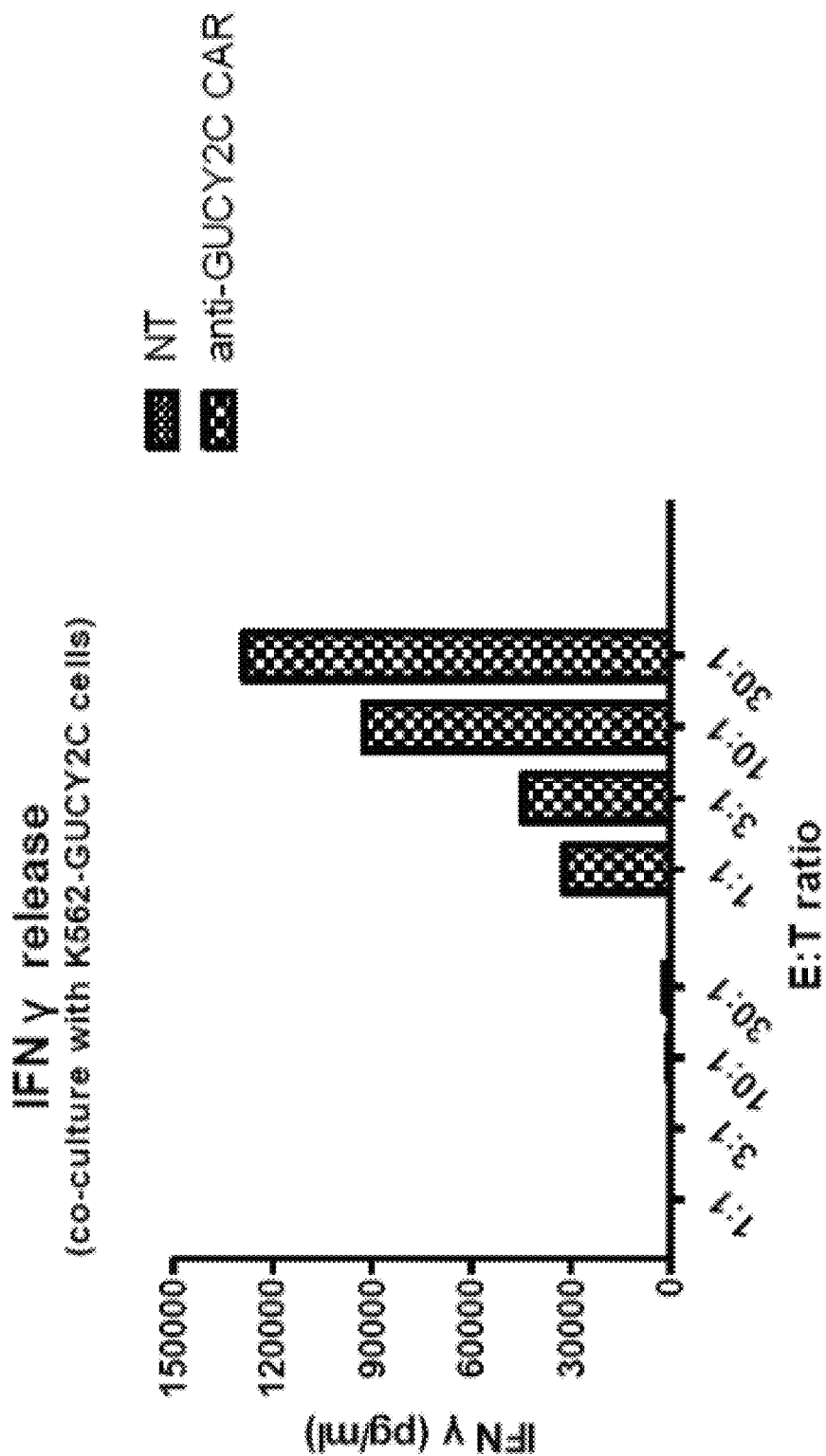
FIG. 11 shows co-cultivation assays demonstrating that anti-GUCY2C CAR T cells recolonize specific tumor cells and release IFN-γ accordingly.
Figure 12:
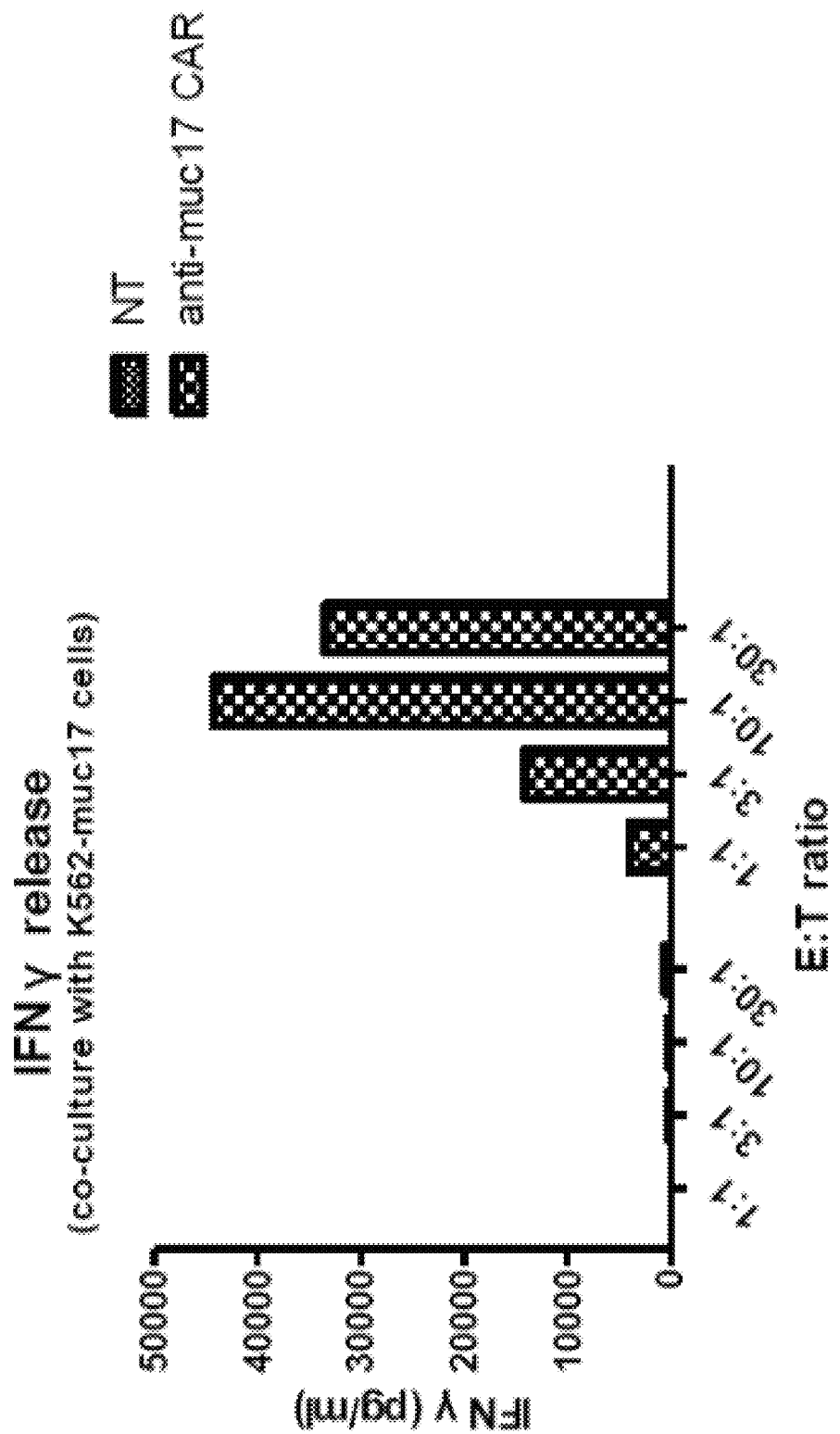
FIG. 12 shows co-cultivation assays demonstrating that anti-Muc17 CAR T cells recolonize specific tumor cells and release IFN-γ accordingly.
Figure 13:
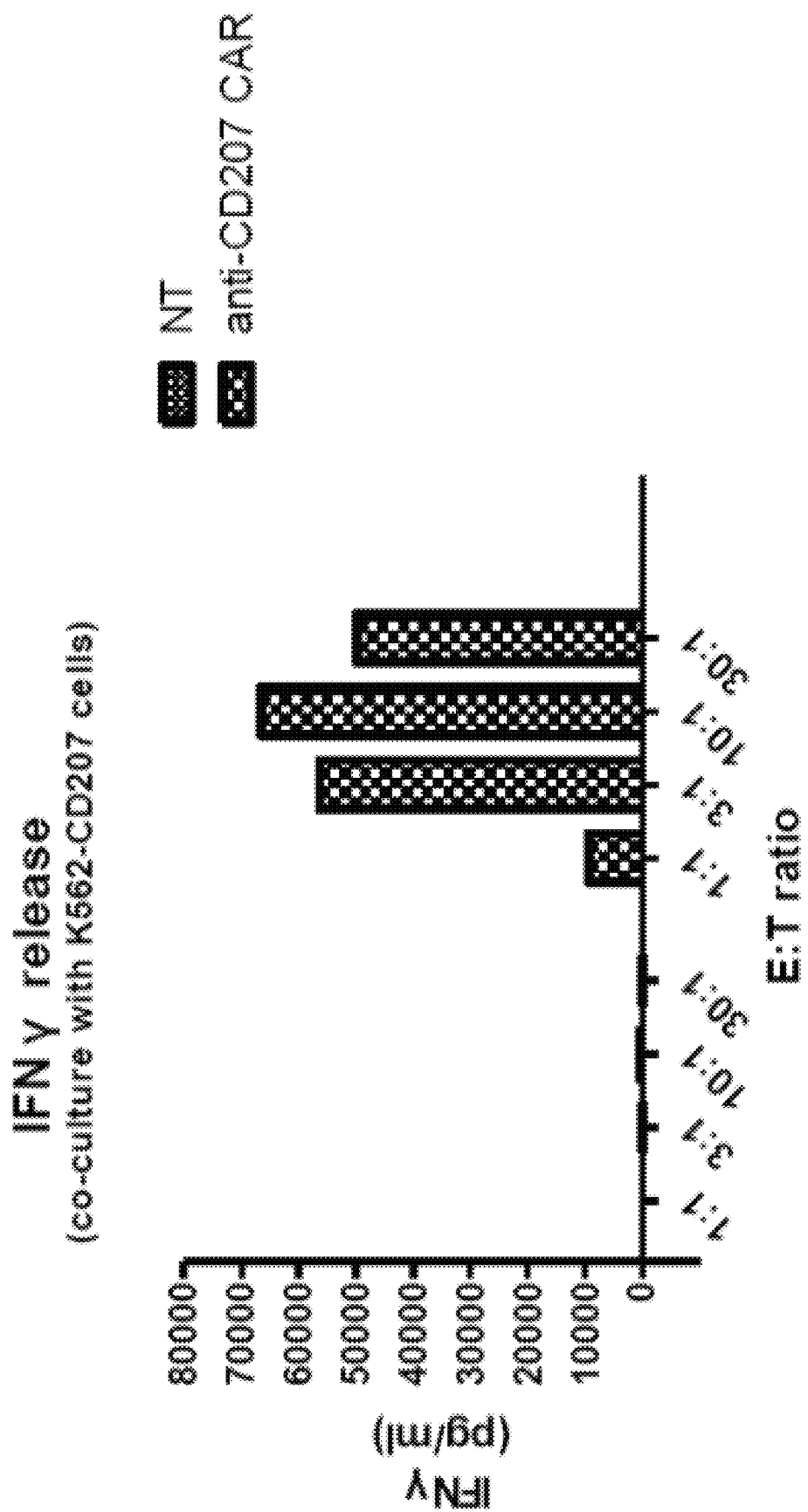
FIG. 13 shows co-cultivation assays demonstrating that anti-CD207 CAR T cells recolonize specific tumor cells and release IFN-γ accordingly.
Figure 14:
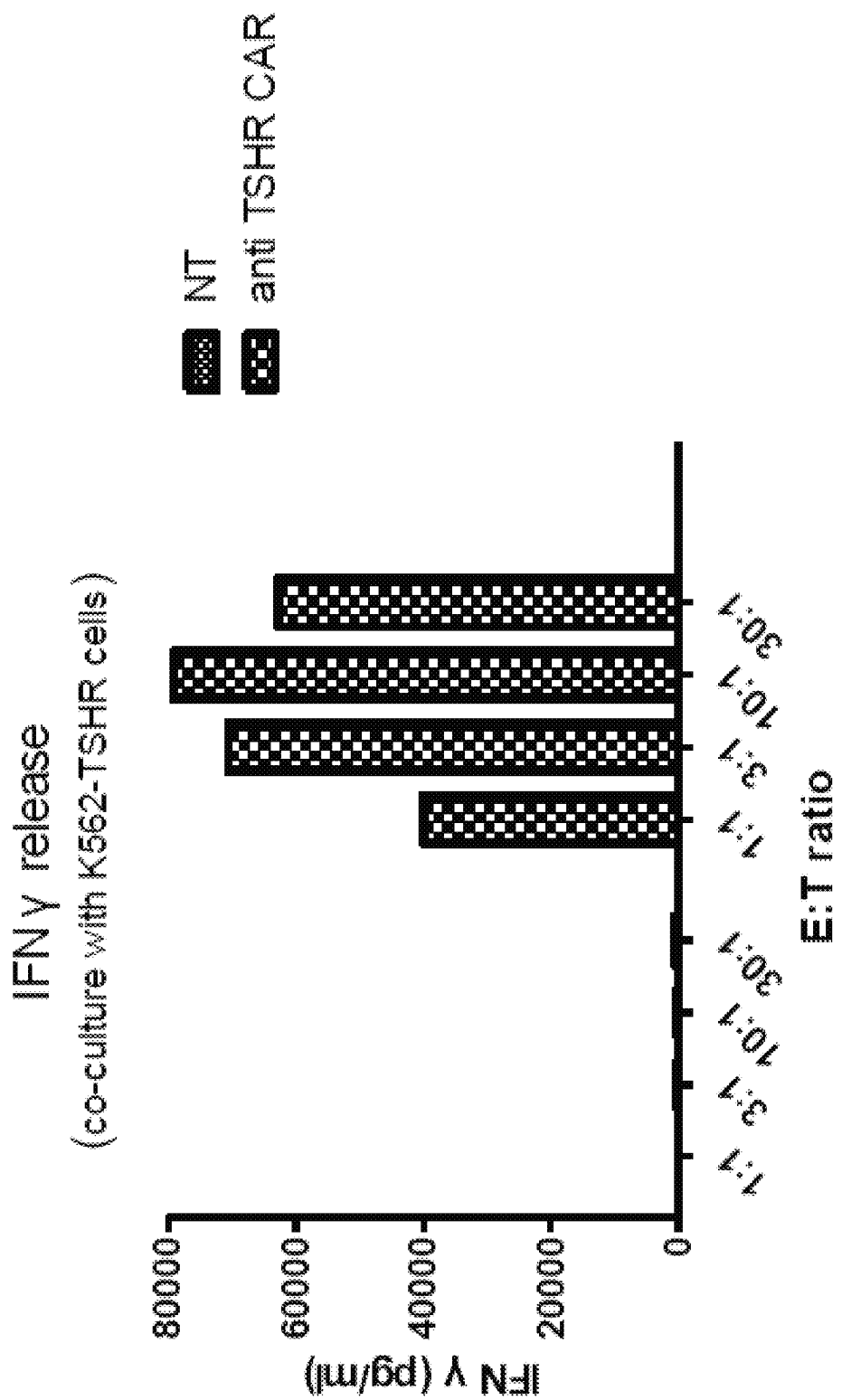
FIG. 14 shows co-cultivation assays demonstrating that anti-TSHR CAR T cells recolonize specific tumor cells and release IFN-γ accordingly.

Primary T cells were transduced with lentivirus including various CARs to establish different CAR T cell lines targeting different antigens listed in FIG. 1. These cells were obtained from healthy human donors. As illustrated in FIG. 3, the lentivirus included a nucleic acid sequence encoding CAR molecules, respectively, and further included the IRES-mCherry (green) construct, which encodes green fluorescence for confirmation of CAR expression. Taking anti-CD207/anti-Muc17 CAR T cell as examples in FIG. 3A, and expression of CARs was measured to confirm that CAR T-cell lines express specific anti-antigen molecules (See above boxes 302) in FIGS. 4-9. Techniques related to cell cultures, construction of lentiviral vectors, and flow cytometry may be found in "Treatment of Advanced Leukemia in Mice with mRNA-Engineered T Cells, HUMAN GENE THERAPY 22:1575-1586 (December 2011)", which is incorporated herein by reference.

Table 2 below lists various sequence identifiers and their sequences for establishing various anti-antigen CAR T cells.

| SEQ ID NO: | Identifier | Target tumors |
|---|---|---|
| 2 | scFv FZD10 | Ovary tumor |
| 5 | scFv TSHR | Thyroid Tumor |
| 8 | scFv PRLR | Breast cancer |
| 11 | scFv Muc17 | Gastric Cancer |
| 14 | scFv GUCY2C | colorectal Cancer |
| 17 | scFv CD207 | bladder Cancer |
| 36 | CAR FZD10 | Ovary tumor |
| 37 | CAR TSHR | Thyroid Tumor |
| 38 | CAR PRLR | Breast cancer |
| 39 | CAR Muc17 | Gastric Cancer |
| 40 | CAR GUCY2C | colorectal Cancer |
| 41 | CAR CD207 | bladder Cancer |
| 42 | CAR Prolactin | Breast cancer |
| 44 | CAR modified Prolactin | Breast cancer |

IFN-γ Release in Co-Cultivation Assays

Figure 15:
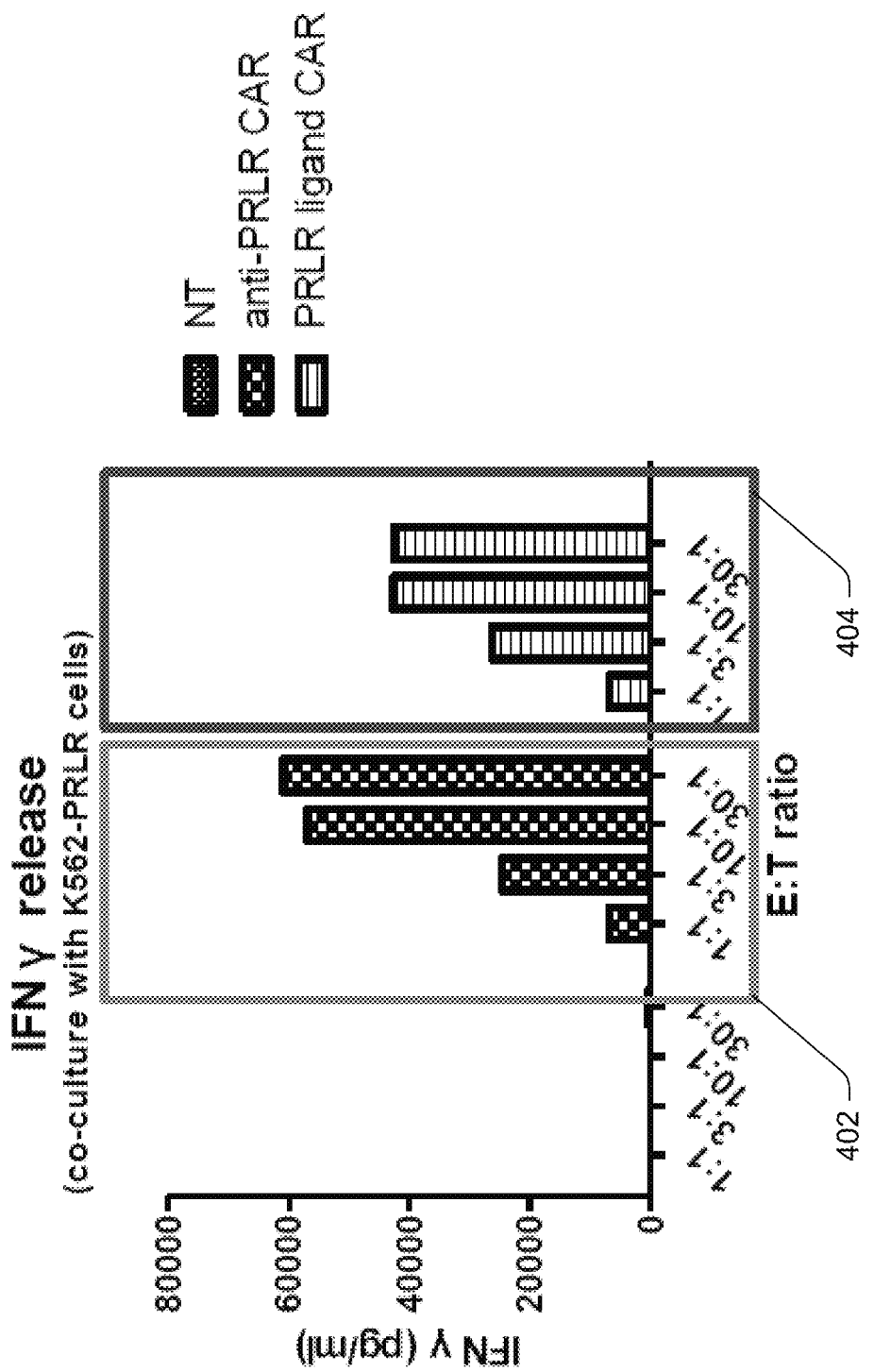
FIG. 15 shows co-cultivation assays demonstrating that anti-PRLR CAR T cells and PRLR ligand CAR T cells recolonize specific tumor cells and release IFN-γ accordingly.

Each type of CAR T cells and the corresponding type of antigen-expressed K562 cells were cocultured (See, Table 2), and CAT T cells' responses induced by the antigen-express K562 cells were measured. A ratio of E:T 1:1/3:1/10:1/30:1 (i.e., CAR T cells:target tumor cells) of CAR T cells and target tumor cells were cocultured for 24 hours. The supernatant was collected then, and release of IFN-γ was measured. Various levels of IFN-γ release were observed when CAR T cells and their corresponding antigen-express K562 cells were co-cultured. IFN-γ release is not obvious when the CAR T cells and wild-type K562 were co-cultured. This observation shows that the CAR T cells specifically identify the corresponding antigen-express K562 cells and attack these cells by releasing IFN-γ (see FIGS. 10-15). As illustrated in box 404 of FIG. 4B, T cells including prolactin-CAR also recognize target tumor cells expressing PRLR and release IFN-γ in response to co-culturing the prolactin-CAR T cells and the antigen-express K562 cells. As compared to box 402 in FIG. 15 (scFv anti-PRLR CAR T cells), prolactin-CAR T cells achieve a similar effect. Techniques related to cell cultures, construction of cytotoxic T-lymphocyte assay may be found in "Control of large, established tumor xenografts with genetically retargeted human T cells containing CD28 and CD137 domains. 3360-3365 PNAS Mar. 3, 2009, vol. 106 no. 9", which is incorporated herein by reference.

CAT T Cell Killing Assay

CAR T cell killing assays were conducted to measure the effectiveness of CAR T cells. Primary T cells were obtained from blood samples of healthy human donors. These T cells were transduced with a nucleic acid sequence encoding various CARs (See Table 2 and FIG. 1), respectively, and CAR expression on T-cells was measured using flow cytometry techniques.

Figure 16:
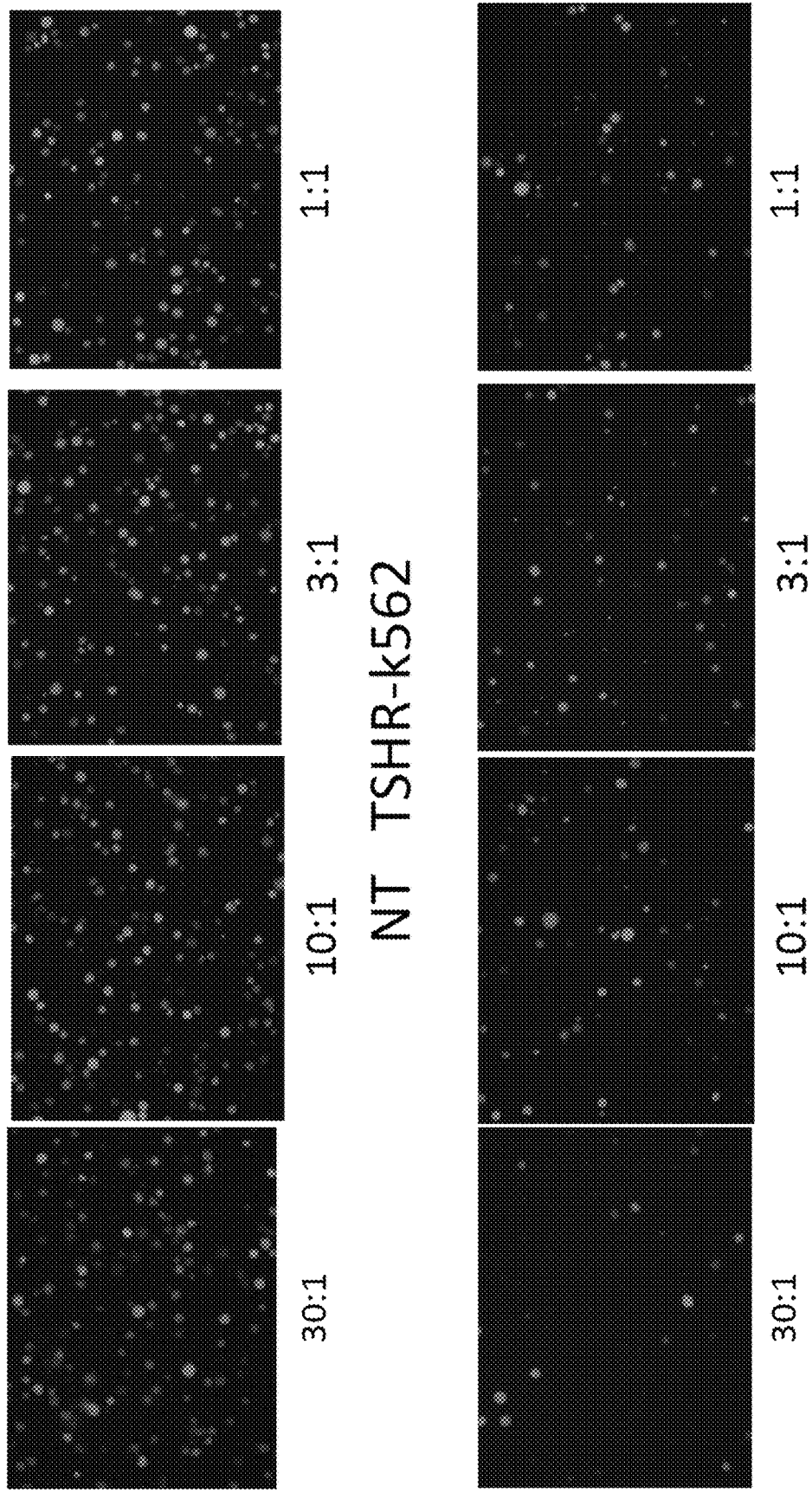
FIG. 16 shows killing assay results based on co-cultivation of anti-THSR CAR T cells and TSHR-K562 cells.
Figure 17:
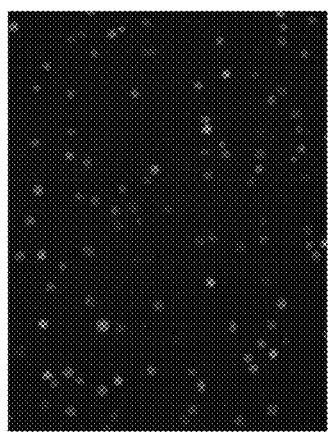
FIG. 17 shows killing assay results based on co-cultivation of anti-PRLR CAR T cells and PRLR-K562 cells.
Figure 17:
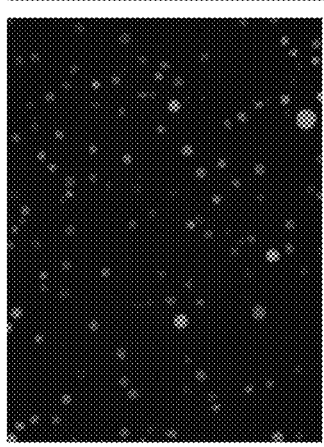
Figure 17:
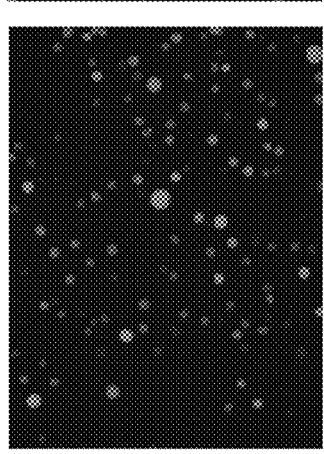
Figure 17:
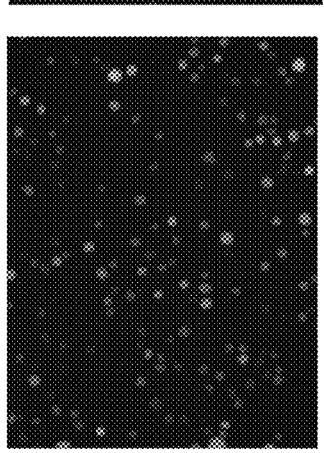
Figure 17:
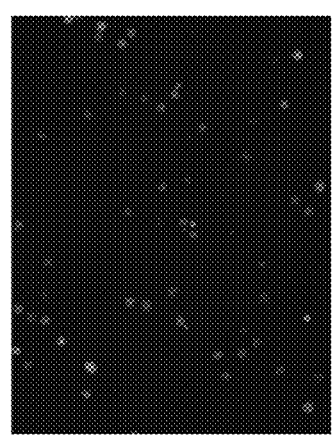
Figure 17:
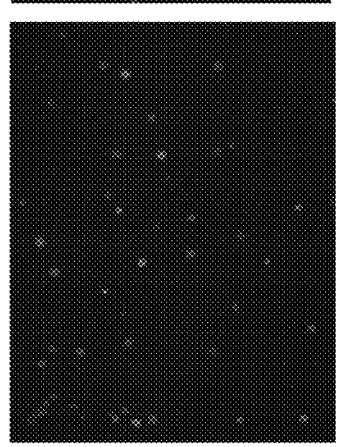
Figure 17:
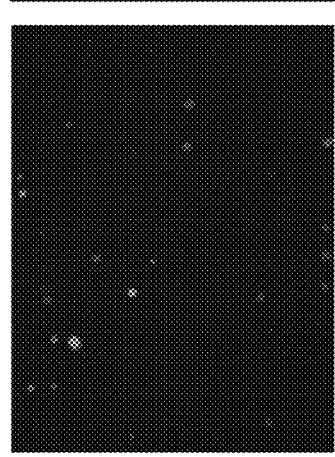
Figure 17:
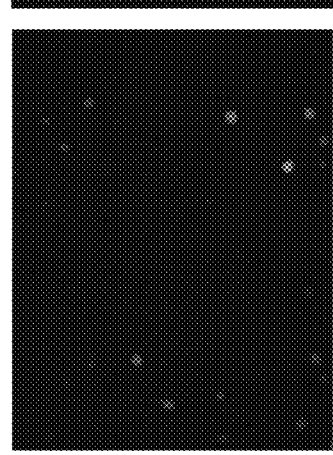
Figure 18:
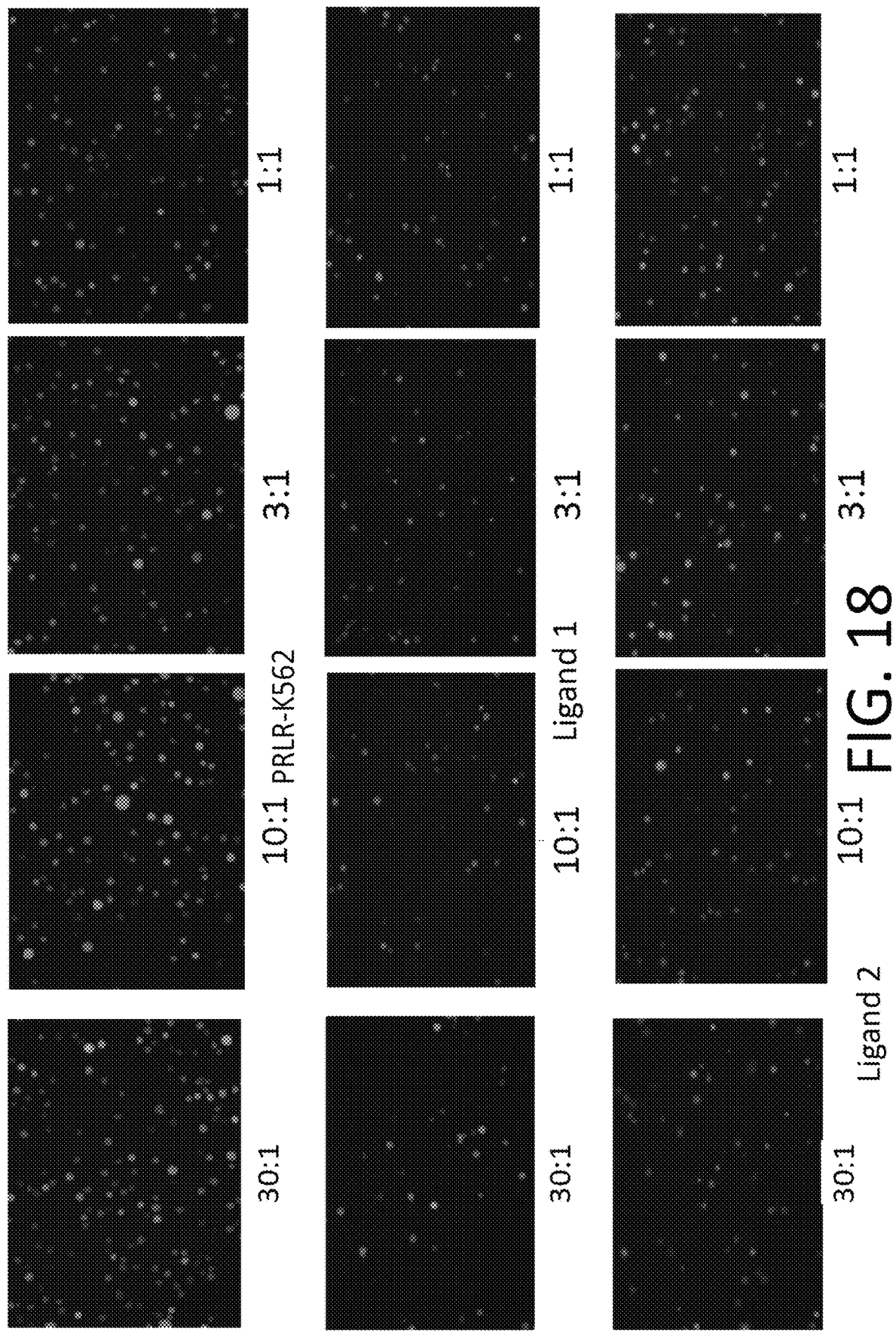
FIG. 18 shows killing assay results based on co-cultivation of PRLR ligand CAR T cells and PRLR-K562 cells. Ligand 1 indicates human wild-type prolactin receptor ligand (SEQ ID NO: 20), and ligand 2 indicates modified human prolactin receptor ligand (SEQ ID NO: 44).
Figure 19:
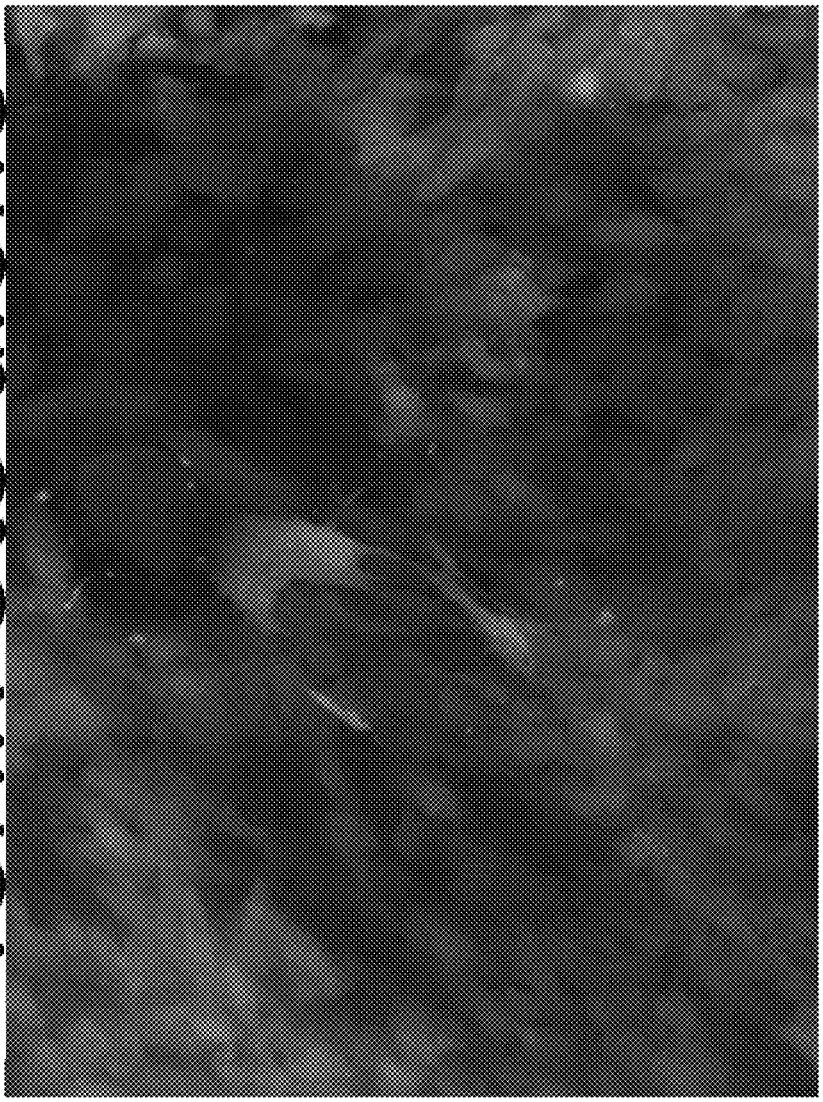
FIG. 19 is an image illustrating fluorescent signals observed from 3t3 cells expressing TSHR and fluorescent proteins (RFP).
Figure 20:
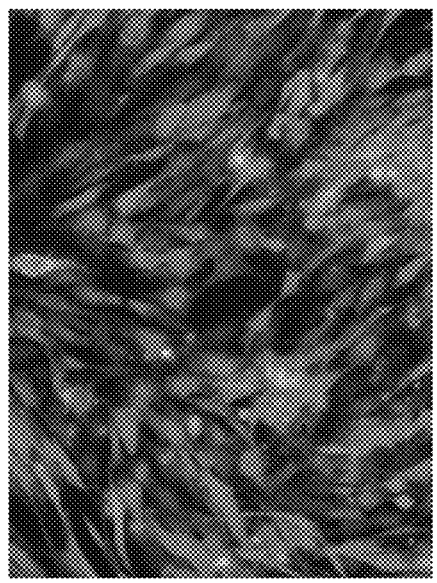
FIG. 20 shows killing assay results based on co-cultivation of anti-TSHR CAR T cells and TSHR-3T3 cells.
Figure 20:
Figure 20:
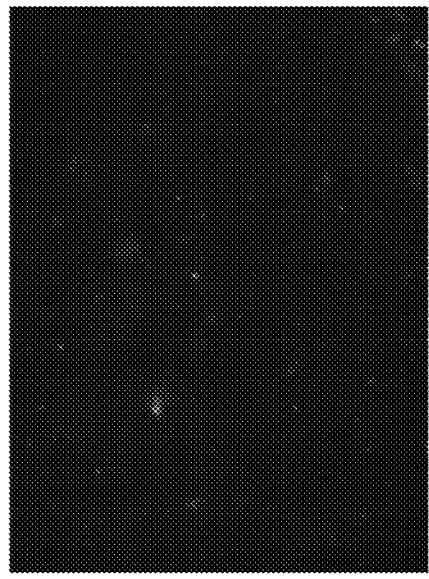
Figure 20:
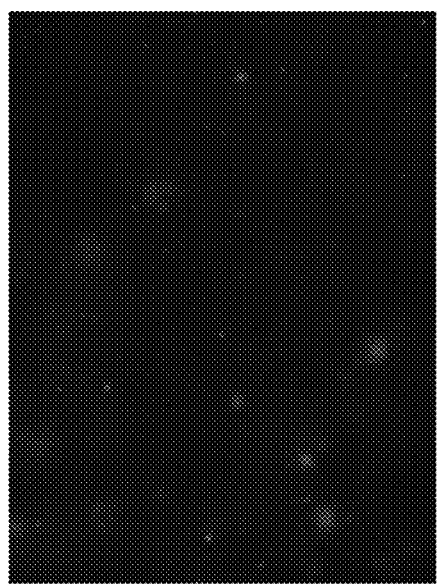
Figure 21:
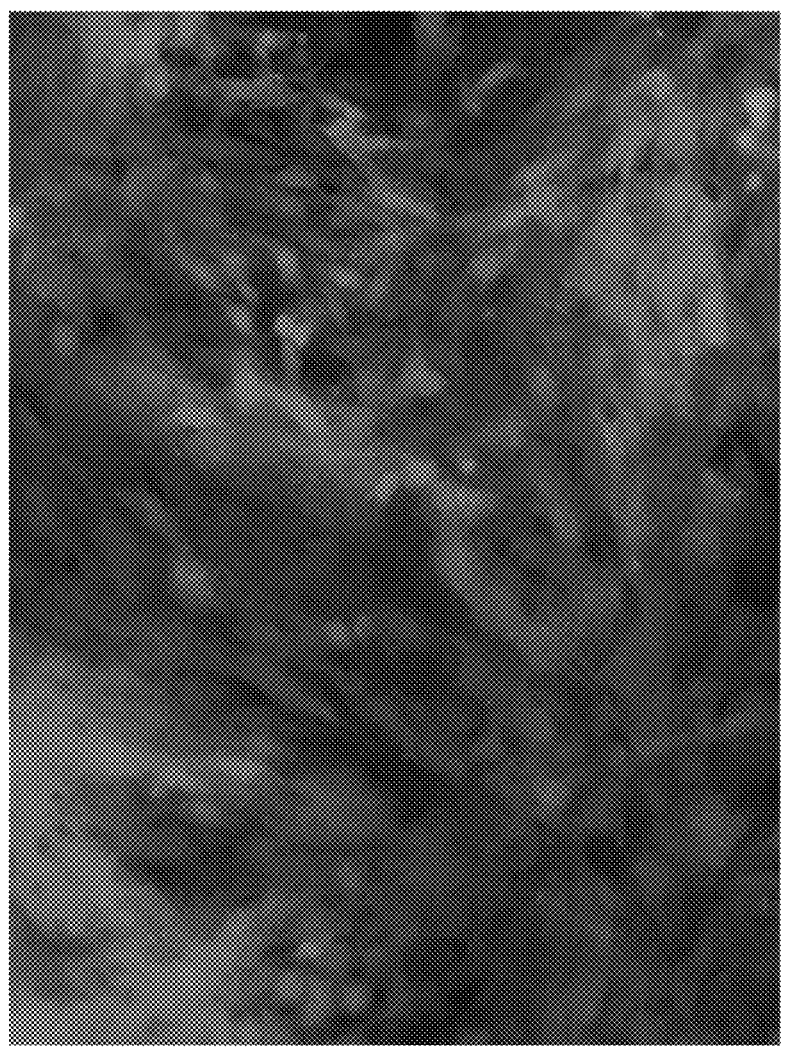
FIG. 21 is an image illustrating fluorescent signals observed from 3t3 cells expressing PRLR and fluorescent proteins (RFP).
Figure 22:
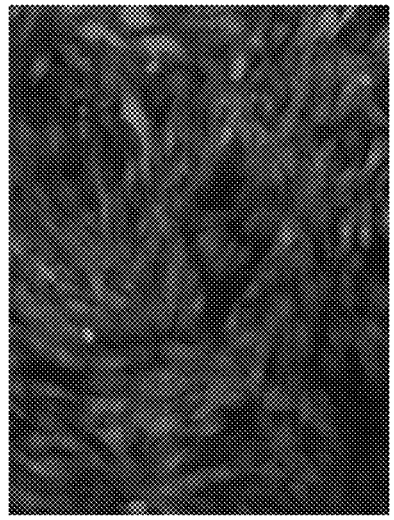
FIG. 22 shows killing assay results based on co-cultivation of anti-PRLR CAR T cells and PRLR-3T3 cells.
Figure 22:
Figure 22:
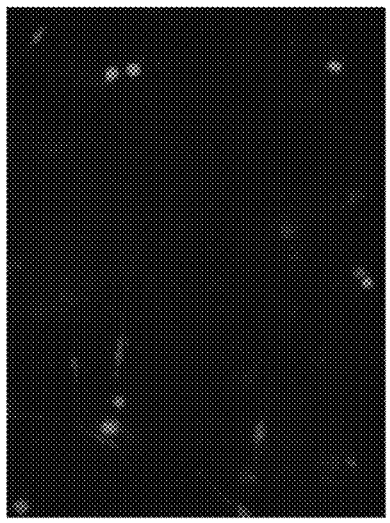
Figure 22:
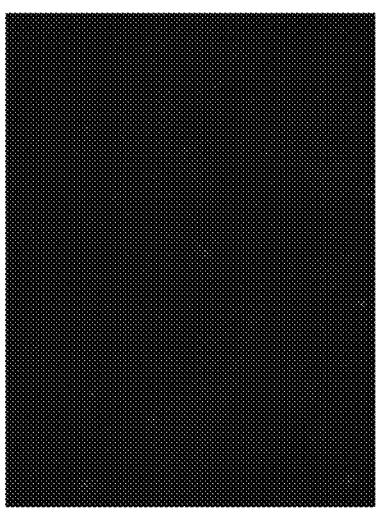
Figure 23:
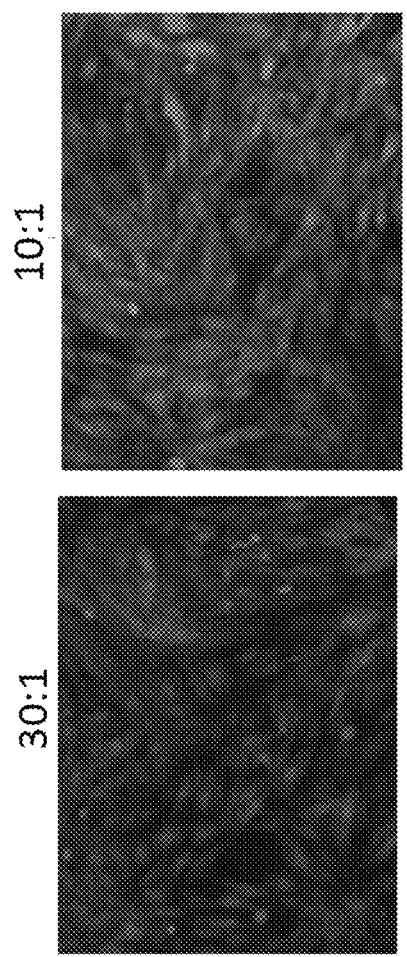
FIG. 23 shows killing assays results based on co-cultivation of PRLR ligand CAR T cells and PRLR-3T3 cells.
Figure 23:
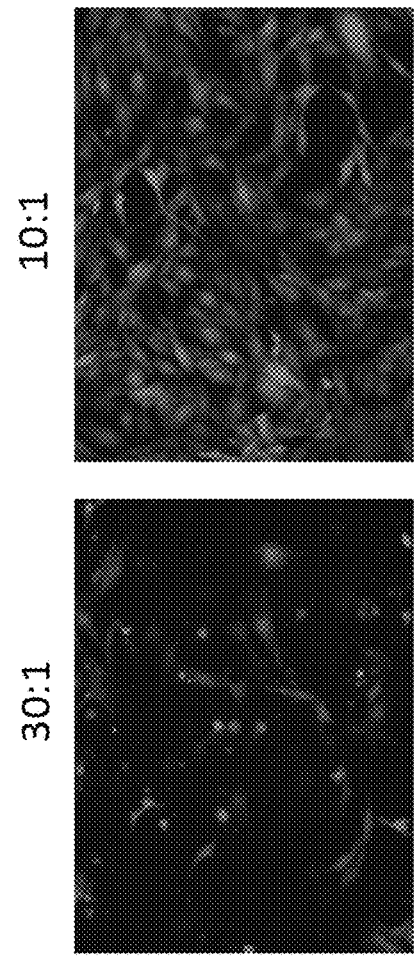

K562 cells were transduced with nucleic acid sequences encoding corresponding human antigens (See FIG. 1), respectively, and antigen expression was measured using flow cytometry techniques. Further antigen-expression K562 cells were transduced with a nucleic acid sequence encoding fluorescent proteins (RFP) for killing assay analysis. Various CAR T cells were incubated with corresponding K562 cells for 24 hours in various E:T ratios (30:1, 10:1, 3:1, 1:1), and red fluorescence signals from cocultured cells were observed. For example, CAR T cells expressing anti-THSR CAR (SEQ ID NO: 5) were co-cultured with K562 expressing human THSR (SEQ ID NO: 26) for at least five days. As compared with normal T cells, CAR T cells significantly reduced numbers of antigen-expression K562 cells. Examples of anti-PRLR CAR, anti-THSR CAR, and Prolactin CAR T cells were provided in FIGS. 16-18. In these examples, red fluorescence signals of cocultured cells were observed at day five after co-culturing the CAR T cells and the corresponding antigen-expression K562 cells.

The car T cell killing analysis was further performed using 3T3 murine fibroblasts (ATCC). 3T3 cells were transduced with various human antigens (See FIG. 1), and antigen expression on 3T3 cells was measured using flow cytometry techniques. Further, 3T3 cells were transduced with nucleic acid sequence encoding fluorescent proteins (RFP) for killing assay analysis. 3T3 cells expressing human target antigens/RFP and corresponding CAR T cells were cocultured at an E:T 30:1 or 10:1, respectively, and then fluorescent signals were observed from the cocultured cells for at least five days. As compared with normal T cells, CAR T cells significantly reduced numbers of antigen-expression 3T3 cells. Examples of anti-PRLR CAR, anti-PRLR CAR, and Prolactin CAR T cells were provided in FIGS. 19-23. In these examples, red fluorescence signals of cocultured cells were observed at day five after co-culturing the CAR T cells and the corresponding antigen-expression 3T3 cells.

In Vivo Anti-Tumor Activity

Heterotransplantation of human cancer cells or tumor biopsies into immunodeficient rodents (xenograft models) has, for the past two decades, constituted the major preclinical screen for the development of novel cancer therapeutics (Song et al., Cancer Res. PMC 2014 Aug. 21, and Morton et al., Nature Protocols, 2, -247-250 (2007)). To evaluate the anti-tumor activity of CAT T cells in vivo, immunodeficient mice bearing tumor xenografts were to evaluate CAR T's anti-tumor activity.

K562-PRLR-RFP cells were used to establish the immunodeficient mice bearing PRLR tumor xenografts. On day one, K562-PRLR-RFP cells were injected into tail veins of the immunodeficient mice. On day two or three, irradiation was performed on the immunodeficient mice in 2 Gy fractions. On day three, the formation of tumor cells in the immunodeficient mice was observed.

Figure 24:
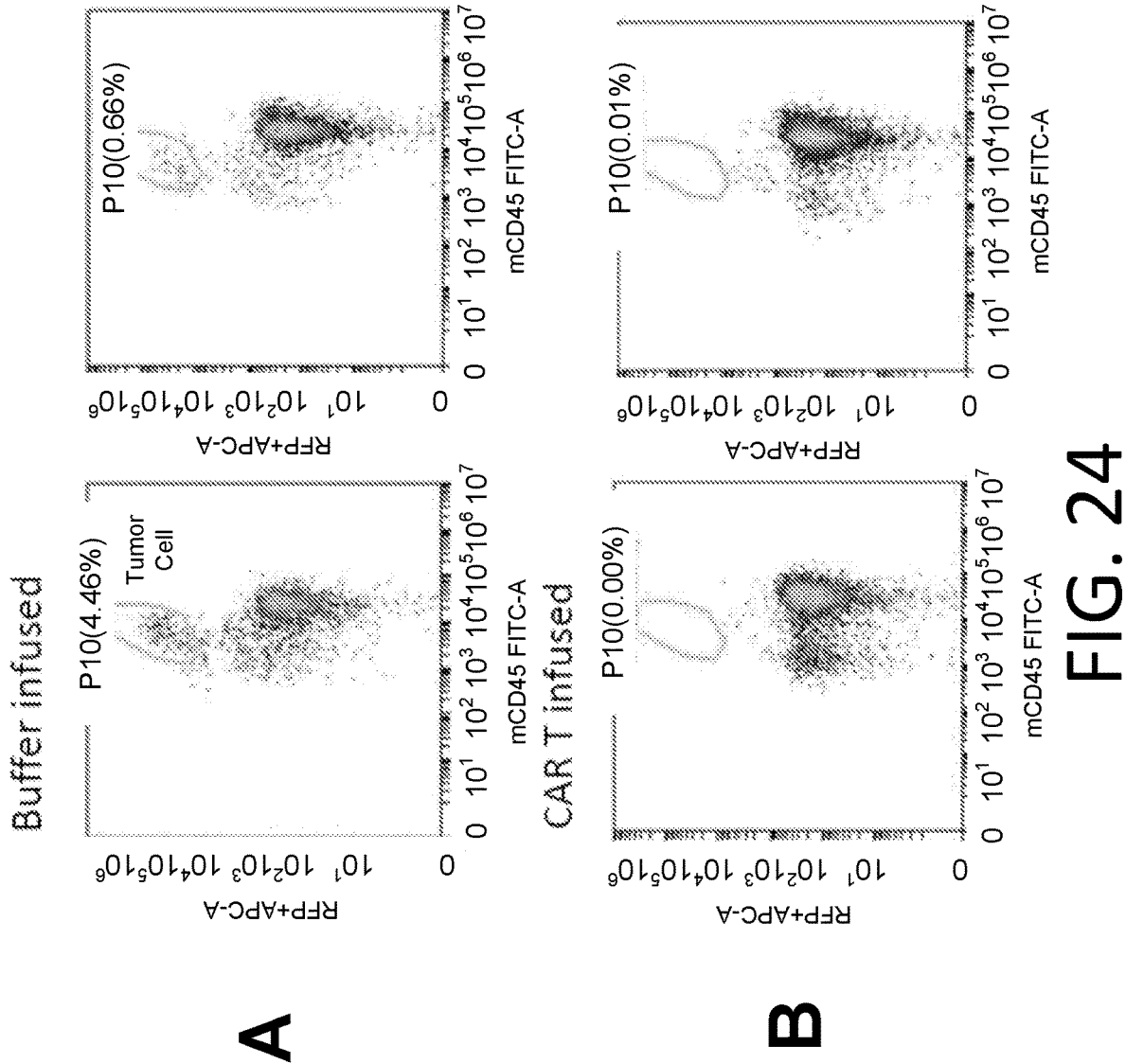
FIG. 24 is a series of images demonstrating in vivo antitumor activity of CAR T cells in accordance with embodiments of the present disclosure. Flow cytometry was used to evaluate the presence of K562-PRLR-RFP cells. In group A (upper images), two mice were injected with K562-PRLR-RFP cells, and buffer without human CAR T cells was transfused to these two mice. K562-PRLR-RFP cells (i.e., circled areas) were observed four weeks after injection. In group B (lower images), two mice were injected with K562-PRLR-RFP cells, and human CAR T cells were transfused to these two mice. K562-PRLR-RFP cells were not observed four weeks after injection (i.e., circled areas), showing the anti-tumor activity of the CAR T cells.
Figure 25:
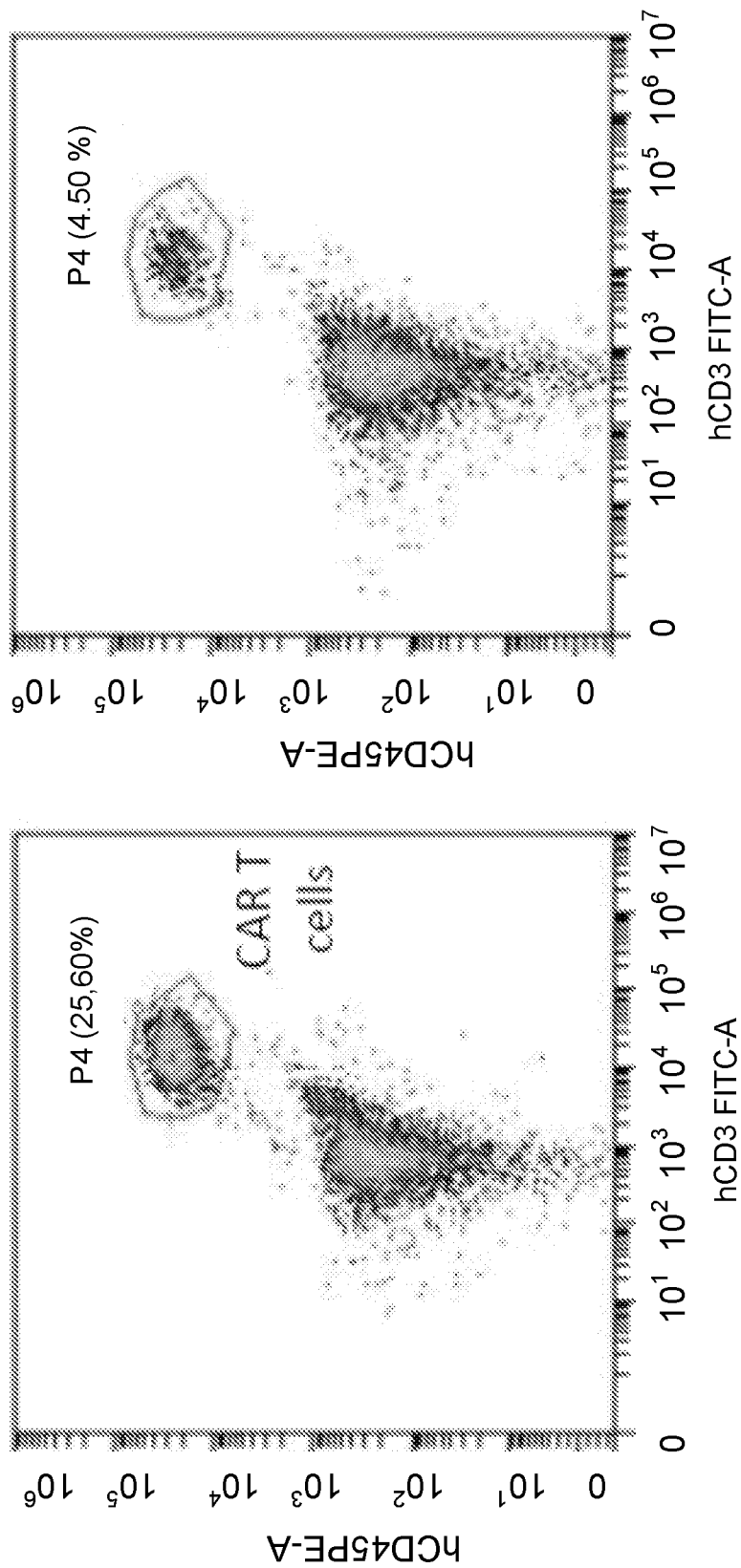
FIG. 25 is another series of images demonstrating in vivo antitumor activity of CAR T cells in accordance with embodiments of the present disclosure. Flow cytometry was used to evaluate the presence of CAR T cells in mice. Two mice were injected with K562-PRLR-RFP cells, and human CAR T cells were transfused to these two mice. Human CAR T cells (i.e., circled areas) were observed four weeks after injection, consistent with the anti-tumor activity of the CAR T cells shown in FIG. 24.

On day three, anti-PRLR human CAR T cells (i.e., anti-PRLR CAR T) were transfused to the immunodeficient mice, and anti-tumor activities were observed in the immunodeficient mice. The anti-PRLR CAR T cells were made by the protocol described in this present disclosure. The presence of K562-PRLR-RFP cells was evaluated using the peripheral blood of the immunodeficient mice by flow cytometry after three or four weeks. In control, the buffer was transfused to the immunodeficient mice, and the immunodeficient mice died within four to six weeks. As for the immunodeficient mice transfused with anti-PRLR CAR T, the K562-PRLR-RFP cells were not observed, and the immunodeficient mice behaved normally. Human CD3 cells were further observed in the immunodeficient mice (FIGS. 24 and 25). It is concluded that CAR T cells have anti-tumor activity in mice. Additional information about the protocol was provided in Table 3 below.

TABLE 3

| Tumor cell | K562-PRLR RFP cells |
| --- | --- |
| Tumor cells transplanted | $5*10^5$ cells/mouse |
| irradiation | 2Gy |
| CAR T cells infused | $1*10^7$ cells/mouse |

Figure 26:
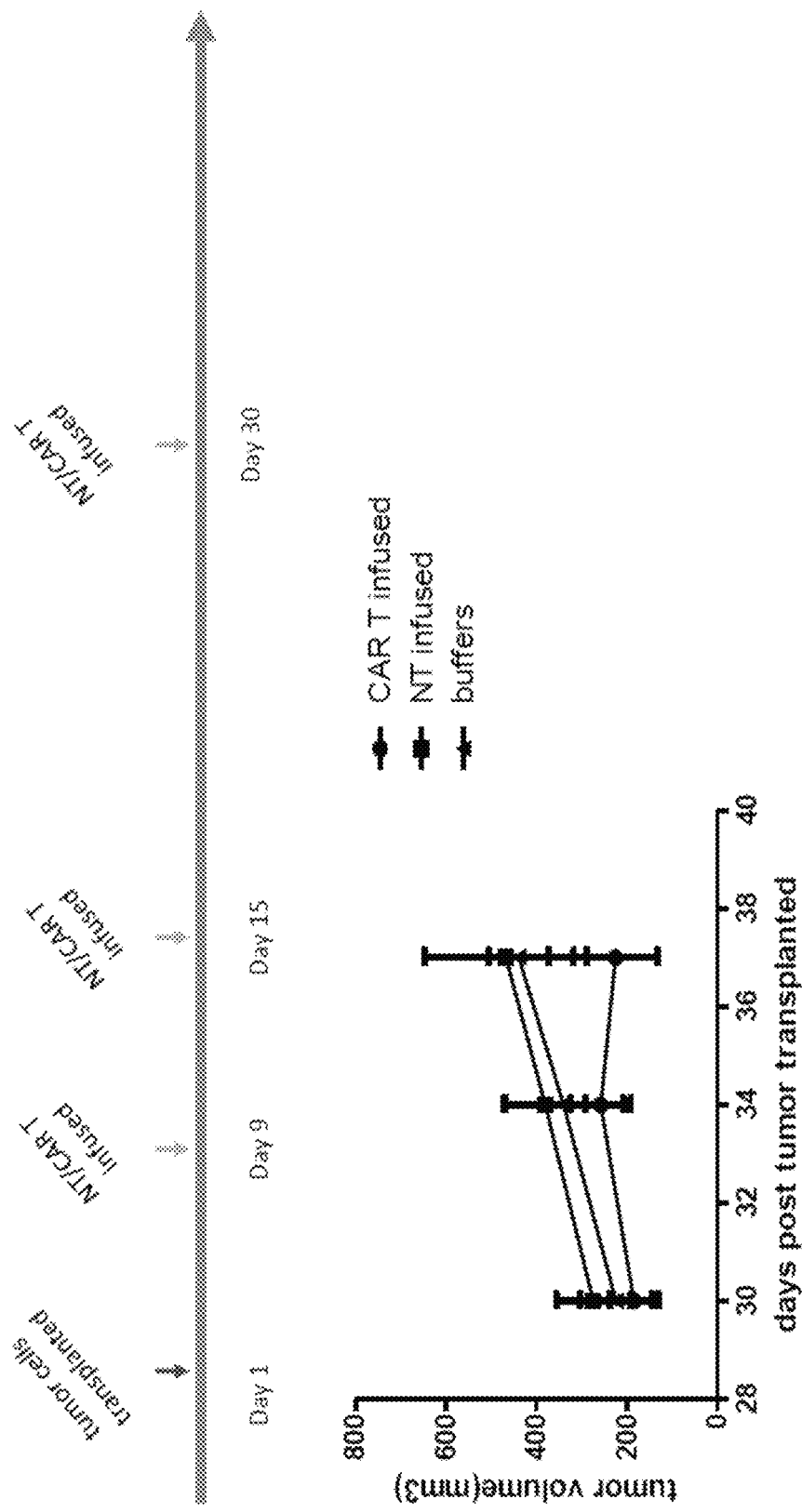
FIG. 26 shows in vivo antitumor activity of CAR T cells in established TNBC xenografts in immunodeficient mice. The upper diagram shows the establishment of the TNBC xenografts in immunodeficient mice and the measurement of antitumor activity. TNBC xenografts in immunodeficient mice were established by subcutaneously transplanting cells of MDA-MB-453 (TNBC) cell lines. After transplantation, NT/CAR T cells were transfused to the mice on Day 9, Day 15, and Day 30. Tumor volumes were observed and measured. The lower plot shows the in vivo antitumor activity of CAR T cells. The longitudinal axis represents tumor volumes, and the horizontal axis represents time after the transplantation.

Anti-tumor activity of CAR T cells was further observed in TNBC xenografts in immunodeficient mice. MDA-MB-453 (TNBC, triple-negative breast cancer) cell lines were used to established TNBC xenografts in immunodeficient mice. As illustrated in the upper diagram of FIG. 26, TNBC xenografts in immunodeficient mice were established by subcutaneously transplanting cells of MDA-MB-453 (TNBC) cell lines. After transplantation, $1.5 \times 10^7$ NT/anti-PRLR human CAR T cells (anti-PRLR CAR T) were transfused to each of the mice on Day 9, Day 15, and Day 30 (e.g., $7 \times 10^5$ CAR T cells per gram). Tumor volumes were observed and measured. Tumor volumes were calculated using the equation: $V=\pi/6*a*b*b$. "a" is the long axis of the tumor, and "b" is the minor axis. As shown in the lower plot of FIG. 26, in vivo antitumor activity, was observed in mice that are transfused with anti-PRLR CAR T.

BCPAP cells were overexpressed TSHR (BCPAP-TSHR cells) and used to establish the immunodeficient mice bearing TSHR tumor xenografts. On day one, BCPAP-TSHR cells were injected subcutaneously into the immunodeficient mice. The formation of tumor cells in the immunodeficient mice was then observed. Anti-TSHR human CAR T cells (i.e., anti-TSHR CAR T) were transfused to the immunodeficient mice through tail veins on day 7, day 14, and day 21 (i.e., CART). Human T cells were transfused to the immunodeficient mice (i.e., NT) on day 7, day 14, and day 21. Additional information about the protocol was provided in Table 4 below.

TABLE 4

| Tumor cells | BCPAP-TSHR cells |
|---|---|
| Tumor cells transplanted | $2*10^6$ cells/mouse |
| CAR T cells infused | $5*10^6$ cells/mouse |
| | ($2.5 \times 10^5$ CAR T Cells per gram) |

Figure 27:
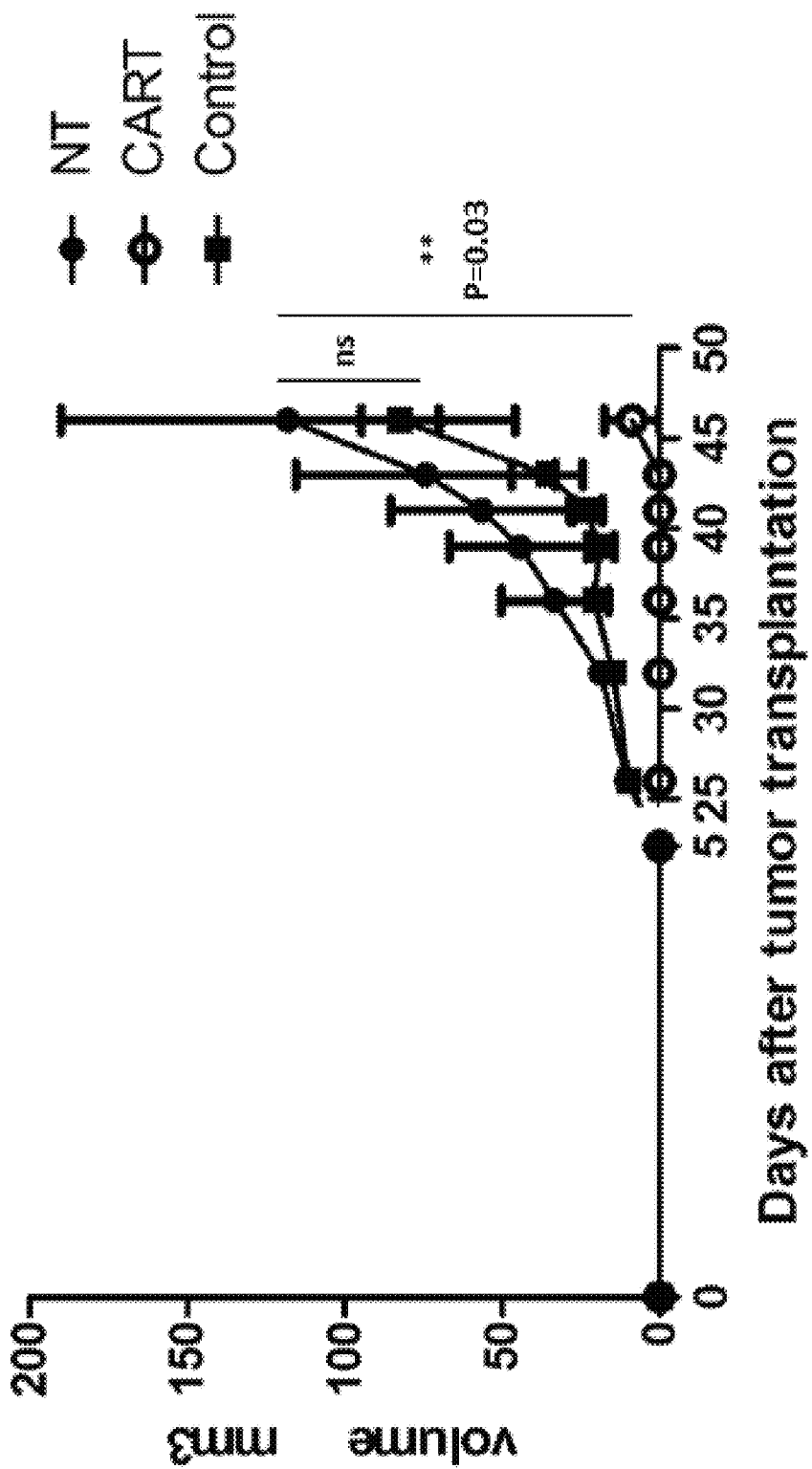
FIG. 27 shows in vivo antitumor activity of CAR T cells in established TNBC xenografts in immunodeficient mice. Thyroid cancer xenografts in immunodeficient mice were established by subcutaneously transplanting cells of B-CPAP cell line (thyroid cancer cell line). After transplantation, NT/CAR T cells were transfused to the mice on Day 9, Day 15, and Day 30. Tumor volumes were observed and measured. The lower plot shows the in vivo antitumor activity of CAR T cells. The longitudinal axis represents tumor volumes, and the horizontal axis represents time after the transplantation.

Between day 21 to 50, tumor volumes on mice of CART, NT and the control (without transfusion with cells) were observed and measured. Tumor volumes were calculated using the equation: $V=\pi T/6*a*b*b$. "a" is the long axis of the tumor, and "b" is the minor axis. As shown in the plot of FIG. 27, in vivo antitumor activity, was observed in mice that are transfused with anti-TSHR CAR T.

As described above, the treatment methods described herein can easily be adapted for other species or subjects, such as humans.

Table 5 below lists various sequence identifiers and their sequences.

| SEQ ID NO: | Identifier |
|---|---|
| 1 | SP |
| 2 | scFv FZD10 |
| 3 | 2L-FZD10 |
| 4 | 2H-FZD10 |
| 5 | scFv TSHR |
| 6 | 5L-TSHR |
| 7 | 5H-TSHR |
| 8 | scFv PRLR |
| 9 | 8L-PRLR |
| 10 | 8H-PRLR |
| 11 | scFv Muc17 |
| 12 | 11L-Muc17 |
| 13 | 11H-Muc17 |
| 14 | scFv GUCY2C |
| 15 | 14L-GUCY2C |
| 16 | 14H-GUCY2C |
| 17 | scFv CD207 |
| 18 | 17L-CD207 |
| 19 | 17H-CD207 |
| 20 | Prolactin (ligand) |
| 21 | Hinge & transmembrane domain |
| 22 | Co-stimulatory region |
| 24 | A-FZD10 |
| 25 | A-FZD10 (amino acid) |
| 26 | B-TSHR |
| 27 | B-TSHR (amino acid) |
| 28 | C-PRLR |
| 29 | C-PRLR (amino acid) |
| 30 | D-Muc17 |
| 31 | D-Muc17 (amino acid) |
| 32 | E-GCC |
| 33 | E-GCC (amino acid) |
| 34 | F-CD207 |
| 35 | F-CD207 (amino acid) |
| 36 | CAR FZD10 |
| 37 | CAR TSHR |
| 38 | CAR PRLR |
| 39 | CAR Muc17 |
| 40 | CAR GUCY2C |
| 41 | CAR CD207 |
| 42 | CAR Prolactin |
| 43 | CAR modified Prolactin |
| 44 | Prolactin (mutation) |
| 45 | Hinge & transmembrane domain |

What is claimed is:

1. A chimeric antigen receptor (CAR), wherein the CAR comprises an extracellular domain, a transmembrane domain, and an intracellular domain, and wherein the extracellular domain comprises amino acid sequence SEQ ID NO: 5.

2. The CAR of claim 1, wherein the CAR comprises amino acid sequence SEQ ID NO: 37.

3. The isolated nucleic acid sequence of claim 1, wherein the intracellular domain comprises a CD3 zeta signaling domain.

4. The CAR of claim 3, wherein the intracellular domain further comprises a costimulatory signaling region comprising an intracellular domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, and any combination thereof.

5. A composition comprising the CAR of claim 1 and a carrier.

6. A pharmaceutical composition comprising the CAR of claim 1 and a pharmaceutically acceptable carrier.

7. A nucleic acid encoding the CAR of claim 1.

8. A vector comprising the nucleic acid of claim 7.

9. A cell comprising the nucleic acid of claim 7.

10. A population of cells comprising the nucleic acid of claim 7.

11. The population of cells of claim 10, wherein the population of cells comprises T cells.

12. A pharmaceutical composition comprising the population of T cells of claim 11.

13. A method of stimulating an anti-tumor immune response in a subject in need thereof, the method comprising administering an effective amount of the pharmaceutical composition of claim 12 to the subject, thereby stimulating anti-tumor immune response.

14. The method of claim 13, wherein the subject is diagnosed with thyroid cancer.

15. A method of stimulating an immune response in a population of cells expressing thyroid stimulating hormone receptor (TSHR), the method comprising contacting the population of cells with an effective amount of the pharmaceutical composition of claim 12.

16. The method of claim 15, wherein the immune response is a T cell-mediated immune response.

17. The method of claim 15, wherein the population of cells are in a subject.

18. The method of claim 15, where the immune response is an anti-tumor immune response.

19. A nucleic acid encoding the CAR of claim 2.

20. A nucleic acid encoding the CAR of claim 3.

21. A nucleic acid encoding the CAR of claim 4.

22. A vector comprising the nucleic acid of claim 19.

23. A vector comprising the nucleic acid of claim 20.

24. A vector comprising the nucleic acid of claim 21.

25. A cell comprising the nucleic acid of claim 19.

26. A cell comprising the nucleic acid of claim 20.

27. A cell comprising the nucleic acid of claim 21.

28. A population of cells comprising the nucleic acid of claim 19.

29. A population of cells comprising the nucleic acid of claim 20.

30. A population of cells comprising the nucleic acid of claim 21.

31. A pharmaceutical composition comprising the population of cells of claim 28.

32. A pharmaceutical composition comprising the population of cells of claim 29.

33. A pharmaceutical composition comprising the population of cells of claim 30.

* * * * *

UNITED STATES PATENT AND TRADEMARK OFFICE
CERTIFICATE OF CORRECTION

PATENT NO. : 10,654,934 B2
APPLICATION NO. : 15/897743
DATED : May 19, 2020
INVENTOR(S) : Lei Xiao et al.

Page 1 of 1

It is certified that error appears in the above-identified patent and that said Letters Patent is hereby corrected as shown below:

In the Claims

Column 113, Line 23, Claim 3, change "The isolated nucleic acid sequence of claim 1" to --The CAR of claim 1--.

Column 114, Line 26, Claim 18, change ", where" to --, wherein--.

Signed and Sealed this
First Day of September, 2020

Andrei Iancu
*Director of the United States Patent and Trademark Office*

SEQUENCE LISTING

```
<160> NUMBER OF SEQ ID NOS: 45

<210> SEQ ID NO 1
<211> LENGTH: 21
<212> TYPE: PRT
<213> ORGANISM: Artificial Sequence
<220> FEATURE:
<223> OTHER INFORMATION: synthetic

<400> SEQUENCE: 1

Met Ala Leu Pro Val Thr Ala Leu Leu Leu Pro Leu Ala Leu Leu Leu
1               5                   10                  15

His Ala Ala Arg Pro
            20

<210> SEQ ID NO 2
<211> LENGTH: 237
<212> TYPE: PRT
<213> ORGANISM: Artificial Sequence
<220> FEATURE:
<223> OTHER INFORMATION: synthetic

<400> SEQUENCE: 2

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45
```

Tyr Val Ala Thr Asn Leu Ala Asp Gly Val Pro Ser Arg Phe Ser Gly
            50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Tyr
                85                  90                  95

Thr Phe Gly Gly Gly Thr Lys Leu Gly Gly Gly Ser Gly Gly
            100                 105                 110

Gly Ser Gly Gly Gly Gly Ser Glu Val Gln Leu Gln Gln Ser Gly Ala
            115                 120                 125

Glu Leu Val Lys Pro Gly Ala Ser Val Lys Leu Ser Cys Thr Ala Ser
130                 135                 140

Gly Phe Asn Ile Asn Asp Thr Tyr Met His Trp Val Lys Gln Arg Pro
145                 150                 155                 160

Glu Gln Gly Leu Glu Trp Ile Gly Arg Ile Asp Pro Ala Asn Gly Asn
                165                 170                 175

Thr Lys Tyr Asp Pro Lys Phe Gln Gly Lys Ala Thr Ile Thr Ala Asp
            180                 185                 190

Thr Ser Ser Asn Thr Ala Tyr Leu Gln Leu Ser Ser Leu Thr Ser Glu
            195                 200                 205

Asp Thr Ala Val Tyr Tyr Cys Ala Arg Gly Ala Arg Gly Ser Arg Phe
210                 215                 220

Ala Tyr Trp Gly Gln Gly Thr Leu Val Thr Val Ser Ala
225                 230                 235

<210> SEQ ID NO 3
<211> LENGTH: 104
<212> TYPE: PRT
<213> ORGANISM: Artificial Sequence
<220> FEATURE:
<223> OTHER INFORMATION: synthetic

<400> SEQUENCE: 3

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
                20                  25                  30

Leu Ala Trp Tyr Gln Gln Lys Gln Gly Lys Ser Pro Gln Leu Leu Val
            35                  40                  45

Tyr Val Ala Thr Asn Leu Ala Asp Gly Val Pro Ser Arg Phe Ser Gly
            50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Tyr
                85                  90                  95

Thr Phe Gly Gly Gly Thr Lys Leu
            100

<210> SEQ ID NO 4
<211> LENGTH: 118
<212> TYPE: PRT
<213> ORGANISM: Artificial Sequence
<220> FEATURE:
<223> OTHER INFORMATION: synthetic

<400> SEQUENCE: 4

Glu Val Gln Leu Gln Gln Ser Gly Ala Glu Leu Val Lys Pro Gly Ala
1               5                   10                  15

```
Ser Val Lys Leu Ser Cys Thr Ala Ser Gly Phe Asn Ile Asn Asp Thr
             20                  25                  30

Tyr Met His Trp Val Lys Gln Arg Pro Glu Gln Gly Leu Glu Trp Ile
         35                  40                  45

Gly Arg Ile Asp Pro Ala Asn Gly Asn Thr Lys Tyr Asp Pro Lys Phe
 50                  55                  60

Gln Gly Lys Ala Thr Ile Thr Ala Asp Thr Ser Ser Asn Thr Ala Tyr
 65                  70                  75                  80

Leu Gln Leu Ser Ser Leu Thr Ser Glu Asp Thr Ala Val Tyr Tyr Cys
                 85                  90                  95

Ala Arg Gly Ala Arg Gly Ser Arg Phe Ala Tyr Trp Gly Gln Gly Thr
            100                 105                 110

Leu Val Thr Val Ser Ala
            115
```

<210> SEQ ID NO 5
<211> LENGTH: 244
<212> TYPE: PRT
<213> ORGANISM: Artificial Sequence
<220> FEATURE:
<223> OTHER INFORMATION: synthetic

<400> SEQUENCE: 5

```
Gln Ser Val Leu Thr Gln Pro Pro Ser Val Ser Ala Ala Pro Gly Gln
 1               5                  10                  15

Lys Val Thr Ile Ser Cys Ser Gly Ser Ser Ser Asp Ile Gly Ser Asn
             20                  25                  30

Tyr Val Ser Trp Tyr Gln Gln Phe Pro Gly Thr Ala Pro Lys Leu Leu
         35                  40                  45

Ile Tyr Asp Asn Asn Lys Arg Pro Ser Ala Ile Pro Asp Arg Phe Ser
 50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Arg Leu
                 85                  90                  95

Gly Ile Ala Val Phe Gly Gly Gly Thr Gln Leu Thr Val Leu Gly Gly
            100                 105                 110

Gly Gly Ser Gly Gly Gly Ser Gly Gly Gly Ser Glu Val Gln
            115                 120                 125

Leu Val Gln Ser Gly Ala Glu Val Lys Lys Pro Gly Gln Ser Leu Lys
            130                 135                 140

Ile Ser Cys Lys Ala Ser Gly Tyr Ser Leu Thr Asp Asn Trp Ile Gly
145                 150                 155                 160

Trp Val Arg Gln Lys Pro Gly Lys Gly Leu Glu Trp Met Gly Ile Ile
                165                 170                 175

Tyr Pro Gly Asp Ser Asp Thr Arg Tyr Ser Pro Ser Phe Gln Gly Gln
            180                 185                 190

Val Thr Ile Ser Ala Asp Lys Ser Ile Asn Thr Ala Tyr Leu Gln Trp
            195                 200                 205

Ser Ser Leu Lys Ala Ser Asp Thr Ala Ile Tyr Tyr Cys Val Gly Leu
            210                 215                 220

Asp Trp Asn Tyr Asn Pro Leu Arg Tyr Trp Gly Pro Gly Thr Leu Val
225                 230                 235                 240

Thr Val Ser Ser
```

<210> SEQ ID NO 6
<211> LENGTH: 110
<212> TYPE: PRT
<213> ORGANISM: Artificial Sequence
<220> FEATURE:
<223> OTHER INFORMATION: synthetic

<400> SEQUENCE: 6

```
Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asp Ile Gly Ser Asn
            20                  25                  30

Tyr Val Ser Trp Tyr Gln Gln Phe Pro Gly Thr Ala Pro Lys Leu Leu
        35                  40                  45

Ile Tyr Asp Asn Asn Lys Arg Pro Ser Ala Ile Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Arg Leu
                85                  90                  95

Gly Ile Ala Val Phe Gly Gly Gly Thr Gln Leu Thr Val Leu
            100                 105                 110
```

<210> SEQ ID NO 7
<211> LENGTH: 119
<212> TYPE: PRT
<213> ORGANISM: Artificial Sequence
<220> FEATURE:
<223> OTHER INFORMATION: synthetic

<400> SEQUENCE: 7

```
Glu Val Gln Leu Val Gln Ser Gly Ala Glu Val Lys Lys Pro Gly Gln
1               5                   10                  15

Ser Leu Lys Ile Ser Cys Lys Ala Ser Gly Tyr Ser Leu Thr Asp Asn
            20                  25                  30

Trp Ile Gly Trp Val Arg Gln Lys Pro Gly Lys Gly Leu Glu Trp Met
        35                  40                  45

Gly Ile Ile Tyr Pro Gly Asp Ser Asp Thr Arg Tyr Ser Pro Ser Phe
50                  55                  60

Gln Gly Gln Val Thr Ile Ser Ala Asp Lys Ser Ile Asn Thr Ala Tyr
65                  70                  75                  80

Leu Gln Trp Ser Ser Leu Lys Ala Ser Asp Thr Ala Ile Tyr Tyr Cys
                85                  90                  95

Val Gly Leu Asp Trp Asn Tyr Asn Pro Leu Arg Tyr Trp Gly Pro Gly
            100                 105                 110

Thr Leu Val Thr Val Ser Ser
        115
```

<210> SEQ ID NO 8
<211> LENGTH: 252
<212> TYPE: PRT
<213> ORGANISM: Artificial Sequence
<220> FEATURE:
<223> OTHER INFORMATION: synthetic

<400> SEQUENCE: 8

```
Asp Ile Val Leu Thr Gln Ser Pro Ala Ser Leu Ala Val Ser Leu Gly
1               5                   10                  15

Gln Gly Ala Thr Ile Ser Cys Arg Ala Ser Lys Ser Val Ser Thr Ser
```

```
            20                  25                  30
Gly Tyr Thr Tyr Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Gly
                85                  90                  95

Glu Leu Pro Pro Ser Phe Gly Gly Gly Thr Lys Leu Glu Ile Lys Arg
            100                 105                 110

Ala Gly Gly Gly Gly Ser Gly Gly Gly Gly Ser Gly Gly Gly Gly Ser
            115                 120                 125

Glu Val Gln Leu Val Glu Ser Gly Gly Asp Leu Val Lys Pro Gly Gly
            130                 135                 140

Ser Leu Lys Leu Ser Cys Ala Val Ser Gly Phe Thr Phe Ser Ser Tyr
145                 150                 155                 160

Gly Met Ser Trp Val Arg Gln Thr Pro Asp Lys Arg Leu Glu Trp Val
                165                 170                 175

Ala Thr Val Ser Ser Gly Gly Thr Tyr Thr Tyr Tyr Pro Asp Ser Val
                180                 185                 190

Lys Gly Arg Phe Thr Ile Ser Arg Asp Asn Ala Lys Asn Thr Leu Tyr
                195                 200                 205

Leu Gln Met Ser Ser Leu Lys Ser Glu Asp Ser Ala Met Tyr Tyr Cys
            210                 215                 220

Ala Arg His Arg Gly Asn Tyr Tyr Ala Thr Tyr Tyr Ala Met Asp
225                 230                 235                 240

Tyr Trp Gly Gln Gly Thr Ser Val Thr Val Ser Ser
                245                 250
```

<210> SEQ ID NO 9
<211> LENGTH: 113
<212> TYPE: PRT
<213> ORGANISM: Artificial Sequence
<220> FEATURE:
<223> OTHER INFORMATION: synthetic

<400> SEQUENCE: 9

```
Asp Ile Val Leu Thr Gln Ser Pro Ala Ser Leu Ala Val Ser Leu Gly
1               5                   10                  15

Gln Gly Ala Thr Ile Ser Cys Arg Ala Ser Lys Ser Val Ser Thr Ser
            20                  25                  30

Gly Tyr Thr Tyr Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Gly
                85                  90                  95

Glu Leu Pro Pro Ser Phe Gly Gly Gly Thr Lys Leu Glu Ile Lys Arg
            100                 105                 110

Ala
```

<210> SEQ ID NO 10

<211> LENGTH: 124
<212> TYPE: PRT
<213> ORGANISM: Artificial Sequence
<220> FEATURE:
<223> OTHER INFORMATION: synthetic

<400> SEQUENCE: 10

```
Glu Val Gln Leu Val Glu Ser Gly Gly Asp Leu Val Lys Pro Gly Gly
1               5                   10                  15
Ser Leu Lys Leu Ser Cys Ala Val Ser Gly Phe Thr Phe Ser Ser Tyr
            20                  25                  30
Gly Met Ser Trp Val Arg Gln Thr Pro Asp Lys Arg Leu Glu Trp Val
        35                  40                  45
Ala Thr Val Ser Ser Gly Gly Thr Tyr Thr Tyr Tyr Pro Asp Ser Val
    50                  55                  60
Lys Gly Arg Phe Thr Ile Ser Arg Asp Asn Ala Lys Asn Thr Leu Tyr
65                  70                  75                  80
Leu Gln Met Ser Ser Leu Lys Ser Glu Asp Ser Ala Met Tyr Tyr Cys
                85                  90                  95
Ala Arg His Arg Gly Asn Tyr Tyr Ala Thr Tyr Tyr Tyr Ala Met Asp
            100                 105                 110
Tyr Trp Gly Gln Gly Thr Ser Val Thr Val Ser Ser
        115                 120
```

<210> SEQ ID NO 11
<211> LENGTH: 243
<212> TYPE: PRT
<213> ORGANISM: Artificial Sequence
<220> FEATURE:
<223> OTHER INFORMATION: synthetic

<400> SEQUENCE: 11

```
Asp Val Gln Ile Thr Gln Ser Pro Ser Tyr Leu Ala Ala Ser Pro Gly
1               5                   10                  15
Glu Thr Ile Thr Ile Asn Cys Arg Ala Ser Lys Ser Ile Ser Lys Tyr
            20                  25                  30
Leu Ala Trp Tyr Gln Glu Lys Pro Gly Lys Thr Asn Lys Leu Leu Ile
        35                  40                  45
Tyr Ser Gly Ser Thr Leu Gln Ser Gly Ile Pro Ser Arg Phe Ser Gly
    50                  55                  60
Ser Gly Ser Gly Thr Asp Phe Thr Leu Thr Ile Ser Ser Leu Glu Pro
65                  70                  75                  80
Glu Asp Phe Ala Met Tyr Tyr Cys Gln Gln His His Glu Tyr Pro Tyr
                85                  90                  95
Thr Phe Gly Gly Gly Thr Lys Leu Glu Ile Lys Gly Gly Gly Gly Ser
            100                 105                 110
Gly Gly Gly Gly Ser Gly Gly Gly Ser Gln Val Gln Leu Gln Gln
        115                 120                 125
Pro Gly Ala Glu Leu Val Arg Pro Gly Ala Ser Val Lys Leu Ser Cys
    130                 135                 140
Lys Ala Ser Gly Tyr Thr Phe Thr Thr Tyr Trp Met Asn Trp Val Lys
145                 150                 155                 160
Gln Arg Pro Glu Gln Gly Leu Glu Trp Ile Gly Arg Ile Asp Pro Tyr
                165                 170                 175
Asp Ser Glu Thr His Tyr Asn Gln Lys Phe Lys Asp Lys Ala Ile Leu
            180                 185                 190
Thr Val Asp Lys Ser Ser Ser Thr Ala Tyr Met Gln Leu Ser Ser Leu
```

```
                 195                 200                 205
Thr Ser Glu Asp Ser Ala Val Tyr Tyr Cys Ala Arg Gly Pro Tyr Tyr
    210                 215                 220
Gly Thr Asn Pro Trp Phe Pro Tyr Trp Gly Gln Gly Thr Leu Val Thr
225                 230                 235                 240
Val Ser Ser

<210> SEQ ID NO 12
<211> LENGTH: 107
<212> TYPE: PRT
<213> ORGANISM: Artificial Sequence
<220> FEATURE:
<223> OTHER INFORMATION: synthetic

<400> SEQUENCE: 12

Asp Val Gln Ile Thr Gln Ser Pro Ser Tyr Leu Ala Ala Ser Pro Gly
1               5                   10                  15
Glu Thr Ile Thr Ile Asn Cys Arg Ala Ser Lys Ser Ile Ser Lys Tyr
            20                  25                  30
Leu Ala Trp Tyr Gln Glu Lys Pro Gly Lys Thr Asn Lys Leu Leu Ile
        35                  40                  45
Tyr Ser Gly Ser Thr Leu Gln Ser Gly Ile Pro Ser Arg Phe Ser Gly
    50                  55                  60
Ser Gly Ser Gly Thr Asp Phe Thr Leu Thr Ile Ser Ser Leu Glu Pro
65                  70                  75                  80
Glu Asp Phe Ala Met Tyr Tyr Cys Gln Gln His His Glu Tyr Pro Tyr
                85                  90                  95
Thr Phe Gly Gly Gly Thr Lys Leu Glu Ile Lys
            100                 105

<210> SEQ ID NO 13
<211> LENGTH: 121
<212> TYPE: PRT
<213> ORGANISM: Artificial Sequence
<220> FEATURE:
<223> OTHER INFORMATION: synthetic

<400> SEQUENCE: 13

Gln Val Gln Leu Gln Gln Pro Gly Ala Glu Leu Val Arg Pro Gly Ala
1               5                   10                  15
Ser Val Lys Leu Ser Cys Lys Ala Ser Gly Tyr Thr Phe Thr Thr Tyr
            20                  25                  30
Trp Met Asn Trp Val Lys Gln Arg Pro Glu Gln Gly Leu Glu Trp Ile
        35                  40                  45
Gly Arg Ile Asp Pro Tyr Asp Ser Glu Thr His Tyr Asn Gln Lys Phe
    50                  55                  60
Lys Asp Lys Ala Ile Leu Thr Val Asp Lys Ser Ser Ser Thr Ala Tyr
65                  70                  75                  80
Met Gln Leu Ser Ser Leu Thr Ser Glu Asp Ser Ala Val Tyr Tyr Cys
                85                  90                  95
Ala Arg Gly Pro Tyr Tyr Gly Thr Asn Pro Trp Phe Pro Tyr Trp Gly
            100                 105                 110
Gln Gly Thr Leu Val Thr Val Ser Ser
        115                 120

<210> SEQ ID NO 14
<211> LENGTH: 241
<212> TYPE: PRT
```

<213> ORGANISM: Artificial Sequence
<220> FEATURE:
<223> OTHER INFORMATION: synthetic

<400> SEQUENCE: 14

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Arg Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Gly Ser Leu Gln Ser
65                  70                  75                  80

Glu Asp Phe Ala Val Tyr Tyr Cys Gln Gln Tyr Lys Thr Trp Pro Arg
                85                  90                  95

Thr Phe Gly Gln Gly Thr Asn Val Glu Ile Lys Gly Gly Gly Gly Ser
            100                 105                 110

Gly Gly Gly Gly Ser Gly Gly Gly Ser Gln Val Gln Leu Gln Gln
        115                 120                 125

Trp Gly Ala Gly Leu Leu Lys Pro Ser Glu Thr Leu Ser Leu Thr Cys
130                 135                 140

Ala Val Phe Gly Gly Ser Phe Ser Gly Tyr Tyr Trp Ser Trp Ile Arg
145                 150                 155                 160

Gln Pro Pro Gly Lys Gly Leu Glu Trp Ile Gly Glu Ile Asn His Arg
                165                 170                 175

Gly Asn Thr Asn Asp Asn Pro Ser Leu Lys Ser Arg Val Thr Ile Ser
            180                 185                 190

Val Asp Thr Ser Lys Asn Gln Phe Ala Leu Lys Leu Ser Ser Val Thr
        195                 200                 205

Ala Ala Asp Thr Ala Val Tyr Tyr Cys Ala Arg Glu Arg Gly Tyr Thr
    210                 215                 220

Tyr Gly Asn Phe Asp His Trp Gly Gln Gly Thr Leu Val Thr Val Ser
225                 230                 235                 240

Ser
```

<210> SEQ ID NO 15
<211> LENGTH: 107
<212> TYPE: PRT
<213> ORGANISM: Artificial Sequence
<220> FEATURE:
<223> OTHER INFORMATION: synthetic

<400> SEQUENCE: 15

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Arg Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Gly Ser Leu Gln Ser
65                  70                  75                  80

Glu Asp Phe Ala Val Tyr Tyr Cys Gln Gln Tyr Lys Thr Trp Pro Arg
```

```
                    85                  90                  95

Thr Phe Gly Gln Gly Thr Asn Val Glu Ile Lys
                100                 105

<210> SEQ ID NO 16
<211> LENGTH: 119
<212> TYPE: PRT
<213> ORGANISM: Artificial Sequence
<220> FEATURE:
<223> OTHER INFORMATION: synthetic

<400> SEQUENCE: 16

Gln Val Gln Leu Gln Gln Trp Gly Ala Gly Leu Leu Lys Pro Ser Glu
1               5                   10                  15

Thr Leu Ser Leu Thr Cys Ala Val Phe Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Asn Thr Asn Asp Asn Pro Ser Leu Lys
    50                  55                  60

Ser Arg Val Thr Ile Ser Val Asp Thr Ser Lys Asn Gln Phe Ala Leu
65                  70                  75                  80

Lys Leu Ser Ser Val Thr Ala Ala Asp Thr Ala Val Tyr Tyr Cys Ala
                85                  90                  95

Arg Glu Arg Gly Tyr Thr Tyr Gly Asn Phe Asp His Trp Gly Gln Gly
            100                 105                 110

Thr Leu Val Thr Val Ser Ser
        115

<210> SEQ ID NO 17
<211> LENGTH: 246
<212> TYPE: PRT
<213> ORGANISM: Artificial Sequence
<220> FEATURE:
<223> OTHER INFORMATION: synthetic

<400> SEQUENCE: 17

Asp Val Val Met Thr Gln Thr Pro Leu Ser Leu Pro Val Arg Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asn Phe Thr Leu Lys Ile
65                  70                  75                  80

Ser Arg Val Glu Ala Glu Asp Leu Gly Leu Tyr Phe Cys Ser Gln Ser
                85                  90                  95

Thr His Val Pro Tyr Thr Phe Gly Gly Gly Thr Lys Leu Glu Ile Lys
            100                 105                 110

Arg Ala Gly Gly Gly Gly Ser Gly Gly Gly Ser Gly Gly Gly Gly
        115                 120                 125

Ser Gln Val Gln Leu Arg Gln Ser Gly Pro Glu Leu Val Lys Pro Gly
    130                 135                 140

Ala Ser Val Lys Met Ser Cys Lys Ala Ser Gly Tyr Thr Phe Thr Asp
145                 150                 155                 160
```

```
Tyr Val Ile Ser Trp Val Lys Gln Arg Thr Gly Gln Gly Leu Glu Trp
                165                 170                 175

Ile Gly Asp Ile Tyr Pro Gly Ser Gly Tyr Ser Phe Tyr Asn Glu Asn
            180                 185                 190

Phe Lys Gly Lys Ala Thr Leu Thr Ala Asp Lys Ser Ser Thr Thr Ala
        195                 200                 205

Tyr Met Gln Leu Ser Ser Leu Thr Ser Glu Asp Ser Ala Val Tyr Phe
    210                 215                 220

Cys Ala Thr Tyr Tyr Asn Tyr Pro Phe Ala Tyr Trp Gly Gln Gly Thr
225                 230                 235                 240

Leu Val Thr Val Ser Ala
                245
```

<210> SEQ ID NO 18
<211> LENGTH: 114
<212> TYPE: PRT
<213> ORGANISM: Artificial Sequence
<220> FEATURE:
<223> OTHER INFORMATION: synthetic

<400> SEQUENCE: 18

```
Asp Val Val Met Thr Gln Thr Pro Leu Ser Leu Pro Val Arg Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asn Phe Thr Leu Lys Ile
65                  70                  75                  80

Ser Arg Val Glu Ala Glu Asp Leu Gly Leu Tyr Phe Cys Ser Gln Ser
                85                  90                  95

Thr His Val Pro Tyr Thr Phe Gly Gly Gly Thr Lys Leu Glu Ile Lys
            100                 105                 110

Arg Ala
```

<210> SEQ ID NO 19
<211> LENGTH: 117
<212> TYPE: PRT
<213> ORGANISM: Artificial Sequence
<220> FEATURE:
<223> OTHER INFORMATION: synthetic

<400> SEQUENCE: 19

```
Gln Val Gln Leu Arg Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Val Ile Ser Trp Val Lys Gln Arg Thr Gly Gln Gly Leu Glu Trp Ile
        35                  40                  45

Gly Asp Ile Tyr Pro Gly Ser Gly Tyr Ser Phe Tyr Asn Glu Asn Phe
    50                  55                  60

Lys Gly Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Phe Cys
                85                  90                  95
```

```
Ala Thr Tyr Tyr Asn Tyr Pro Phe Ala Tyr Trp Gly Gln Gly Thr Leu
                100                 105                 110
Val Thr Val Ser Ala
        115

<210> SEQ ID NO 20
<211> LENGTH: 199
<212> TYPE: PRT
<213> ORGANISM: Artificial Sequence
<220> FEATURE:
<223> OTHER INFORMATION: synthetic

<400> SEQUENCE: 20

Leu Pro Ile Cys Pro Gly Gly Ala Ala Arg Cys Gln Val Thr Leu Arg
1               5                   10                  15
Asp Leu Phe Asp Arg Ala Val Val Leu Ser His Tyr Ile His Asn Leu
                20                  25                  30
Ser Ser Glu Met Phe Ser Glu Phe Asp Lys Arg Tyr Thr His Gly Arg
            35                  40                  45
Gly Phe Ile Thr Lys Ala Ile Asn Ser Cys His Thr Ser Ser Leu Ala
        50                  55                  60
Thr Pro Glu Asp Lys Glu Gln Ala Gln Gln Met Asn Gln Lys Asp Phe
65                  70                  75                  80
Leu Ser Leu Ile Val Ser Ile Leu Arg Ser Trp Asn Glu Pro Leu Tyr
                85                  90                  95
His Leu Val Thr Glu Val Arg Gly Met Gln Glu Ala Pro Glu Ala Ile
                100                 105                 110
Leu Ser Lys Ala Val Glu Ile Glu Gln Thr Lys Arg Leu Leu Glu
            115                 120                 125
Gly Met Glu Leu Ile Val Ser Gln Val His Pro Glu Thr Lys Glu Asn
        130                 135                 140
Glu Ile Tyr Pro Val Trp Ser Gly Leu Pro Ser Leu Gln Met Ala Asp
145                 150                 155                 160
Glu Glu Ser Arg Leu Ser Ala Tyr Tyr Asn Leu Leu His Cys Leu Arg
                165                 170                 175
Arg Asp Ser His Lys Ile Asp Asn Tyr Leu Lys Leu Leu Lys Cys Arg
                180                 185                 190
Ile Ile His Asn Asn Asn Cys
        195

<210> SEQ ID NO 21
<211> LENGTH: 69
<212> TYPE: PRT
<213> ORGANISM: Artificial Sequence
<220> FEATURE:
<223> OTHER INFORMATION: synthetic

<400> SEQUENCE: 21

Ala Lys Pro Thr Thr Thr Pro Ala Pro Arg Pro Pro Thr Pro Ala Pro
1               5                   10                  15
Thr Ile Ala Ser Gln Pro Leu Ser Leu Arg Pro Glu Ala Cys Arg Pro
                20                  25                  30
Ala Ala Gly Gly Ala Val His Thr Arg Gly Leu Asp Phe Ala Cys Asp
            35                  40                  45
Ile Tyr Ile Trp Ala Pro Leu Ala Gly Thr Cys Gly Val Leu Leu Leu
        50                  55                  60
Ser Leu Val Ile Thr
65
```

<210> SEQ ID NO 22
<211> LENGTH: 42
<212> TYPE: PRT
<213> ORGANISM: Artificial Sequence
<220> FEATURE:
<223> OTHER INFORMATION: synthetic

<400> SEQUENCE: 22

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 23
<211> LENGTH: 112
<212> TYPE: PRT
<213> ORGANISM: Artificial Sequence
<220> FEATURE:
<223> OTHER INFORMATION: synthetic

<400> SEQUENCE: 23

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 24
<211> LENGTH: 1746
<212> TYPE: DNA
<213> ORGANISM: Artificial Sequence
<220> FEATURE:
<223> OTHER INFORMATION: synthetic

<400> SEQUENCE: 24
atgcagcgcc cgggccccg cctgtggctg gtcctgcagg tgatgggctc gtgcgccgcc      60
atcagctcca tggacatgga gcgcccgggc gacggcaaat gccagcccat cgagatcccg     120
atgtgcaagg acatcggcta caacatgact cgtatgccca acctgatggg ccacgagaac    180
cagcgcgagg cagccatcca gttgcacgag ttcgcgccgc tggtggagta cggctgccac    240
ggccacctcc gcttcttcct gtgctcgctg tacgcgccga tgtgcaccga gcaggtctct    300 accccccatcc ccgcctgccg ggtcatgtgc gagcaggccc ggctcaagtg ctcccccgatt    360 atggagcagt tcaacttcaa gtggcccgac tccctggact gccggaaact ccccaacaag    420
aacgacccca actacctgtg catggaggcg cccaacaacg ctcggacga gcccaccccgg    480 ggctcgggcc tgttcccgcc gctgttccgg ccgcagcggc cccacagcgc gcaggagcac    540

```
ccgctgaagg acggggcccc cgggcgcggc ggctgcgaca acccgggcaa gttccaccac    600
gtggagaaga gcgcgtcgtg cgcgccgctc tgcacgcccg gcgtggacgt gtactggagc    660
cgcgaggaca agcgcttcgc agtggtctgg ctggccatct gggcggtgct gtgcttcttc    720
tccagcgcct tcaccgtgct caccttcctc atcgacccgg cccgcttccg ctaccccgag    780
cgccccatca tcttcctctc catgtgctac tgcgtctact ccgtgggcta cctcatccgc    840
ctcttcgccg cgccgagag catcgcctgc gaccgggaca cggccagct ctatgtcatc    900 caggagggac tggagagcac cggctgcacg ctggtcttcc tggtcctcta ctacttcggc    960
atggccagct cgctgtggtg ggtggtcctc acgctcacct ggttcctggc cgccggcaag   1020
aagtggggcc acgaggccat cgaagccaac agcagctact ccacctggc agcctgggcc   1080 atcccggcgg tgaagaccat cctgatcctg gtcatgcgca gggtggcggg ggacgagctc   1140
accggggtct gctacgtggg cagcatggac gtcaacgcgc tcaccggctt cgtgctcatt   1200
cccctggcct gctacctggt catcggcacg tccttcatcc tctcgggctt cgtggccctg   1260
ttccacatcc ggagggtgat gaagacgggc ggcgagaaca cggacaagct ggagaagctc   1320
atggtgcgta tcgggctctt ctctgtgctg tacaccgtgc cggccacctg tgtgatcgcc   1380
tgctactttt acgaacgcct caacatggat tactggaaga tcctggcggc gcagcacaag   1440
tgcaaaatga caaccagac taaaacgctg gactgcctga tggccgcctc catccccgcc   1500
gtggagatct tcatggtgaa gatctttatg ctgctggtgg tggggatcac cagcgggatg   1560
tggatttgga cctccaagac tctgcagtcc tggcagcagg tgtgcagccg taggttaaag   1620
aagaagagcc ggagaaaacc ggccagcgtg atcaccagcg gtgggattta caaaaaagcc   1680
cagcatcccc agaaaactca ccacgggaaa tatgagatcc ctgcccagtc gcccacctgc   1740
gtgtga                                                              1746
```

<210> SEQ ID NO 25
<211> LENGTH: 581
<212> TYPE: PRT
<213> ORGANISM: Artificial Sequence
<220> FEATURE:
<223> OTHER INFORMATION: synthetic

<400> SEQUENCE: 25

```
Met Gln Arg Pro Gly Pro Arg Leu Trp Leu Val Leu Gln Val Met Gly
1               5                   10                  15

Ser Cys Ala Ala Ile Ser Ser Met Asp Met Glu Arg Pro Gly Asp Gly
                20                  25                  30

Lys Cys Gln Pro Ile Glu Ile Pro Met Cys Lys Asp Ile Gly Tyr Asn
            35                  40                  45

Met Thr Arg Met Pro Asn Leu Met Gly His Glu Asn Gln Arg Glu Ala
        50                  55                  60

Ala Ile Gln Leu His Glu Phe Ala Pro Leu Val Glu Tyr Gly Cys His
65                  70                  75                  80

Gly His Leu Arg Phe Phe Leu Cys Ser Leu Tyr Ala Pro Met Cys Thr
                85                  90                  95

Glu Gln Val Ser Thr Pro Ile Pro Ala Cys Arg Val Met Cys Glu Gln
            100                 105                 110

Ala Arg Leu Lys Cys Ser Pro Ile Met Glu Gln Phe Asn Phe Lys Trp
        115                 120                 125

Pro Asp Ser Leu Asp Cys Arg Lys Leu Pro Asn Lys Asn Asp Pro Asn
    130                 135                 140
```

-continued

```
Tyr Leu Cys Met Glu Ala Pro Asn Asn Gly Ser Asp Glu Pro Thr Arg
145                 150                 155                 160

Gly Ser Gly Leu Phe Pro Leu Phe Arg Pro Gln Arg Pro His Ser
            165                 170                 175

Ala Gln Glu His Pro Leu Lys Asp Gly Pro Gly Arg Gly Gly Cys
            180                 185                 190

Asp Asn Pro Gly Lys Phe His His Val Glu Lys Ser Ala Ser Cys Ala
            195                 200                 205

Pro Leu Cys Thr Pro Gly Val Asp Val Tyr Trp Ser Arg Glu Asp Lys
            210                 215                 220

Arg Phe Ala Val Val Trp Leu Ala Ile Trp Ala Val Leu Cys Phe Phe
225                 230                 235                 240

Ser Ser Ala Phe Thr Val Leu Thr Phe Leu Ile Asp Pro Ala Arg Phe
            245                 250                 255

Arg Tyr Pro Glu Arg Pro Ile Ile Phe Leu Ser Met Cys Tyr Cys Val
            260                 265                 270

Tyr Ser Val Gly Tyr Leu Ile Arg Leu Phe Ala Gly Ala Glu Ser Ile
            275                 280                 285

Ala Cys Asp Arg Asp Ser Gly Gln Leu Tyr Val Ile Gln Glu Gly Leu
290                 295                 300

Glu Ser Thr Gly Cys Thr Leu Val Phe Leu Val Leu Tyr Tyr Phe Gly
305                 310                 315                 320

Met Ala Ser Ser Leu Trp Trp Val Val Leu Thr Leu Thr Trp Phe Leu
            325                 330                 335

Ala Ala Gly Lys Lys Trp Gly His Glu Ala Ile Glu Ala Asn Ser Ser
            340                 345                 350

Tyr Phe His Leu Ala Ala Trp Ala Ile Pro Ala Val Lys Thr Ile Leu
            355                 360                 365

Ile Leu Val Met Arg Arg Val Ala Gly Asp Glu Leu Thr Gly Val Cys
            370                 375                 380

Tyr Val Gly Ser Met Asp Val Asn Ala Leu Thr Gly Phe Val Leu Ile
385                 390                 395                 400

Pro Leu Ala Cys Tyr Leu Val Ile Gly Thr Ser Phe Ile Leu Ser Gly
            405                 410                 415

Phe Val Ala Leu Phe His Ile Arg Arg Val Met Lys Thr Gly Gly Glu
            420                 425                 430

Asn Thr Asp Lys Leu Glu Lys Leu Met Val Arg Ile Gly Leu Phe Ser
            435                 440                 445

Val Leu Tyr Thr Val Pro Ala Thr Cys Val Ile Ala Cys Tyr Phe Tyr
450                 455                 460

Glu Arg Leu Asn Met Asp Tyr Trp Lys Ile Leu Ala Ala Gln His Lys
465                 470                 475                 480

Cys Lys Met Asn Asn Gln Thr Lys Thr Leu Asp Cys Leu Met Ala Ala
            485                 490                 495

Ser Ile Pro Ala Val Glu Ile Phe Met Val Lys Ile Phe Met Leu Leu
            500                 505                 510

Val Val Gly Ile Thr Ser Gly Met Trp Ile Trp Thr Ser Lys Thr Leu
            515                 520                 525

Gln Ser Trp Gln Gln Val Cys Ser Arg Arg Leu Lys Lys Lys Ser Arg
            530                 535                 540

Arg Lys Pro Ala Ser Val Ile Thr Ser Gly Gly Ile Tyr Lys Lys Ala
545                 550                 555                 560

Gln His Pro Gln Lys Thr His His Gly Lys Tyr Glu Ile Pro Ala Gln
```

Ser Pro Thr Cys Val
        580

<210> SEQ ID NO 26
<211> LENGTH: 2295
<212> TYPE: DNA
<213> ORGANISM: Artificial Sequence
<220> FEATURE:
<223> OTHER INFORMATION: synthetic

<400> SEQUENCE: 26

| | | | | | |
|---|---|---|---|---|---|
| atgaggccgg | cggacttgct | gcagctggtg | ctgctgctcg | acctgcccag | ggacctgggc | 60 |
| ggaatggggt | gttcgtctcc | accctgcgag | tgccatcagg | aggaggactt | cagagtcacc | 120 |
| tgcaaggata | ttcaacgcat | ccccagctta | ccgcccagta | cgcagactct | gaagcttatt | 180 |
| gagactcacc | tgagaactat | tccaagtcat | gcattttcta | atctgcccaa | tatttccaga | 240 |
| atctacgtat | ctatagatgt | gactctgcag | cagctggaat | cacactcctt | ctacaatttg | 300 |
| agtaaagtga | ctcacataga | aattcggaat | accaggaact | taacttacat | agaccctgat | 360 |
| gccctcaaag | agctccccct | cctaaagttc | cttggcattt | tcaacactgg | acttaaaatg | 420 |
| ttccctgacc | tgaccaaagt | ttattccact | gatatattct | ttatacttga | aattacagac | 480 |
| aacccttaca | tgacgtcaat | ccctgtgaat | gcttttcagg | actatgcaa | tgaaaccttg | 540 |
| acactgaagc | tgtacaacaa | tggctttact | tcagtccaag | gatatgcttt | caatgggaca | 600 |
| aagctggatc | tgtttacct | aaacaagaat | aaatacctga | cagttattga | caaagatgca | 660 |
| tttggaggag | tatacagtgg | accaagcttg | ctggacgtgt | ctcaaaccag | tgtcactgcc | 720 |
| cttccatcca | aaggcctgga | gcacctgaag | gaactgatag | caagaaacac | ctggactctt | 780 |
| aagaaacttc | cactttcctt | gagtttcctt | cacctcacac | gggctgacct | tcttacccca | 840 |
| agccactgct | gtgcttttaa | gaatcagaag | aaaatcagag | gaatccttga | gtccttgatg | 900 |
| tgtaatgaga | gcagtatgca | gagcttgcgc | cagagaaaat | ctgtgaatgc | cttgaatagc | 960 |
| cccctccacc | aggaatatga | agagaatctg | ggtgacagca | ttgttgggta | caaggaaaag | 1020 |
| tccaagttcc | aggatactca | taacaacgct | cattattacg | tcttctttga | agaacaagag | 1080 |
| gatgagatca | ttggttttgg | ccaggagctc | aaaaaccccc | aggaagagac | tctacaagct | 1140 |
| tttgacagcc | attatgacta | caccatatgt | ggggacagtg | aagacatggt | gtgtaccccc | 1200 |
| aagtccgatg | agttcaaccc | gtgtgaagac | ataatgggct | acaagttcct | gagaattgtg | 1260 |
| gtgtggttcg | ttagtctgct | ggctctcctg | ggcaatgtct | tgtcctgct | tattctcctc | 1320 |
| accagccact | acaaactgaa | cgtcccccgc | tttctcatgt | gcaacctggc | ctttgcggat | 1380 |
| ttctgcatgg | gatgtacct | gctcctcatc | gcctctgtag | acctctacac | tcactctgag | 1440 |
| tactacaacc | atgccatcga | ctggcagaca | ggccctgggt | gcaacacggc | tggtttcttc | 1500 |
| actgtctttg | caagcgagtt | atcggtgtat | acgctgacgg | tcatcaccct | ggagcgctgg | 1560 |
| tatgccatca | ccttcgccat | gcgcctggac | cggaagatcc | gcctcaggca | cgcatgtgcc | 1620 |
| atcatggttg | ggggctgggt | tgctgcttc | cttctcgccc | tgcttccttt | ggtgggaata | 1680 |
| agtagctatg | ccaaagtcag | tatctgcctg | cccatggaca | ccgagacccc | tcttgctctg | 1740 |
| gcatatattg | tttttgttct | gacgctcaac | atagttgcct | tcgtcatcgt | ctgctgctgt | 1800 |
| tatgtgaaga | tctacatcac | agtccgaaat | ccgcagtaca | acccaggga | caaagatacc | 1860 |
| aaaattgcca | agaggatggc | tgtgttgatc | ttcaccgact | tcatatgcat | ggcccaatc | 1920 |

```
tcattctatg ctctgtcagc aattctgaac aagcctctca tcactgttag caactccaaa    1980
atcttgctgg tactcttcta tccacttaac tcctgtgcca atccattcct ctatgctatt    2040
ttcaccaagg ccttccagag ggatgtgttc atcctactca gcaagtttgg catctgtaaa    2100
cgccaggctc aggcataccg ggggcagagg gttcctccaa agaacagcac tgatattcag    2160
gttcaaaagg ttacccacga gatgaggcag ggtctccaca acatggaaga tgtctatgaa    2220
ctgattgaaa actcccatct aaccccaaag aagcaaggcc aaatctcaga gagtatatg    2280 caaacggttt tgtaa    2295
```

<210> SEQ ID NO 27
<211> LENGTH: 764
<212> TYPE: PRT
<213> ORGANISM: Artificial Sequence
<220> FEATURE:
<223> OTHER INFORMATION: synthetic

<400> SEQUENCE: 27

```
Met Arg Pro Ala Asp Leu Leu Gln Leu Val Leu Leu Leu Asp Leu Pro
1               5                   10                  15

Arg Asp Leu Gly Gly Met Gly Cys Ser Ser Pro Pro Cys Glu Cys His
            20                  25                  30

Gln Glu Glu Asp Phe Arg Val Thr Cys Lys Asp Ile Gln Arg Ile Pro
        35                  40                  45

Ser Leu Pro Pro Ser Thr Gln Thr Leu Lys Leu Ile Glu Thr His Leu
    50                  55                  60

Arg Thr Ile Pro Ser His Ala Phe Ser Asn Leu Pro Asn Ile Ser Arg
65                  70                  75                  80

Ile Tyr Val Ser Ile Asp Val Thr Leu Gln Gln Leu Glu Ser His Ser
                85                  90                  95

Phe Tyr Asn Leu Ser Lys Val Thr His Ile Glu Ile Arg Asn Thr Arg
            100                 105                 110

Asn Leu Thr Tyr Ile Asp Pro Asp Ala Leu Lys Glu Leu Pro Leu Leu
        115                 120                 125

Lys Phe Leu Gly Ile Phe Asn Thr Gly Leu Lys Met Phe Pro Asp Leu
    130                 135                 140

Thr Lys Val Tyr Ser Thr Asp Ile Phe Phe Ile Leu Glu Ile Thr Asp
145                 150                 155                 160

Asn Pro Tyr Met Thr Ser Ile Pro Val Asn Ala Phe Gln Gly Leu Cys
                165                 170                 175

Asn Glu Thr Leu Thr Leu Lys Leu Tyr Asn Asn Gly Phe Thr Ser Val
            180                 185                 190

Gln Gly Tyr Ala Phe Asn Gly Thr Lys Leu Asp Ala Val Tyr Leu Asn
        195                 200                 205

Lys Asn Lys Tyr Leu Thr Val Ile Asp Lys Asp Ala Phe Gly Gly Val
    210                 215                 220

Tyr Ser Gly Pro Ser Leu Leu Asp Val Ser Gln Thr Ser Val Thr Ala
225                 230                 235                 240

Leu Pro Ser Lys Gly Leu Glu His Leu Lys Glu Leu Ile Ala Arg Asn
                245                 250                 255

Thr Trp Thr Leu Lys Lys Leu Pro Ser Leu Ser Phe Leu His Leu
            260                 265                 270

Thr Arg Ala Asp Leu Ser Tyr Pro Ser His Cys Cys Ala Phe Lys Asn
        275                 280                 285

Gln Lys Lys Ile Arg Gly Ile Leu Glu Ser Leu Met Cys Asn Glu Ser
```

```
        290                 295                 300
Ser Met Gln Ser Leu Arg Gln Arg Lys Ser Val Asn Ala Leu Asn Ser
305                 310                 315                 320

Pro Leu His Gln Glu Tyr Glu Asn Leu Gly Asp Ser Ile Val Gly
                325                 330                 335

Tyr Lys Glu Lys Ser Lys Phe Gln Asp Thr His Asn Asn Ala His Tyr
                340                 345                 350

Tyr Val Phe Phe Glu Glu Gln Glu Asp Glu Ile Ile Gly Phe Gly Gln
            355                 360                 365

Glu Leu Lys Asn Pro Gln Glu Glu Thr Leu Gln Ala Phe Asp Ser His
        370                 375                 380

Tyr Asp Tyr Thr Ile Cys Gly Asp Ser Glu Asp Met Val Cys Thr Pro
385                 390                 395                 400

Lys Ser Asp Glu Phe Asn Pro Cys Glu Asp Ile Met Gly Tyr Lys Phe
                405                 410                 415

Leu Arg Ile Val Val Trp Phe Val Ser Leu Leu Ala Leu Leu Gly Asn
                420                 425                 430

Val Phe Val Leu Leu Ile Leu Leu Thr Ser His Tyr Lys Leu Asn Val
            435                 440                 445

Pro Arg Phe Leu Met Cys Asn Leu Ala Phe Ala Asp Phe Cys Met Gly
        450                 455                 460

Met Tyr Leu Leu Leu Ile Ala Ser Val Asp Leu Tyr Thr His Ser Glu
465                 470                 475                 480

Tyr Tyr Asn His Ala Ile Asp Trp Gln Thr Gly Pro Gly Cys Asn Thr
                485                 490                 495

Ala Gly Phe Phe Thr Val Phe Ala Ser Glu Leu Ser Val Tyr Thr Leu
            500                 505                 510

Thr Val Ile Thr Leu Glu Arg Trp Tyr Ala Ile Thr Phe Ala Met Arg
            515                 520                 525

Leu Asp Arg Lys Ile Arg Leu Arg His Ala Cys Ala Ile Met Val Gly
        530                 535                 540

Gly Trp Val Cys Cys Phe Leu Leu Ala Leu Leu Pro Leu Val Gly Ile
545                 550                 555                 560

Ser Ser Tyr Ala Lys Val Ser Ile Cys Leu Pro Met Asp Thr Glu Thr
                565                 570                 575

Pro Leu Ala Leu Ala Tyr Ile Val Phe Val Leu Thr Leu Asn Ile Val
            580                 585                 590

Ala Phe Val Ile Val Cys Cys Cys Tyr Val Lys Ile Tyr Ile Thr Val
            595                 600                 605

Arg Asn Pro Gln Tyr Asn Pro Gly Asp Lys Asp Thr Lys Ile Ala Lys
        610                 615                 620

Arg Met Ala Val Leu Ile Phe Thr Asp Phe Ile Cys Met Ala Pro Ile
625                 630                 635                 640

Ser Phe Tyr Ala Leu Ser Ala Ile Leu Asn Lys Pro Leu Ile Thr Val
                645                 650                 655

Ser Asn Ser Lys Ile Leu Leu Val Leu Phe Tyr Pro Leu Asn Ser Cys
            660                 665                 670

Ala Asn Pro Phe Leu Tyr Ala Ile Phe Thr Lys Ala Phe Gln Arg Asp
        675                 680                 685

Val Phe Ile Leu Leu Ser Lys Phe Gly Ile Cys Lys Arg Gln Ala Gln
        690                 695                 700

Ala Tyr Arg Gly Gln Arg Val Pro Pro Lys Asn Ser Thr Asp Ile Gln
705                 710                 715                 720
```

```
Val Gln Lys Val Thr His Glu Met Arg Gln Gly Leu His Asn Met Glu
                725                 730                 735

Asp Val Tyr Glu Leu Ile Glu Asn Ser His Leu Thr Pro Lys Lys Gln
            740                 745                 750

Gly Gln Ile Ser Glu Glu Tyr Met Gln Thr Val Leu
        755                 760
```

<210> SEQ ID NO 28
<211> LENGTH: 1869
<212> TYPE: DNA
<213> ORGANISM: Artificial Sequence
<220> FEATURE:
<223> OTHER INFORMATION: synthetic

<400> SEQUENCE: 28

| | | |
|---|---|---|
| atgaaggaaa atgtggcatc tgcaaccgtt tcactctgc tacttttct caacacctgc | 60 |
| cttctgaatg acagttacc tcctggaaaa cctgagatct ttaaatgtcg ttctcccaat | 120 |
| aaggaaacat tcacctgctg gtggaggcct gggacagatg gaggacttcc taccaattat | 180 |
| tcactgactt accacaggga aggagagaca ctcatgcatg aatgtccaga ctacataacc | 240 |
| ggtggcccca actcctgcca cttggcaag cagtacacct ccatgtggag acatacatc | 300 |
| atgatggtca atgccactaa ccagatggga agcagtttct cggatgaact ttatgtggac | 360 |
| gtgacttaca tagttcagcc agaccctcct ttggagctgg ctgtggaagt aaaacagcca | 420 |
| gaagacagaa acccctacct gtggattaaa tggtctccac ctaccctgat tgacttaaaa | 480 |
| actggttggt tcacgctcct gtatgaaatt cgattaaaac ccgagaaagc agctgagtgg | 540 |
| gagatccatt tgctgggca gcaaacagag tttaagattc tcagcctaca tccaggacag | 600 |
| aaataccttg tccaggttcg ctgcaaacca gaccatggat actggagtgc atggagtcca | 660 |
| gcgaccttca ttcagatacc tagtgacttc accatgaatg atacaaccgt tggatctct | 720 |
| gtggctgtcc tttctgctgt catctgtttg attattgtct gggcagtggc tttgaagggc | 780 |
| tatagcatgg tgacctgcat cttccgcca gttcctgggc aaaaataaa aggatttgat | 840 |
| gctcatctgt tggagaaggg caagtctgaa gaactactga gtgccttggg atgccaagac | 900 |
| tttcctccca cttctgacta tgaggacttg ctggtggagt atttagaagt agatgatagt | 960 |
| gaggaccagc atctaatgtc agtccattca aagaacacc caagtcaagg tatgaaccc | 1020 |
| acatacctgg atcctgacac tgactcaggc cgggggagct gtgacagccc ttcccttttg | 1080 |
| tctgaaaagt gtgaggaacc ccaggccaat ccctccacat ctatgatcc tgaggtcatt | 1140 |
| gagaagccag agaatcctga acaacccac acctgggacc cccagtgcat aagcatggaa | 1200 |
| ggcaaaatcc cctattttca tgctggtgga tccaaatgtt caacatggcc cttaccacag | 1260 |
| cccagccagc acaaccccag atcctcttac acaatatta ctgatgtgtg tgagctggct | 1320 |
| gtgggccctg caggtgcacc ggccactctg ttgaatgaag caggtaaaga tgctttaaaa | 1380 |
| tcctctcaaa ccattaagtc tagagaagag ggaaaggcaa cccagcagag ggaggtagaa | 1440 |
| agcttccatt ctgagactga ccaggatacg ccctggctgc tgcccagga gaaacccc | 1500 |
| tttggctccg ctaaacccct tggattatgtg gagattcaca ggtcaacaa agatggtgca | 1560 |
| ttatcattgc taccaaaaca gagagagaac agcggcaagc caagaagcc cgggactcct | 1620 |
| gagaacaata aggagtatgc caaggtgtcc ggggtcatgg ataacaacat cctggtgttg | 1680 |
| gtgccagatc cacatgctaa aaacgtggct tgctttgaag aatcagccaa agaggcccca | 1740 |
| ccatcacttg aacagaatca agctgagaaa gccctggcca acttcactgc aacatcaagc | 1800 |

```
aagtgcaggc tccagctggg tggtttggat tacctggatc ccgcatgttt tacacactcc   1860
tttcactga                                                           1869

<210> SEQ ID NO 29
<211> LENGTH: 622
<212> TYPE: PRT
<213> ORGANISM: Artificial Sequence
<220> FEATURE:
<223> OTHER INFORMATION: synthetic

<400> SEQUENCE: 29

Met Lys Glu Asn Val Ala Ser Ala Thr Val Phe Thr Leu Leu Leu Phe
1               5                   10                  15

Leu Asn Thr Cys Leu Leu Asn Gly Gln Leu Pro Pro Gly Lys Pro Glu
            20                  25                  30

Ile Phe Lys Cys Arg Ser Pro Asn Lys Glu Thr Phe Thr Cys Trp Trp
        35                  40                  45

Arg Pro Gly Thr Asp Gly Gly Leu Pro Thr Asn Tyr Ser Leu Thr Tyr
    50                  55                  60

His Arg Glu Gly Glu Thr Leu Met His Glu Cys Pro Asp Tyr Ile Thr
65                  70                  75                  80

Gly Gly Pro Asn Ser Cys His Phe Gly Lys Gln Tyr Thr Ser Met Trp
                85                  90                  95

Arg Thr Tyr Ile Met Met Val Asn Ala Thr Asn Gln Met Gly Ser Ser
            100                 105                 110

Phe Ser Asp Glu Leu Tyr Val Asp Val Thr Tyr Ile Val Gln Pro Asp
        115                 120                 125

Pro Pro Leu Glu Leu Ala Val Glu Val Lys Gln Pro Glu Asp Arg Lys
    130                 135                 140

Pro Tyr Leu Trp Ile Lys Trp Ser Pro Pro Thr Leu Ile Asp Leu Lys
145                 150                 155                 160

Thr Gly Trp Phe Thr Leu Leu Tyr Glu Ile Arg Leu Lys Pro Glu Lys
                165                 170                 175

Ala Ala Glu Trp Glu Ile His Phe Ala Gly Gln Gln Thr Glu Phe Lys
            180                 185                 190

Ile Leu Ser Leu His Pro Gly Gln Lys Tyr Leu Val Gln Val Arg Cys
        195                 200                 205

Lys Pro Asp His Gly Tyr Trp Ser Ala Trp Ser Pro Ala Thr Phe Ile
    210                 215                 220

Gln Ile Pro Ser Asp Phe Thr Met Asn Asp Thr Thr Val Trp Ile Ser
225                 230                 235                 240

Val Ala Val Leu Ser Ala Val Ile Cys Leu Ile Ile Val Trp Ala Val
                245                 250                 255

Ala Leu Lys Gly Tyr Ser Met Val Thr Cys Ile Phe Pro Pro Val Pro
            260                 265                 270

Gly Pro Lys Ile Lys Gly Phe Asp Ala His Leu Leu Glu Lys Gly Lys
        275                 280                 285

Ser Glu Glu Leu Leu Ser Ala Leu Gly Cys Gln Asp Phe Pro Pro Thr
    290                 295                 300

Ser Asp Tyr Glu Asp Leu Leu Val Glu Tyr Leu Glu Val Asp Asp Ser
305                 310                 315                 320

Glu Asp Gln His Leu Met Ser Val His Ser Lys Glu His Pro Ser Gln
                325                 330                 335

Gly Met Lys Pro Thr Tyr Leu Asp Pro Asp Thr Asp Ser Gly Arg Gly
```

|   |   |   | 340 |   |   |   |   | 345 |   |   |   |   | 350 |   |   |
|---|---|---|---|---|---|---|---|---|---|---|---|---|---|---|---|
| Ser | Cys | Asp | Ser | Pro | Ser | Leu | Leu | Ser | Glu | Lys | Cys | Glu | Glu | Pro | Gln |
|   |   |   | 355 |   |   |   |   | 360 |   |   |   |   | 365 |   |   |

Ser Cys Asp Ser Pro Ser Leu Leu Ser Glu Lys Cys Glu Glu Pro Gln
   355                 360                 365

Ala Asn Pro Ser Thr Phe Tyr Asp Pro Glu Val Ile Glu Lys Pro Glu
370                 375                 380

Asn Pro Glu Thr Thr His Thr Trp Asp Pro Gln Cys Ile Ser Met Glu
385                 390                 395                 400

Gly Lys Ile Pro Tyr Phe His Ala Gly Gly Ser Lys Cys Ser Thr Trp
            405                 410                 415

Pro Leu Pro Gln Pro Ser Gln His Asn Pro Arg Ser Ser Tyr His Asn
                420                 425                 430

Ile Thr Asp Val Cys Glu Leu Ala Val Gly Pro Ala Gly Ala Pro Ala
            435                 440                 445

Thr Leu Leu Asn Glu Ala Gly Lys Asp Ala Leu Lys Ser Ser Gln Thr
        450                 455                 460

Ile Lys Ser Arg Glu Glu Gly Lys Ala Thr Gln Gln Arg Glu Val Glu
465                 470                 475                 480

Ser Phe His Ser Glu Thr Asp Gln Asp Thr Pro Trp Leu Leu Pro Gln
                485                 490                 495

Glu Lys Thr Pro Phe Gly Ser Ala Lys Pro Leu Asp Tyr Val Glu Ile
            500                 505                 510

His Lys Val Asn Lys Asp Gly Ala Leu Ser Leu Leu Pro Lys Gln Arg
        515                 520                 525

Glu Asn Ser Gly Lys Pro Lys Lys Pro Gly Thr Pro Glu Asn Asn Lys
    530                 535                 540

Glu Tyr Ala Lys Val Ser Gly Val Met Asp Asn Asn Ile Leu Val Leu
545                 550                 555                 560

Val Pro Asp Pro His Ala Lys Asn Val Ala Cys Phe Glu Glu Ser Ala
                565                 570                 575

Lys Glu Ala Pro Pro Ser Leu Glu Gln Asn Gln Ala Glu Lys Ala Leu
            580                 585                 590

Ala Asn Phe Thr Ala Thr Ser Ser Lys Cys Arg Leu Gln Leu Gly Gly
        595                 600                 605

Leu Asp Tyr Leu Asp Pro Ala Cys Phe Thr His Ser Phe His
610                 615                 620

<210> SEQ ID NO 30
<211> LENGTH: 1212
<212> TYPE: DNA
<213> ORGANISM: Artificial Sequence
<220> FEATURE:
<223> OTHER INFORMATION: synthetic

<400> SEQUENCE: 30

| atgcctaggc caggcacaat ggctctgtgc ctgctgaccc tggtgctgtc cctgctgcca | 60 |
| cctcaggctg ctgccacaaa caccacaatc aagtccaacc ccacatctac ccaacagtg | 120 |
| cccaggacca caacctgctt cggcgatgga tgtcagaaca cagcttctag atgcaagaac | 180 |
| ggcggaacct gggacggcct gaagtgccag tgtcctaacc tgtactacgg agagctgtgc | 240 |
| gaggaggtgg tgagctccat cgatatcggc cacccgaga caatctctgc ccagatggag | 300 |
| ctgaccgtga cagtgaccag cgtgaagttc accgaggagc tgaagaacca ctctagccag | 360 |
| gagttccagg agtttaagca gaccttcacc gagcagatga catcgtgta ctctggcatc | 420 |
| cctgagtacg tgggagtgaa catcaccaag ctgcggctgg aagcgtggt ggtggagcac | 480 |

```
gatgtgctgc tgcgcacaaa gtacacccca gagtacaaga cagtgctgga caacgctacc    540
gaggtggtga aggagaagat cacaaaggtg acaacccagc agatcatgat caacgatatc    600
tgcagcgaca tgatgtgctt caacacaacc ggaacccagg tgcagaacat cacagtgacc    660
cagtacgatc cagaggagga ctgccggaag atggccaagg agtacggcga ttacttcgtg    720
gtggagtacc gcgaccagaa gccctactgc atctcccctt gtgagccagg attttccgtg    780
tctaagaact gcaacctggg caagtgtcag atgagcctgt ccggaccaca gtgcctgtgc    840
gtgacaaccg agacacactg gtactccggc gagacatgta accagggaac ccagaagtct    900
ctggtgtacg gcctggtggg cgctggagtg gtgctgatgc tgatcatcct ggtggccctg    960
ctgatgctgg tgtttaggtc taagagagag gtgaagaggc agaagtacag actgagccag   1020
ctgtacaagt ggcaggagga ggattccgga ccagctcctg gaacattcca gaacatcgga   1080
tttgacatct gtcaggacga tgcagcatc cacctggagt ctatctacag caacttccag    1140
ccctccctga cacacatcga ccctgagaca aagatccgga tccagcgccc tcaggtcatg   1200
acaacctcct tt                                                      1212
```

<210> SEQ ID NO 31
<211> LENGTH: 404
<212> TYPE: PRT
<213> ORGANISM: Artificial Sequence
<220> FEATURE:
<223> OTHER INFORMATION: synthetic

<400> SEQUENCE: 31

```
Met Pro Arg Pro Gly Thr Met Ala Leu Cys Leu Leu Thr Leu Val Leu
1               5                   10                  15

Ser Leu Pro Pro Gln Ala Ala Thr Asn Thr Thr Ile Lys Ser
            20                  25                  30

Asn Pro Thr Ser Thr Pro Thr Val Pro Arg Thr Thr Cys Phe Gly
        35                  40                  45

Asp Gly Cys Gln Asn Thr Ala Ser Arg Cys Lys Asn Gly Gly Thr Trp
    50                  55                  60

Asp Gly Leu Lys Cys Gln Cys Pro Asn Leu Tyr Tyr Gly Glu Leu Cys
65                  70                  75                  80

Glu Glu Val Val Ser Ser Ile Asp Ile Gly Pro Pro Glu Thr Ile Ser
                85                  90                  95

Ala Gln Met Glu Leu Thr Val Thr Val Thr Ser Val Lys Phe Thr Glu
            100                 105                 110

Glu Leu Lys Asn His Ser Ser Gln Glu Phe Gln Glu Phe Lys Gln Thr
        115                 120                 125

Phe Thr Glu Gln Met Asn Ile Val Tyr Ser Gly Ile Pro Glu Tyr Val
    130                 135                 140

Gly Val Asn Ile Thr Lys Leu Arg Leu Gly Ser Val Val Val Glu His
145                 150                 155                 160

Asp Val Leu Leu Arg Thr Lys Tyr Thr Pro Glu Tyr Lys Thr Val Leu
                165                 170                 175

Asp Asn Ala Thr Glu Val Val Lys Glu Lys Ile Thr Lys Val Thr Thr
            180                 185                 190

Gln Gln Ile Met Ile Asn Asp Ile Cys Ser Asp Met Met Cys Phe Asn
        195                 200                 205

Thr Thr Gly Thr Gln Val Gln Asn Ile Thr Val Thr Gln Tyr Asp Pro
    210                 215                 220

Glu Glu Asp Cys Arg Lys Met Ala Lys Glu Tyr Gly Asp Tyr Phe Val
```

```
                225                 230                 235                 240
Val Glu Tyr Arg Asp Gln Lys Pro Tyr Cys Ile Ser Pro Cys Glu Pro
                    245                 250                 255

Gly Phe Ser Val Ser Lys Asn Cys Asn Leu Gly Lys Cys Gln Met Ser
                260                 265                 270

Leu Ser Gly Pro Gln Cys Leu Cys Val Thr Thr Glu Thr His Trp Tyr
            275                 280                 285

Ser Gly Glu Thr Cys Asn Gln Gly Thr Gln Lys Ser Leu Val Tyr Gly
        290                 295                 300

Leu Val Gly Ala Gly Val Val Leu Met Leu Ile Ile Leu Val Ala Leu
305                 310                 315                 320

Leu Met Leu Val Phe Arg Ser Lys Arg Glu Val Lys Arg Gln Lys Tyr
                325                 330                 335

Arg Leu Ser Gln Leu Tyr Lys Trp Gln Glu Glu Asp Ser Gly Pro Ala
            340                 345                 350

Pro Gly Thr Phe Gln Asn Ile Gly Phe Asp Ile Cys Gln Asp Asp Asp
        355                 360                 365

Ser Ile His Leu Glu Ser Ile Tyr Ser Asn Phe Gln Pro Ser Leu Arg
    370                 375                 380

His Ile Asp Pro Glu Thr Lys Ile Arg Ile Gln Arg Pro Gln Val Met
385                 390                 395                 400

Thr Thr Ser Phe

<210> SEQ ID NO 32
<211> LENGTH: 3222
<212> TYPE: DNA
<213> ORGANISM: Artificial Sequence
<220> FEATURE:
<223> OTHER INFORMATION: synthetic

<400> SEQUENCE: 32
atgaagacgt tgctgttgga cttggctttg tggtcactgc tcttccagcc cgggtggctg      60
tcctttagtt cccaggtgag tcagaactgc acaatggca gctatgaaat cagcgtcctg     120
atgatgggca actcagcctt tgcagagccc tgaaaaact tggaagatgc ggtgaatgag     180
gggctggaaa tagtgagagg acgtctgcaa atgctggcc taaatgtgac tgtgaacgct     240
actttcatgt attcggatgg tctgattcat aactcaggcg actgccgag tagcaccctgt     300 gaaggcctcg acctactcag gaaaatttca atgcacaac ggatgggctg tgtcctcata     360
gggccctcat gtacatactc caccttccag atgtaccttg acacagaatt gagctacccc    420
atgatctcag ctggaagttt tggattgtca tgtgactata agaaaccttt aaccaggctg    480
atgtctccag ctagaaagtt gatgtacttc ttggttaact tttggaaaac caacgatctg    540 ccccttcaaaa cttattcctg gagcacttcg tatgtttaca gaatggtac agaaactgag    600 gactgtttct ggtaccttaa tgctctggag gctagcgttt cctatttctc ccacgaactc    660
ggctttaagg tggtgttaag acaagataag gagtttcagg atatcttaat ggaccacaac    720
aggaaaagca atgtgattat tatgtgtggt ggtccagagt tcctctacaa gctgaagggt    780
gaccgagcag tggctgaaga cattgtcatt attctagtgg atctttttca tgaccagtac    840
tttgaggaca atgtcacagc ccctgactat atgaaaaatg tccttgttct gacgctgtct    900
cctgggaatt cccttctaaa tagctcttc tccaggaatc tatcaccaac aaaacgagac    960
tttgctcttg cctatttgaa tggaatcctg ctctttggac atatgctgaa gatatttctt   1020
gaaaatggag aaaatattac cacccccaaa tttgctcatg ctttcaggaa tctcactttt   1080
```

```
gaagggtatg acggtccagt gaccttggat gactgggggg atgttgacag taccatggtg    1140
cttctgtata cctctgtgga caccaagaaa tacaaggttc ttttgaccta tgatacccac    1200
gtaaataaga cctatcctgt ggatatgagc cccacattca cttggaagaa ctctaaactt    1260
cctaatgata ttacaggccg gggccctcag atcctgatga ttgcagtctt caccctcact    1320
ggagctgtgg tgctgctcct gctcgtcgct ctcctgatgc tcagaaaata tagaaaagat    1380
tatgaacttc gtcagaaaaa atggtcccac attcctcctg aaatatcttt cctctggag     1440 accaatgaga ccaatcatgt tagcctcaag atcgatgatg acaaaagacg agatacaatc    1500
cagagactac gacagtgcaa atacgacaaa aagcgagtga ttctcaaaga tctcaagcac    1560
aatgatggta atttcactga aaaacagaag atagaattga caagttgct tcagattgac     1620 tattacaacc tgaccaagtt ctacggcaca gtgaacttg ataccatgat cttcggggtg     1680
atagaatact gtgagagagg atccctccgg gaagttttaa atgacacaat ttcctaccct    1740
gatggcacat tcatggattg ggagtttaag atctctgtct tgtatgacat tgctaaggga    1800
atgtcatatc tgcactccag taagacagaa gtccatggtc gtctgaaatc taccaactgc    1860
gtagtggaca gtagaatggt ggtgaagatc actgattttg gctgcaattc cattttacct    1920
ccaaaaaagg acctgtggac agctccagag cacctccgcc aagccaacat ctctcagaaa    1980
ggagatgtgt acagctatgg gatcatcgca caggagatca tcctgcggaa agaaaccttc    2040
tacactttga gctgtcggga ccggaatgag aagattttca gagtggaaaa ttccaatgga    2100
atgaaaccct tccgcccaga tttattcttg gaaacagcag aggaaaaaga gctagaagtg    2160
tacctacttg taaaaaactg ttgggaggaa gatccagaaa agagaccaga tttcaaaaaa    2220
attgagacta cacttgccaa gatatttgga ctttttcatg accaaaaaaa tgaaagctat    2280
atggatacct tgatccgacg tctacagcta tattctcgaa acctggaaca tctggtagag    2340
gaaaggacac agctgtacaa ggcagagagg gacagggctg acagacttaa ctttatgttg    2400
cttccaaggc tagtggtaaa gtctctgaag gagaaaggct tgtggagcc ggaactatat      2460 gaggaagtta caatctactt cagtgacatt gtaggtttca ctactatctg caaatacagc    2520
accccccatg gaagtggtgga catgcttaat gacatctata gagttttga ccacattgtt    2580 gatcatcatg atgtctacaa ggtggaaacc atcggtgatg cgtacatggt ggctagtggt    2640
ttgcctaaga gaaatggcaa tcggcatgca atagacattg ccaagatggc cttggaaatc    2700
ctcagcttca tggggacctt tgagctggag catcttcctg cctcccaat atggattcgc     2760 attggagttc actctggtcc ctgtgctgct ggagttgtgg gaatcaagat gcctcgttat    2820
tgtctatttg gagatacggt caacacagcc tctaggatgg aatccactgg cctccctttg    2880
agaattcacg tgagtggctc caccatagcc atcctgaaga aactgagtg ccagttcctt      2940 tatgaagtga gaggagaaac atacttaaag ggaagaggaa atgagactac ctactggctg    3000
actgggatga aggaccagaa attcaacctg ccaaccctc ctactgtgga gatcaacag      3060 cgtttgcaag cagaattttc agacatgatt gccaactctt tacagaaaag acaggcagca    3120
gggataagaa gccaaaaacc cagacgggta gccagctata aaaaggcac tctggaatac     3180 ttgcagctga ataccacaga caaggagagc acctattttt aa                       3222
```

<210> SEQ ID NO 33
<211> LENGTH: 1073
<212> TYPE: PRT
<213> ORGANISM: Artificial Sequence
<220> FEATURE:

<223> OTHER INFORMATION: synthetic

<400> SEQUENCE: 33

```
Met Lys Thr Leu Leu Asp Leu Ala Leu Trp Ser Leu Leu Phe Gln
 1               5                  10                  15

Pro Gly Trp Leu Ser Phe Ser Ser Gln Val Ser Gln Asn Cys His Asn
             20                  25                  30

Gly Ser Tyr Glu Ile Ser Val Leu Met Met Gly Asn Ser Ala Phe Ala
             35                  40                  45

Glu Pro Leu Lys Asn Leu Glu Asp Ala Val Asn Glu Gly Leu Glu Ile
     50                  55                  60

Val Arg Gly Arg Leu Gln Asn Ala Gly Leu Asn Val Thr Val Asn Ala
 65                  70                  75                  80

Thr Phe Met Tyr Ser Asp Gly Leu Ile His Asn Ser Gly Asp Cys Arg
                 85                  90                  95

Ser Ser Thr Cys Glu Gly Leu Asp Leu Leu Arg Lys Ile Ser Asn Ala
                100                 105                 110

Gln Arg Met Gly Cys Val Leu Ile Gly Pro Ser Cys Thr Tyr Ser Thr
                115                 120                 125

Phe Gln Met Tyr Leu Asp Thr Glu Leu Ser Tyr Pro Met Ile Ser Ala
    130                 135                 140

Gly Ser Phe Gly Leu Ser Cys Asp Tyr Lys Glu Thr Leu Thr Arg Leu
145                 150                 155                 160

Met Ser Pro Ala Arg Lys Leu Met Tyr Phe Leu Val Asn Phe Trp Lys
                165                 170                 175

Thr Asn Asp Leu Pro Phe Lys Thr Tyr Ser Trp Ser Thr Ser Tyr Val
                180                 185                 190

Tyr Lys Asn Gly Thr Glu Thr Glu Asp Cys Phe Trp Tyr Leu Asn Ala
            195                 200                 205

Leu Glu Ala Ser Val Ser Tyr Phe Ser His Glu Leu Gly Phe Lys Val
    210                 215                 220

Val Leu Arg Gln Asp Lys Glu Phe Gln Asp Ile Leu Met Asp His Asn
225                 230                 235                 240

Arg Lys Ser Asn Val Ile Ile Met Cys Gly Gly Pro Glu Phe Leu Tyr
                245                 250                 255

Lys Leu Lys Gly Asp Arg Ala Val Ala Glu Asp Ile Val Ile Ile Leu
                260                 265                 270

Val Asp Leu Phe Asn Asp Gln Tyr Phe Glu Asp Asn Val Thr Ala Pro
    275                 280                 285

Asp Tyr Met Lys Asn Val Leu Val Leu Thr Leu Ser Pro Gly Asn Ser
    290                 295                 300

Leu Leu Asn Ser Ser Phe Ser Arg Asn Leu Ser Pro Thr Lys Arg Asp
305                 310                 315                 320

Phe Ala Leu Ala Tyr Leu Asn Gly Ile Leu Leu Phe Gly His Met Leu
                325                 330                 335

Lys Ile Phe Leu Glu Asn Gly Glu Asn Ile Thr Thr Pro Lys Phe Ala
                340                 345                 350

His Ala Phe Arg Asn Leu Thr Phe Glu Gly Tyr Asp Gly Pro Val Thr
    355                 360                 365

Leu Asp Asp Trp Gly Asp Val Asp Ser Thr Met Val Leu Leu Tyr Thr
    370                 375                 380

Ser Val Asp Thr Lys Lys Tyr Lys Val Leu Leu Thr Tyr Asp Thr His
385                 390                 395                 400
```

Val Asn Lys Thr Tyr Pro Val Asp Met Ser Pro Thr Phe Thr Trp Lys
            405                 410                 415

Asn Ser Lys Leu Pro Asn Asp Ile Thr Gly Arg Gly Pro Gln Ile Leu
            420                 425                 430

Met Ile Ala Val Phe Thr Leu Thr Gly Ala Val Val Leu Leu Leu Leu
            435                 440                 445

Val Ala Leu Leu Met Leu Arg Lys Tyr Arg Lys Asp Tyr Glu Leu Arg
450                 455                 460

Gln Lys Lys Trp Ser His Ile Pro Pro Glu Asn Ile Phe Pro Leu Glu
465                 470                 475                 480

Thr Asn Glu Thr Asn His Val Ser Leu Lys Ile Asp Asp Asp Lys Arg
            485                 490                 495

Arg Asp Thr Ile Gln Arg Leu Arg Gln Cys Lys Tyr Asp Lys Lys Arg
            500                 505                 510

Val Ile Leu Lys Asp Leu Lys His Asn Asp Gly Asn Phe Thr Glu Lys
            515                 520                 525

Gln Lys Ile Glu Leu Asn Lys Leu Leu Gln Ile Asp Tyr Tyr Asn Leu
            530                 535                 540

Thr Lys Phe Tyr Gly Thr Val Lys Leu Asp Thr Met Ile Phe Gly Val
545                 550                 555                 560

Ile Glu Tyr Cys Glu Arg Gly Ser Leu Arg Glu Val Leu Asn Asp Thr
            565                 570                 575

Ile Ser Tyr Pro Asp Gly Thr Phe Met Asp Trp Glu Phe Lys Ile Ser
            580                 585                 590

Val Leu Tyr Asp Ile Ala Lys Gly Met Ser Tyr Leu His Ser Ser Lys
            595                 600                 605

Thr Glu Val His Gly Arg Leu Lys Ser Thr Asn Cys Val Val Asp Ser
            610                 615                 620

Arg Met Val Val Lys Ile Thr Asp Phe Gly Cys Asn Ser Ile Leu Pro
625                 630                 635                 640

Pro Lys Lys Asp Leu Trp Thr Ala Pro Glu His Leu Arg Gln Ala Asn
            645                 650                 655

Ile Ser Gln Lys Gly Asp Val Tyr Ser Tyr Gly Ile Ile Ala Gln Glu
            660                 665                 670

Ile Ile Leu Arg Lys Glu Thr Phe Tyr Thr Leu Ser Cys Arg Asp Arg
            675                 680                 685

Asn Glu Lys Ile Phe Arg Val Glu Asn Ser Asn Gly Met Lys Pro Phe
            690                 695                 700

Arg Pro Asp Leu Phe Leu Glu Thr Ala Glu Glu Lys Glu Leu Glu Val
705                 710                 715                 720

Tyr Leu Leu Val Lys Asn Cys Trp Glu Glu Asp Pro Glu Lys Arg Pro
            725                 730                 735

Asp Phe Lys Lys Ile Glu Thr Thr Leu Ala Lys Ile Phe Gly Leu Phe
            740                 745                 750

His Asp Gln Lys Asn Glu Ser Tyr Met Asp Thr Leu Ile Arg Arg Leu
            755                 760                 765

Gln Leu Tyr Ser Arg Asn Leu Glu His Leu Val Glu Glu Arg Thr Gln
            770                 775                 780

Leu Tyr Lys Ala Glu Arg Asp Arg Ala Asp Arg Leu Asn Phe Met Leu
785                 790                 795                 800

Leu Pro Arg Leu Val Val Lys Ser Leu Lys Glu Lys Gly Phe Val Glu
            805                 810                 815

Pro Glu Leu Tyr Glu Glu Val Thr Ile Tyr Phe Ser Asp Ile Val Gly

```
                820                 825                 830
    Phe Thr Thr Ile Cys Lys Tyr Ser Thr Pro Met Glu Val Val Asp Met
                    835                 840                 845
    Leu Asn Asp Ile Tyr Lys Ser Phe Asp His Ile Val Asp His His Asp
        850                 855                 860
    Val Tyr Lys Val Glu Thr Ile Gly Asp Ala Tyr Met Val Ala Ser Gly
    865                 870                 875                 880
    Leu Pro Lys Arg Asn Gly Asn Arg His Ala Ile Asp Ile Ala Lys Met
                    885                 890                 895
    Ala Leu Glu Ile Leu Ser Phe Met Gly Thr Phe Glu Leu Glu His Leu
        900                 905                 910
    Pro Gly Leu Pro Ile Trp Ile Arg Ile Gly Val His Ser Gly Pro Cys
        915                 920                 925
    Ala Ala Gly Val Val Gly Ile Lys Met Pro Arg Tyr Cys Leu Phe Gly
        930                 935                 940
    Asp Thr Val Asn Thr Ala Ser Arg Met Glu Ser Thr Gly Leu Pro Leu
    945                 950                 955                 960
    Arg Ile His Val Ser Gly Ser Thr Ile Ala Ile Leu Lys Arg Thr Glu
                    965                 970                 975
    Cys Gln Phe Leu Tyr Glu Val Arg Gly Glu Thr Tyr Leu Lys Gly Arg
                    980                 985                 990
    Gly Asn Glu Thr Thr Tyr Trp Leu Thr Gly Met Lys Asp Gln Lys Phe
                    995                1000                1005
    Asn Leu Pro Thr Pro Pro Thr Val Glu Asn Gln Gln Arg Leu Gln
            1010                1015                1020
    Ala Glu Phe Ser Asp Met Ile Ala Asn Ser Leu Gln Lys Arg Gln
            1025                1030                1035
    Ala Ala Gly Ile Arg Ser Gln Lys Pro Arg Arg Val Ala Ser Tyr
            1040                1045                1050
    Lys Lys Gly Thr Leu Glu Tyr Leu Gln Leu Asn Thr Thr Asp Lys
            1055                1060                1065
    Glu Ser Thr Tyr Phe
            1070

<210> SEQ ID NO 34
<211> LENGTH: 987
<212> TYPE: DNA
<213> ORGANISM: Artificial Sequence
<220> FEATURE:
<223> OTHER INFORMATION: synthetic

<400> SEQUENCE: 34
atgactgtgg agaaggaggc ccctgatgcg cacttcactg tggacaaaca gaacatctcc        60
ctctggcccc gagagcctcc tcccaagtcc ggtccatctc tggtcccggg gaaaacaccc       120
acagtccgtg ctgcattaat ctgcctgacg ctggtcctgg tcgcctccgt cctgctgcag       180
gccgtccttt atccccggtt tatgggcacc atatcagatg taaagaccaa tgtccagttg       240
ctgaaaggtc gtgtggacaa catcagcacc ctggattctg aaattaaaaa gaatagtgac       300
ggcatggagg cagctggcgt tcagatccag atggtgaatg agagcctggg ttatgtgcgt       360
tctcagttcc tgaagttaaa aaccagtgtg gagaaggcca acgcacagat ccagatctta       420
acaagaagtt gggaagaagt cagtacctta aatgcccaaa tcccagagtt aaaaagtgat       480
ttggagaaag ccagtgcttt aaatacaaag atccgggcac tccagggcag cttgagaat        540 atgagcaagt tgctcaaacg acaaaatgat attctacagg tggtttctca aggctggaag       600
```

```
tacttcaagg ggaacttcta ttactttct ctcattccaa agacctggta tagtgccgag    660
cagttctgtg tgtccaggaa ttcacacctg acctcggtga cctcagagag tgagcaggag    720
tttctgtata aaacagcggg gggactcatc tactggattg gcctgactaa agcagggatg    780 gaagggact ggtcctgggt ggatgacacg ccattcaaca aggtccaaag tgtgaggttc    840
tggattccag gtgagcccaa caatgctggg aacaatgaac actgtggcaa tataaaggct    900
ccctcacttc aggcctggaa tgatgccca tgtgacaaaa cgtttctttt catttgtaag    960
cgaccctatg tcccatcaga accgtga                                       987
```

<210> SEQ ID NO 35
<211> LENGTH: 328
<212> TYPE: PRT
<213> ORGANISM: Artificial Sequence
<220> FEATURE:
<223> OTHER INFORMATION: synthetic

<400> SEQUENCE: 35

```
Met Thr Val Glu Lys Glu Ala Pro Asp Ala His Phe Thr Val Asp Lys
1               5                   10                  15

Gln Asn Ile Ser Leu Trp Pro Arg Glu Pro Pro Lys Ser Gly Pro
            20                  25                  30

Ser Leu Val Pro Gly Lys Thr Pro Thr Val Arg Ala Ala Leu Ile Cys
        35                  40                  45

Leu Thr Leu Val Leu Val Ala Ser Val Leu Gln Ala Val Leu Tyr
    50                  55                  60

Pro Arg Phe Met Gly Thr Ile Ser Asp Val Lys Thr Asn Val Gln Leu
65                  70                  75                  80

Leu Lys Gly Arg Val Asp Asn Ile Ser Thr Leu Asp Ser Glu Ile Lys
                85                  90                  95

Lys Asn Ser Asp Gly Met Glu Ala Ala Gly Val Gln Ile Gln Met Val
            100                 105                 110

Asn Glu Ser Leu Gly Tyr Val Arg Ser Gln Phe Leu Lys Leu Lys Thr
        115                 120                 125

Ser Val Glu Lys Ala Asn Ala Gln Ile Gln Ile Leu Thr Arg Ser Trp
    130                 135                 140

Glu Glu Val Ser Thr Leu Asn Ala Gln Ile Pro Glu Leu Lys Ser Asp
145                 150                 155                 160

Leu Glu Lys Ala Ser Ala Leu Asn Thr Lys Ile Arg Ala Leu Gln Gly
                165                 170                 175

Ser Leu Glu Asn Met Ser Lys Leu Leu Lys Arg Gln Asn Asp Ile Leu
            180                 185                 190

Gln Val Val Ser Gln Gly Trp Lys Tyr Phe Lys Gly Asn Phe Tyr Tyr
        195                 200                 205

Phe Ser Leu Ile Pro Lys Thr Trp Tyr Ser Ala Glu Gln Phe Cys Val
    210                 215                 220

Ser Arg Asn Ser His Leu Thr Ser Val Thr Ser Glu Ser Glu Gln Glu
225                 230                 235                 240

Phe Leu Tyr Lys Thr Ala Gly Gly Leu Ile Tyr Trp Ile Gly Leu Thr
                245                 250                 255

Lys Ala Gly Met Glu Gly Asp Trp Ser Trp Val Asp Asp Thr Pro Phe
            260                 265                 270

Asn Lys Val Gln Ser Val Arg Phe Trp Ile Pro Gly Glu Pro Asn Asn
        275                 280                 285
```

```
Ala Gly Asn Asn Glu His Cys Gly Asn Ile Lys Ala Pro Ser Leu Gln
    290                 295                 300

Ala Trp Asn Asp Ala Pro Cys Asp Lys Thr Phe Leu Phe Ile Cys Lys
305                 310                 315                 320

Arg Pro Tyr Val Pro Ser Glu Pro
                325
```

<210> SEQ ID NO 36
<211> LENGTH: 480
<212> TYPE: PRT
<213> ORGANISM: Artificial Sequence
<220> FEATURE:
<223> OTHER INFORMATION: synthetic

<400> SEQUENCE: 36

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ala Ser Leu
                20                  25                  30

Ser Val Ser Val Gly Glu Thr Val Thr Ile Thr Cys Arg Ala Ser Glu
            35                  40                  45

Asn Ile Tyr Ser Asn Leu Ala Trp Tyr Gln Gln Lys Gln Gly Lys Ser
    50                  55                  60

Pro Gln Leu Leu Val Tyr Val Ala Thr Asn Leu Ala Asp Gly Val Pro
65                  70                  75                  80

Ser Arg Phe Ser Gly Ser Gly Ser Gly Thr Gln Tyr Ser Leu Lys Ile
                85                  90                  95

Asn Ser Leu Gln Ser Glu Asp Phe Gly Ser Tyr Tyr Cys Gln His Phe
                100                 105                 110

Trp Gly Thr Pro Tyr Thr Phe Gly Gly Gly Thr Lys Leu Gly Gly Gly
            115                 120                 125

Ser Gly Gly Gly Gly Ser Gly Gly Gly Ser Glu Val Gln Leu Gln
    130                 135                 140

Gln Ser Gly Ala Glu Leu Val Lys Pro Gly Ala Ser Val Lys Leu Ser
145                 150                 155                 160

Cys Thr Ala Ser Gly Phe Asn Ile Asn Asp Thr Tyr Met His Trp Val
                165                 170                 175

Lys Gln Arg Pro Glu Gln Gly Leu Glu Trp Ile Gly Arg Ile Asp Pro
                180                 185                 190

Ala Asn Gly Asn Thr Lys Tyr Asp Pro Lys Phe Gln Gly Lys Ala Thr
            195                 200                 205

Ile Thr Ala Asp Thr Ser Ser Asn Thr Ala Tyr Leu Gln Leu Ser Ser
    210                 215                 220

Leu Thr Ser Glu Asp Thr Ala Val Tyr Tyr Cys Ala Arg Gly Ala Arg
225                 230                 235                 240

Gly Ser Arg Phe Ala Tyr Trp Gly Gln Gly Thr Leu Val Thr Val Ser
                245                 250                 255

Ala Ala Lys Pro Thr Thr Thr Pro Ala Pro Arg Pro Pro Thr Pro Ala
                260                 265                 270

Pro Thr Ile Ala Ser Gln Pro Leu Ser Leu Arg Pro Glu Ala Cys Arg
            275                 280                 285

Pro Ala Ala Gly Gly Ala Val His Thr Arg Gly Leu Asp Phe Ala Cys
    290                 295                 300

Asp Ile Tyr Ile Trp Ala Pro Leu Ala Gly Thr Cys Gly Val Leu Leu
305                 310                 315                 320
```

Leu Ser Leu Val Ile Thr Lys Arg Gly Arg Lys Leu Leu Tyr Ile
            325                 330                 335

Phe Lys Gln Pro Phe Met Arg Pro Val Gln Thr Thr Gln Glu Glu Asp
        340                 345                 350

Gly Cys Ser Cys Arg Phe Pro Glu Glu Glu Glu Gly Cys Glu Leu
            355                 360                 365

Arg Val Lys Phe Ser Arg Ser Ala Asp Ala Pro Ala Tyr Lys Gln Gly
370                 375                 380

Gln Asn Gln Leu Tyr Asn Glu Leu Asn Leu Gly Arg Arg Glu Glu Tyr
385                 390                 395                 400

Asp Val Leu Asp Lys Arg Arg Gly Arg Asp Pro Glu Met Gly Gly Lys
                405                 410                 415

Pro Arg Arg Lys Asn Pro Gln Glu Gly Leu Tyr Asn Glu Leu Gln Lys
                420                 425                 430

Asp Lys Met Ala Glu Ala Tyr Ser Glu Ile Gly Met Lys Gly Glu Arg
            435                 440                 445

Arg Arg Gly Lys Gly His Asp Gly Leu Tyr Gln Gly Leu Ser Thr Ala
            450                 455                 460

Thr Lys Asp Thr Tyr Asp Ala Leu His Met Gln Ala Leu Pro Pro Arg
465                 470                 475                 480

<210> SEQ ID NO 37
<211> LENGTH: 488
<212> TYPE: PRT
<213> ORGANISM: Artificial Sequence
<220> FEATURE:
<223> OTHER INFORMATION: synthetic

<400> SEQUENCE: 37

Met Ala Leu Pro Val Thr Ala Leu Leu Leu Pro Leu Ala Leu Leu Leu
1               5                   10                  15

His Ala Ala Arg Pro Gln Ser Val Leu Thr Gln Pro Pro Ser Val Ser
                20                  25                  30

Ala Ala Pro Gly Gln Lys Val Thr Ile Ser Cys Ser Gly Ser Ser Ser
            35                  40                  45

Asp Ile Gly Ser Asn Tyr Val Ser Trp Tyr Gln Gln Phe Pro Gly Thr
50                  55                  60

Ala Pro Lys Leu Leu Ile Tyr Asp Asn Asn Lys Arg Pro Ser Ala Ile
65                  70                  75                  80

Pro Asp Arg Phe Ser Gly Ser Lys Ser Gly Thr Ser Ala Thr Leu Gly
                85                  90                  95

Ile Thr Gly Leu Gln Thr Gly Asp Glu Ala Asp Tyr Tyr Cys Gly Thr
            100                 105                 110

Trp Asp Ser Arg Leu Gly Ile Ala Val Phe Gly Gly Gly Thr Gln Leu
        115                 120                 125

Thr Val Leu Gly Gly Gly Gly Ser Gly Gly Gly Ser Gly Gly Gly
130                 135                 140

Gly Ser Glu Val Gln Leu Val Gln Ser Gly Ala Glu Val Lys Lys Pro
145                 150                 155                 160

Gly Gln Ser Leu Lys Ile Ser Cys Lys Ala Ser Gly Tyr Ser Leu Thr
                165                 170                 175

Asp Asn Trp Ile Gly Trp Val Arg Gln Lys Pro Gly Lys Gly Leu Glu
            180                 185                 190

Trp Met Gly Ile Ile Tyr Pro Gly Asp Ser Asp Thr Arg Tyr Ser Pro
        195                 200                 205

```
Ser Phe Gln Gly Gln Val Thr Ile Ser Ala Asp Lys Ser Ile Asn Thr
    210                 215                 220
Ala Tyr Leu Gln Trp Ser Ser Leu Lys Ala Ser Asp Thr Ala Ile Tyr
225                 230                 235                 240
Tyr Cys Val Gly Leu Asp Trp Asn Tyr Asn Pro Leu Arg Tyr Trp Gly
                245                 250                 255
Pro Gly Thr Leu Val Thr Val Ser Ser Ala Lys Pro Thr Thr Thr Pro
            260                 265                 270
Ala Pro Arg Pro Pro Thr Pro Ala Pro Thr Ile Ala Ser Gln Pro Leu
        275                 280                 285
Ser Leu Arg Pro Glu Ala Cys Arg Pro Ala Ala Gly Gly Ala Val His
    290                 295                 300
Thr Arg Gly Leu Asp Phe Ala Cys Asp Ile Tyr Ile Trp Ala Pro Leu
305                 310                 315                 320
Ala Gly Thr Cys Gly Val Leu Leu Leu Ser Leu Val Ile Thr Lys Arg
                325                 330                 335
Gly Arg Lys Lys Leu Leu Tyr Ile Phe Lys Gln Pro Phe Met Arg Pro
            340                 345                 350
Val Gln Thr Thr Gln Glu Glu Asp Gly Cys Ser Cys Arg Phe Pro Glu
        355                 360                 365
Glu Glu Glu Gly Gly Cys Glu Leu Arg Val Lys Phe Ser Arg Ser Ala
    370                 375                 380
Asp Ala Pro Ala Tyr Lys Gln Gly Gln Asn Gln Leu Tyr Asn Glu Leu
385                 390                 395                 400
Asn Leu Gly Arg Arg Glu Glu Tyr Asp Val Leu Asp Lys Arg Arg Gly
                405                 410                 415
Arg Asp Pro Glu Met Gly Gly Lys Pro Arg Arg Lys Asn Pro Gln Glu
            420                 425                 430
Gly Leu Tyr Asn Glu Leu Gln Lys Asp Lys Met Ala Glu Ala Tyr Ser
        435                 440                 445
Glu Ile Gly Met Lys Gly Glu Arg Arg Arg Gly Lys Gly His Asp Gly
    450                 455                 460
Leu Tyr Gln Gly Leu Ser Thr Ala Thr Lys Asp Thr Tyr Asp Ala Leu
465                 470                 475                 480
His Met Gln Ala Leu Pro Pro Arg
                485

<210> SEQ ID NO 38
<211> LENGTH: 496
<212> TYPE: PRT
<213> ORGANISM: Artificial Sequence
<220> FEATURE:
<223> OTHER INFORMATION: synthetic

<400> SEQUENCE: 38

Met Ala Leu Pro Val Thr Ala Leu Leu Leu Pro Leu Ala Leu Leu Leu
1               5                   10                  15
His Ala Ala Arg Pro Asp Ile Val Leu Thr Gln Ser Pro Ala Ser Leu
            20                  25                  30
Ala Val Ser Leu Gly Gln Gly Ala Thr Ile Ser Cys Arg Ala Ser Lys
        35                  40                  45
Ser Val Ser Thr Ser Gly Tyr Thr Tyr Met His Trp Tyr Gln Gln Lys
    50                  55                  60
Pro Gly Gln Pro Pro Lys Leu Leu Ile Tyr Leu Ala Ser Asn Leu Glu
65                  70                  75                  80
```

```
Ser Gly Val Pro Ala Arg Phe Ser Gly Ser Gly Ser Gly Thr Asp Phe
                85                  90                  95

Thr Leu Asn Ile His Pro Val Glu Glu Glu Asp Ala Ala Thr Tyr Tyr
            100                 105                 110

Cys Gln His Ser Gly Glu Leu Pro Pro Ser Phe Gly Gly Gly Thr Lys
        115                 120                 125

Leu Glu Ile Lys Arg Ala Gly Gly Gly Ser Gly Gly Gly Gly Ser
130                 135                 140

Gly Gly Gly Ser Glu Val Gln Leu Val Glu Ser Gly Gly Asp Leu
145                 150                 155                 160

Val Lys Pro Gly Gly Ser Leu Lys Leu Ser Cys Ala Val Ser Gly Phe
                165                 170                 175

Thr Phe Ser Ser Tyr Gly Met Ser Trp Val Arg Gln Thr Pro Asp Lys
            180                 185                 190

Arg Leu Glu Trp Val Ala Thr Val Ser Ser Gly Gly Thr Tyr Thr Tyr
        195                 200                 205

Tyr Pro Asp Ser Val Lys Gly Arg Phe Thr Ile Ser Arg Asp Asn Ala
    210                 215                 220

Lys Asn Thr Leu Tyr Leu Gln Met Ser Ser Leu Lys Ser Glu Asp Ser
225                 230                 235                 240

Ala Met Tyr Tyr Cys Ala Arg His Arg Gly Asn Tyr Tyr Ala Thr Tyr
                245                 250                 255

Tyr Tyr Ala Met Asp Tyr Trp Gly Gln Gly Thr Ser Val Thr Val Ser
            260                 265                 270

Ser Ala Lys Pro Thr Thr Thr Pro Ala Pro Arg Pro Pro Thr Pro Ala
        275                 280                 285

Pro Thr Ile Ala Ser Gln Pro Leu Ser Leu Arg Pro Glu Ala Cys Arg
    290                 295                 300

Pro Ala Ala Gly Gly Ala Val His Thr Arg Gly Leu Asp Phe Ala Cys
305                 310                 315                 320

Asp Ile Tyr Ile Trp Ala Pro Leu Ala Gly Thr Cys Gly Val Leu Leu
                325                 330                 335

Leu Ser Leu Val Ile Thr Lys Arg Gly Arg Lys Lys Leu Leu Tyr Ile
            340                 345                 350

Phe Lys Gln Pro Phe Met Arg Pro Val Gln Thr Thr Gln Glu Glu Asp
        355                 360                 365

Gly Cys Ser Cys Arg Phe Pro Glu Glu Glu Glu Gly Gly Cys Glu Leu
    370                 375                 380

Arg Val Lys Phe Ser Arg Ser Ala Asp Ala Pro Ala Tyr Lys Gln Gly
385                 390                 395                 400

Gln Asn Gln Leu Tyr Asn Glu Leu Asn Leu Gly Arg Arg Glu Glu Tyr
                405                 410                 415

Asp Val Leu Asp Lys Arg Arg Gly Arg Asp Pro Glu Met Gly Gly Lys
            420                 425                 430

Pro Arg Arg Lys Asn Pro Gln Glu Gly Leu Tyr Asn Glu Leu Gln Lys
        435                 440                 445

Asp Lys Met Ala Glu Ala Tyr Ser Glu Ile Gly Met Lys Gly Glu Arg
    450                 455                 460

Arg Arg Gly Lys Gly His Asp Gly Leu Tyr Gln Gly Leu Ser Thr Ala
465                 470                 475                 480

Thr Lys Asp Thr Tyr Asp Ala Leu His Met Gln Ala Leu Pro Pro Arg
                485                 490                 495
```

```
<210> SEQ ID NO 39
<211> LENGTH: 487
<212> TYPE: PRT
<213> ORGANISM: Artificial Sequence
<220> FEATURE:
<223> OTHER INFORMATION: synthetic

<400> SEQUENCE: 39

Met Ala Leu Pro Val Thr Ala Leu Leu Leu Pro Leu Ala Leu Leu Leu
1               5                   10                  15

His Ala Ala Arg Pro Asp Val Gln Ile Thr Gln Ser Pro Ser Tyr Leu
            20                  25                  30

Ala Ala Ser Pro Gly Glu Thr Ile Thr Ile Asn Cys Arg Ala Ser Lys
        35                  40                  45

Ser Ile Ser Lys Tyr Leu Ala Trp Tyr Gln Glu Lys Pro Gly Lys Thr
50                  55                  60

Asn Lys Leu Leu Ile Tyr Ser Gly Ser Thr Leu Gln Ser Gly Ile Pro
65                  70                  75                  80

Ser Arg Phe Ser Gly Ser Gly Ser Gly Thr Asp Phe Thr Leu Thr Ile
                85                  90                  95

Ser Ser Leu Glu Pro Glu Asp Phe Ala Met Tyr Tyr Cys Gln Gln His
            100                 105                 110

His Glu Tyr Pro Tyr Thr Phe Gly Gly Gly Thr Lys Leu Glu Ile Lys
        115                 120                 125

Gly Gly Gly Gly Ser Gly Gly Gly Ser Gly Gly Gly Gly Ser Gln
130                 135                 140

Val Gln Leu Gln Gln Pro Gly Ala Glu Leu Val Arg Pro Gly Ala Ser
145                 150                 155                 160

Val Lys Leu Ser Cys Lys Ala Ser Gly Tyr Thr Phe Thr Thr Tyr Trp
                165                 170                 175

Met Asn Trp Val Lys Gln Arg Pro Glu Gln Gly Leu Glu Trp Ile Gly
            180                 185                 190

Arg Ile Asp Pro Tyr Asp Ser Glu Thr His Tyr Asn Gln Lys Phe Lys
        195                 200                 205

Asp Lys Ala Ile Leu Thr Val Asp Lys Ser Ser Ser Thr Ala Tyr Met
210                 215                 220

Gln Leu Ser Ser Leu Thr Ser Glu Asp Ser Ala Val Tyr Tyr Cys Ala
225                 230                 235                 240

Arg Gly Pro Tyr Tyr Gly Thr Asn Pro Trp Phe Pro Tyr Trp Gly Gln
                245                 250                 255

Gly Thr Leu Val Thr Val Ser Ser Ala Lys Pro Thr Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Lys Arg Gly
                325                 330                 335

Arg Lys Lys Leu Leu Tyr Ile Phe Lys Gln Pro Phe Met Arg Pro Val
            340                 345                 350

Gln Thr Thr Gln Glu Glu Asp Gly Cys Ser Cys Arg Phe Pro Glu Glu
        355                 360                 365

Glu Glu Gly Gly Cys Glu Leu Arg Val Lys Phe Ser Arg Ser Ala Asp
```

```
              370                 375                 380
Ala Pro Ala Tyr Lys Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Arg Lys Asn Pro Gln Glu Gly
            420                 425                 430

Leu Tyr Asn Glu Leu Gln Lys Asp Lys Met Ala Glu Ala Tyr Ser Glu
                435                 440                 445

Ile Gly Met Lys Gly Glu Arg Arg Arg Gly Lys Gly His Asp Gly Leu
            450                 455                 460

Tyr Gln Gly Leu Ser Thr Ala Thr Lys Asp Thr Tyr Asp Ala Leu His
465                 470                 475                 480

Met Gln Ala Leu Pro Pro Arg
                485

<210> SEQ ID NO 40
<211> LENGTH: 485
<212> TYPE: PRT
<213> ORGANISM: Artificial Sequence
<220> FEATURE:
<223> OTHER INFORMATION: synthetic

<400> SEQUENCE: 40

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
                20                  25                  30

Ser Val Ser Pro Gly Glu Arg Ala Thr Leu Ser Cys Arg Ala Ser Gln
            35                  40                  45

Ser Val Ser Arg Asn Leu Ala Trp Tyr Gln Gln Lys Pro Gly Gln Ala
        50                  55                  60

Pro Arg Leu Leu Ile Tyr Gly Ala Ser Thr Arg Ala Thr Gly Ile Pro
65                  70                  75                  80

Ala Arg Phe Ser Gly Ser Gly Ser Gly Thr Glu Phe Thr Leu Thr Ile
                85                  90                  95

Gly Ser Leu Gln Ser Glu Asp Phe Ala Val Tyr Tyr Cys Gln Gln Tyr
            100                 105                 110

Lys Thr Trp Pro Arg Thr Phe Gly Gln Gly Thr Asn Val Glu Ile Lys
        115                 120                 125

Gly Gly Gly Gly Ser Gly Gly Gly Ser Gly Gly Gly Gly Ser Gln
130                 135                 140

Val Gln Leu Gln Gln Trp Gly Ala Gly Leu Leu Lys Pro Ser Glu Thr
145                 150                 155                 160

Leu Ser Leu Thr Cys Ala Val Phe Gly Ser Phe Ser Gly Tyr Tyr
                165                 170                 175

Trp Ser Trp Ile Arg Gln Pro Pro Gly Lys Gly Leu Glu Trp Ile Gly
            180                 185                 190

Glu Ile Asn His Arg Gly Asn Thr Asn Asp Asn Pro Ser Leu Lys Ser
        195                 200                 205

Arg Val Thr Ile Ser Val Asp Thr Ser Lys Asn Gln Phe Ala Leu Lys
    210                 215                 220

Leu Ser Ser Val Thr Ala Ala Asp Thr Ala Val Tyr Tyr Cys Ala Arg
225                 230                 235                 240

Glu Arg Gly Tyr Thr Tyr Gly Asn Phe Asp His Trp Gly Gln Gly Thr
```

```
                    245                 250                 255
Leu Val Thr Val Ser Ser Ala Lys Pro Thr Thr Thr Pro Ala Pro Arg
            260                 265                 270

Pro Pro Thr Pro Ala Pro Thr Ile Ala Ser Gln Pro Leu Ser Leu Arg
            275                 280                 285

Pro Glu Ala Cys Arg Pro Ala Ala Gly Gly Ala Val His Thr Arg Gly
            290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Lys Arg Gly Arg Lys
            325                 330                 335

Lys Leu Leu Tyr Ile Phe Lys Gln Pro Phe Met Arg Pro Val Gln Thr
            340                 345                 350

Thr Gln Glu Glu Asp Gly Cys Ser Cys Arg Phe Pro Glu Glu Glu Glu
            355                 360                 365

Gly Gly Cys Glu Leu Arg Val Lys Phe Ser Arg Ser Ala Asp Ala Pro
            370                 375                 380

Ala Tyr Lys Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
            405                 410                 415

Glu Met Gly Gly Lys Pro Arg Arg Lys Asn Pro Gln Glu Gly Leu Tyr
            420                 425                 430

Asn Glu Leu Gln Lys Asp Lys Met Ala Glu Ala Tyr Ser Glu Ile Gly
            435                 440                 445

Met Lys Gly Glu Arg Arg Arg Gly Lys Gly His Asp Gly Leu Tyr Gln
            450                 455                 460

Gly Leu Ser Thr Ala Thr Lys Asp Thr Tyr Asp Ala Leu His Met Gln
465                 470                 475                 480

Ala Leu Pro Pro Arg
            485

<210> SEQ ID NO 41
<211> LENGTH: 490
<212> TYPE: PRT
<213> ORGANISM: Artificial Sequence
<220> FEATURE:
<223> OTHER INFORMATION: synthetic

<400> SEQUENCE: 41

Met Ala Leu Pro Val Thr Ala Leu Leu Leu Pro Leu Ala Leu Leu Leu
1               5                   10                  15

His Ala Ala Arg Pro Asp Val Val Met Thr Gln Thr Pro Leu Ser Leu
            20                  25                  30

Pro Val Arg Leu Gly Asp Gln Ala Ser Ile Ser Cys Arg Ser Ser Gln
            35                  40                  45

Ser Leu Val His Ser Asn Gly Asn Thr Tyr Leu His Trp Tyr Leu Gln
            50                  55                  60

Lys Pro Gly Gln Ser Pro Lys Leu Leu Ile Tyr Lys Val Ser Asn Arg
65                  70                  75                  80

Phe Ser Gly Val Pro Asp Arg Phe Ser Gly Ser Gly Ser Gly Thr Asn
            85                  90                  95

Phe Thr Leu Lys Ile Ser Arg Val Glu Ala Glu Asp Leu Gly Leu Tyr
            100                 105                 110

Phe Cys Ser Gln Ser Thr His Val Pro Tyr Thr Phe Gly Gly Gly Thr
```

```
            115                 120                 125
Lys Leu Glu Ile Lys Arg Ala Gly Gly Gly Ser Gly Gly Gly Gly
    130                 135                 140

Ser Gly Gly Gly Ser Gln Val Gln Leu Arg Gln Ser Gly Pro Glu
145                 150                 155                 160

Leu Val Lys Pro Gly Ala Ser Val Lys Met Ser Cys Lys Ala Ser Gly
                165                 170                 175

Tyr Thr Phe Thr Asp Tyr Val Ile Ser Trp Val Lys Gln Arg Thr Gly
            180                 185                 190

Gln Gly Leu Glu Trp Ile Gly Asp Ile Tyr Pro Gly Ser Gly Tyr Ser
                195                 200                 205

Phe Tyr Asn Glu Asn Phe Lys Gly Lys Ala Thr Leu Thr Ala Asp Lys
            210                 215                 220

Ser Ser Thr Thr Ala Tyr Met Gln Leu Ser Ser Leu Thr Ser Glu Asp
225                 230                 235                 240

Ser Ala Val Tyr Phe Cys Ala Thr Tyr Tyr Asn Tyr Pro Phe Ala Tyr
                245                 250                 255

Trp Gly Gln Gly Thr Leu Val Thr Val Ser Ala Ala Lys Pro Thr Thr
                260                 265                 270

Thr Pro Ala Pro Arg Pro Pro Thr Pro Ala Pro Thr Ile Ala Ser Gln
            275                 280                 285

Pro Leu Ser Leu Arg Pro Glu Ala Cys Arg Pro Ala Ala Gly Gly Ala
            290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
            355                 360                 365

Pro Glu Glu Glu Glu Gly Gly Cys Glu Leu Arg Val Lys Phe Ser Arg
370                 375                 380

Ser Ala Asp Ala Pro Ala Tyr Lys Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
            435                 440                 445

Tyr Ser Glu Ile Gly Met Lys Gly Glu Arg Arg Arg Gly Lys Gly His
            450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490

<210> SEQ ID NO 42
<211> LENGTH: 443
<212> TYPE: PRT
<213> ORGANISM: Artificial Sequence
<220> FEATURE:
<223> OTHER INFORMATION: synthetic
```

<400> SEQUENCE: 42

```
Met Ala Leu Pro Val Thr Ala Leu Leu Leu Pro Leu Ala Leu Leu Leu
1               5                   10                  15

His Ala Ala Arg Pro Leu Pro Ile Cys Pro Gly Gly Ala Ala Arg Cys
            20                  25                  30

Gln Val Thr Leu Arg Asp Leu Phe Asp Arg Ala Val Val Leu Ser His
        35                  40                  45

Tyr Ile His Asn Leu Ser Ser Glu Met Phe Ser Glu Phe Asp Lys Arg
    50                  55                  60

Tyr Thr His Gly Arg Gly Phe Ile Thr Lys Ala Ile Asn Ser Cys His
65                  70                  75                  80

Thr Ser Ser Leu Ala Thr Pro Glu Asp Lys Glu Gln Ala Gln Gln Met
                85                  90                  95

Asn Gln Lys Asp Phe Leu Ser Leu Ile Val Ser Ile Leu Arg Ser Trp
            100                 105                 110

Asn Glu Pro Leu Tyr His Leu Val Thr Glu Val Arg Gly Met Gln Glu
        115                 120                 125

Ala Pro Glu Ala Ile Leu Ser Lys Ala Val Glu Ile Glu Glu Gln Thr
    130                 135                 140

Lys Arg Leu Leu Glu Gly Met Glu Leu Ile Val Ser Gln Val His Pro
145                 150                 155                 160

Glu Thr Lys Glu Asn Glu Ile Tyr Pro Val Trp Ser Gly Leu Pro Ser
                165                 170                 175

Leu Gln Met Ala Asp Glu Glu Ser Arg Leu Ser Ala Tyr Tyr Asn Leu
            180                 185                 190

Leu His Cys Leu Arg Arg Asp Ser His Lys Ile Asp Asn Tyr Leu Lys
        195                 200                 205

Leu Leu Lys Cys Arg Ile Ile His Asn Asn Cys Ala Lys Pro Thr
    210                 215                 220

Thr Thr Pro Ala Pro Arg Pro Thr Pro Ala Pro Thr Ile Ala Ser
225                 230                 235                 240

Gln Pro Leu Ser Leu Arg Pro Glu Ala Cys Arg Pro Ala Ala Gly Gly
                245                 250                 255

Ala Val His Thr Arg Gly Leu Asp Phe Ala Cys Asp Ile Tyr Ile Trp
            260                 265                 270

Ala Pro Leu Ala Gly Thr Cys Gly Val Leu Leu Leu Ser Leu Val Ile
        275                 280                 285

Thr Lys Arg Gly Arg Lys Lys Leu Leu Tyr Ile Phe Lys Gln Pro Phe
    290                 295                 300

Met Arg Pro Val Gln Thr Thr Gln Glu Glu Asp Gly Cys Ser Cys Arg
305                 310                 315                 320

Phe Pro Glu Glu Glu Glu Gly Gly Cys Glu Leu Arg Val Lys Phe Ser
                325                 330                 335

Arg Ser Ala Asp Ala Pro Ala Tyr Lys Gln Gly Gln Asn Gln Leu Tyr
            340                 345                 350

Asn Glu Leu Asn Leu Gly Arg Arg Glu Glu Tyr Asp Val Leu Asp Lys
        355                 360                 365

Arg Arg Gly Arg Asp Pro Glu Met Gly Gly Lys Pro Arg Arg Lys Asn
    370                 375                 380

Pro Gln Glu Gly Leu Tyr Asn Glu Leu Gln Lys Asp Lys Met Ala Glu
385                 390                 395                 400

Ala Tyr Ser Glu Ile Gly Met Lys Gly Glu Arg Arg Arg Gly Lys Gly
                405                 410                 415
```

His Asp Gly Leu Tyr Gln Gly Leu Ser Thr Ala Thr Lys Asp Thr Tyr
            420                 425                 430

Asp Ala Leu His Met Gln Ala Leu Pro Pro Arg
            435                 440

<210> SEQ ID NO 43
<211> LENGTH: 434
<212> TYPE: PRT
<213> ORGANISM: Artificial Sequence
<220> FEATURE:
<223> OTHER INFORMATION: synthetic

<400> SEQUENCE: 43

Met Ala Leu Pro Val Thr Ala Leu Leu Leu Pro Leu Ala Leu Leu Leu
1               5                   10                  15

His Ala Ala Arg Pro Arg Cys Gln Val Thr Leu Arg Asp Leu Phe Asp
            20                  25                  30

Arg Ala Val Val Leu Ser His Tyr Ile His Asn Leu Ser Ser Glu Met
        35                  40                  45

Phe Ser Glu Phe Asp Lys Arg Tyr Thr His Gly Arg Gly Phe Ile Thr
    50                  55                  60

Lys Ala Ile Asn Ser Cys His Thr Ser Ser Leu Ala Thr Pro Glu Asp
65                  70                  75                  80

Lys Glu Gln Ala Gln Gln Met Asn Gln Lys Asp Phe Leu Ser Leu Ile
                85                  90                  95

Val Ser Ile Leu Arg Ser Trp Asn Glu Pro Leu Tyr His Leu Val Thr
            100                 105                 110

Glu Val Arg Gly Met Gln Glu Ala Pro Glu Ala Ile Leu Ser Lys Ala
        115                 120                 125

Val Glu Ile Glu Glu Gln Thr Lys Arg Leu Leu Glu Arg Met Glu Leu
    130                 135                 140

Ile Val Ser Gln Val His Pro Glu Thr Lys Glu Asn Glu Ile Tyr Pro
145                 150                 155                 160

Val Trp Ser Gly Leu Pro Ser Leu Gln Met Ala Asp Glu Glu Ser Arg
                165                 170                 175

Leu Ser Ala Tyr Tyr Asn Leu Leu His Cys Leu Arg Arg Asp Ser His
            180                 185                 190

Lys Ile Asp Asn Tyr Leu Lys Leu Leu Lys Cys Arg Ile Ile His Asn
        195                 200                 205

Asn Asn Cys Ala Lys Pro Thr Thr Thr Pro Ala Pro Arg Pro Pro Thr
    210                 215                 220

Pro Ala Pro Thr Ile Ala Ser Gln Pro Leu Ser Leu Arg Pro Glu Ala
225                 230                 235                 240

Cys Arg Pro Ala Ala Gly Gly Ala Val His Thr Arg Gly Leu Asp Phe
                245                 250                 255

Ala Cys Asp Ile Tyr Ile Trp Ala Pro Leu Ala Gly Thr Cys Gly Val
            260                 265                 270

Leu Leu Leu Ser Leu Val Ile Thr Lys Arg Gly Arg Lys Lys Leu Leu
        275                 280                 285

Tyr Ile Phe Lys Gln Pro Phe Met Arg Pro Val Gln Thr Thr Gln Glu
    290                 295                 300

Glu Asp Gly Cys Ser Cys Arg Phe Pro Glu Glu Glu Glu Gly Gly Cys
305                 310                 315                 320

Glu Leu Arg Val Lys Phe Ser Arg Ser Ala Asp Ala Pro Ala Tyr Lys
                325                 330                 335

```
Gln Gly Gln Asn Gln Leu Tyr Asn Glu Leu Asn Leu Gly Arg Arg Glu
                340                 345                 350

Glu Tyr Asp Val Leu Asp Lys Arg Gly Arg Asp Pro Glu Met Gly
            355                 360                 365

Gly Lys Pro Arg Lys Asn Pro Gln Glu Gly Leu Tyr Asn Glu Leu
370                 375                 380

Gln Lys Asp Lys Met Ala Glu Ala Tyr Ser Glu Ile Gly Met Lys Gly
385                 390                 395                 400

Glu Arg Arg Arg Gly Lys Gly His Asp Gly Leu Tyr Gln Gly Leu Ser
                405                 410                 415

Thr Ala Thr Lys Asp Thr Tyr Asp Ala Leu His Met Gln Ala Leu Pro
                420                 425                 430

Pro Arg

<210> SEQ ID NO 44
<211> LENGTH: 190
<212> TYPE: PRT
<213> ORGANISM: Artificial Sequence
<220> FEATURE:
<223> OTHER INFORMATION: synthetic

<400> SEQUENCE: 44

Arg Cys Gln Val Thr Leu Arg Asp Leu Phe Asp Arg Ala Val Val Leu
1               5                   10                  15

Ser His Tyr Ile His Asn Leu Ser Ser Glu Met Phe Ser Glu Phe Asp
                20                  25                  30

Lys Arg Tyr Thr His Gly Arg Gly Phe Ile Thr Lys Ala Ile Asn Ser
            35                  40                  45

Cys His Thr Ser Ser Leu Ala Thr Pro Glu Asp Lys Glu Gln Ala Gln
        50                  55                  60

Gln Met Asn Gln Lys Asp Phe Leu Ser Leu Ile Val Ser Ile Leu Arg
65                  70                  75                  80

Ser Trp Asn Glu Pro Leu Tyr His Leu Val Thr Glu Val Arg Gly Met
                85                  90                  95

Gln Glu Ala Pro Glu Ala Ile Leu Ser Lys Ala Val Glu Ile Glu Glu
            100                 105                 110

Gln Thr Lys Arg Leu Leu Glu Arg Met Glu Leu Ile Val Ser Gln Val
        115                 120                 125

His Pro Glu Thr Lys Glu Asn Glu Ile Tyr Pro Val Trp Ser Gly Leu
130                 135                 140

Pro Ser Leu Gln Met Ala Asp Glu Glu Ser Arg Leu Ser Ala Tyr Tyr
145                 150                 155                 160

Asn Leu Leu His Cys Leu Arg Arg Asp Ser His Lys Ile Asp Asn Tyr
                165                 170                 175

Leu Lys Leu Leu Lys Cys Arg Ile Ile His Asn Asn Asn Cys
            180                 185                 190

<210> SEQ ID NO 45
<211> LENGTH: 69
<212> TYPE: PRT
<213> ORGANISM: Artificial Sequence
<220> FEATURE:
<223> OTHER INFORMATION: Synthesis

<400> SEQUENCE: 45

Thr Thr Thr Pro Ala Pro Arg Pro Pro Thr Pro Ala Pro Thr Ile Ala
1               5                   10                  15
```

```
Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr Leu Tyr Cys
65
```